US009522930B2

(12) United States Patent
Hertweck et al.

(10) Patent No.: US 9,522,930 B2
(45) Date of Patent: Dec. 20, 2016

(54) CHARTREUSIN ANALOGUES

(71) Applicant: Leibniz-Institut Für Naturstoff-Forschung Und Infektionsbiologie; Hans Knöll Institut, Jena (DE)

(72) Inventors: Christian Hertweck, Leipzig (DE); Hans-Martin Dahse, Jena (DE); Nico Ueberschaar, Jena (DE); Tom Bretschneider, Jena (DE); Kirstin Scherlach, Leipzig (DE); Mikko Metsae-Ketelae, Turku (FI)

(73) Assignee: LEIBNIZ-INSTITUT FÜR NATURSTOFF-FORSCHUNG UND INFEKTIONSBIOLOGIE, Jena (DE)

( * ) Notice: Subject to any disclaimer, the term of this patent is extended or adjusted under 35 U.S.C. 154(b) by 0 days.

(21) Appl. No.: 14/418,010

(22) PCT Filed: Jul. 30, 2013

(86) PCT No.: PCT/EP2013/002257
§ 371 (c)(1),
(2) Date: Jan. 28, 2015

(87) PCT Pub. No.: WO2014/019685
PCT Pub. Date: Feb. 6, 2014

(65) Prior Publication Data
US 2015/0197539 A1    Jul. 16, 2015

(30) Foreign Application Priority Data

Jul. 30, 2012   (EP) ..................................... 12005528

(51) Int. Cl.
*C07H 17/04*     (2006.01)
*C07D 493/06*    (2006.01)
*C07H 17/08*     (2006.01)

(52) U.S. Cl.
CPC .............. *C07H 17/04* (2013.01); *C07D 493/06* (2013.01); *C07H 17/08* (2013.01)

(58) Field of Classification Search
CPC .............................. C07H 17/04; C07D 493/06
See application file for complete search history.

(56) References Cited

U.S. PATENT DOCUMENTS 4,927,919 A * 5/1990 Yamada ................. C07H 17/04
536/17.2

FOREIGN PATENT DOCUMENTS

EP      021982      1/1981
EP      0516155     12/1992

OTHER PUBLICATIONS

A. Jemal, et al.; "Global Cancer Statistics": American Cancer Journal: American Cancer Society, Inc.: vol. 61, No. 2, 2011: p. 69-90.
P.G. Grothaus et al.; "Plant Natural Products in Anticancer Drug Discovery": Current Organic Chemistry 14, Bentham Science Publishers Ltd., 2010; p. 1781-1791.
P. Kirubakaran. et al.; "In silico studies on marine actinomycetes as potential inhibitors for Glioblastoma multiforme": Bioinformation vol. 6(3); 2011; p. 100-106.
J. Verweij et al.; "Phase II studies of Elsamitrucin in breast cancer, colorectal cancer, non-small cell lung cancer and ovarian cancer": Annals of Oncology 5, 1994; Klwer Academic Punlishers; Netherlands; p. 375-376.
G. Asai et al.; "Pharmacokinetic and pharmacodynamic study of IST-622, a novel synthetic derivative of chartreusin, by oral administration in a phase II study of patients with breast cancer": Cancer Chemother Pharmacol, 49, Springer-Verlag 2002; p. 468-472.
Z. Xu et al.; "Biosynthesis of the Antitumor Agent Chartreusin Involves the Oxidative Rearrangement of an Anthracyclic Polyketide"; Chemistry & Biology, vol. 12, Elsevier Ltd., 2005; p. 579-588.
D. Mal et al.; "Convergent and rapid assembly of benzonaphthopyranone cores of chartreusin, chrymutasins and hayumicins"; Tetrahedron Letters; 45, Elsevier Ltd., 2004; p. 7895-7898.
T. Harayama et al.; "Convenient Synthesis of a Simple Coumarin from Salicylaldehyde and Wittig Reagent II: Synthesis of Bromo- and Methoxycarbonylcoumarins": Chem. Pharm. Bull. vol. 42, Pharmaceutical Society of Japan, 1994; p. 2170-2173.
T. Kieser et al.;"Practical Streptomyces Genetics": The John Innes Foundation, Norwich, U.K., 2000.
J. Sambrook.; "Molecular Cloning": a Laboratory Manual, 2nd ed., Cold Spring Harbor, N.Y., 1989.
M. Bierman et al.; "Plasmid cloning vectors for the conjugal transfer of DNA from *Escherichia coli* to streptomyces spp": Gene 116, Elsevier Science Publishers B.V.,1992; p. 43-49.
K. Jakobi; "A Gene Cluster Encoding Resistomycin Biosynthesis in Streptomyces resistomycificus; Exploring Polyketide Cyclization beyond Linear and Angucyclic Patterns": American Chemical Society 2004, 126, p. 2298-2299.
J. Vara et al.; "Cloning of Genes Governing the Deoxysugar Portion of the Erythromycin Biosynthesis Pathway in Saccharopolyspora erythraea": Journal of Bacteriology vol. 171, No. 11, American Society for Microbiology, 1989, p. 5872-5881.
K. Raty et al.; "Cloning and characterization of Streptomyces galilaeus aclacinomycins polyketide synthase (PKS) cluster": Gene 293, Elsevier Science B.V.; 2002, p. 115-122.
K. Scherlach et al.; "Antimitotic Rhizoxin Derivatives from a Cultured Bacterial Endosymbiont of the Rice Pathogenic Fungus Rhizopus microsporus": Journal of the American Chemical Society 128, 2006, p. 11529-11536.

(Continued)

*Primary Examiner* — Jonathan S Lau
(74) *Attorney, Agent, or Firm* — Mintz Levin Cohn Ferris Glovsky and Popeo, P.C.; Peter F. Corless, Esq.; Daniel W. Clarke

(57) ABSTRACT

The present invention relates to novel Chartreusin analogues of formula (I), pharmaceutical compositions comprising the same and to their use for the treatment of cancer and other diseases.

11 Claims, 24 Drawing Sheets

(56) References Cited

OTHER PUBLICATIONS

Figure 1:
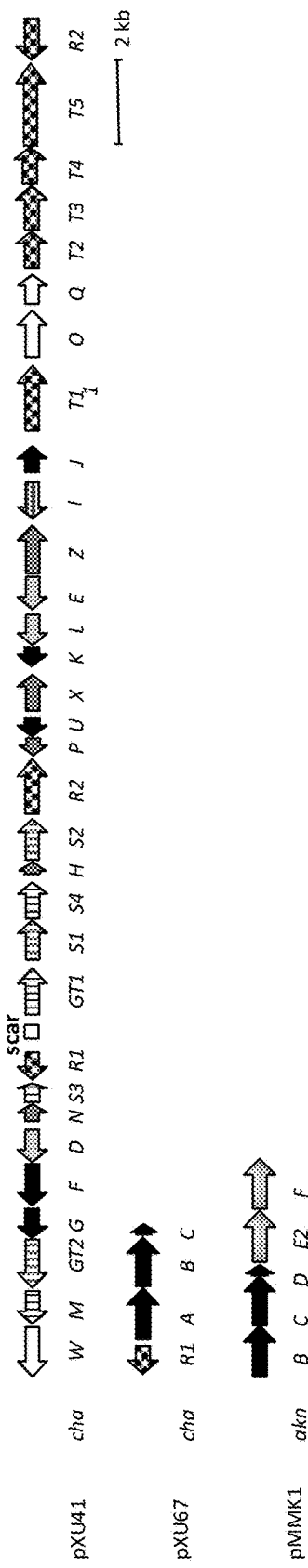

N. Ueberschaar et al.; "Rational Design of an Apoptosis-Inducing Photoreactive DNA Intercalator": Angewandte Chemie Int. Ed., 2013, 52, Wiley-VCH Verlag GmbH & Co. KGaA 2013, p. 6185-6189.
A. Lorico et al.; "Biochemical Characterisation of Elsamicin and Other Coumarin-related Antitumour Agents as Potent Inhibitors of Human Topoisomerase II": European Journal of Cancer, vol. 29, No. 14, Pergamon Press, Oxford, GB, 1. 1993, p. 1985-1991.
T. Tashiro et al.; "Antitumor effects of IST-622, a novel synthetic derivative of chartreusin, against murine and human tumor lines following oral administration": Chancer Chemotherapy and Pharmacology, Springer Verlag, Berlin, vol. 34, No. 4, 1994, p. 287-292.
H. Uchida et al.; "Chrymutasins: Novel-Aglycone Antitumor Antibiotics from a Mutant of Streptomyces chartreusis. I. Taxonomy, Mutation, Fermentation Isolation and Biological Activities": The Journal of Antibiotics, vol. 47, No. 6, 1994, p. 648-654.
M. Takai et al.; "Synthesis and Antitumor Activity of Analogues of the Antitumor Antibiotic Chartreusin": Journal of Mecical Chemistry, vol. 23, No. 5, The American Chemical Society,1980, p. 549-553.
Ueberschaar et al. Bipiperidine conjugates as soluble sugar surrogates in DNA-intercalating antiproliferative polyketides. ChemComm. The Royal Society of Chemistry 2016. 4 pages.
Ueberschaar et al. Supplementary Material for Bipiperidine conjugates as soluble sugar surrogates in DNA-intercalating antiproliferative polyketides. ChemComm. The Royal Society of Chemistry 2016. 51 pages.

\* cited by examiner

FIG. 3A

| position | Chartarin δ | ∫ | m | J₁ | J₂ | norchartarin δ | ∫ | m | J₁ | J₂ | 1-vinylchartarin δ | ∫ | m | J₁ | J₂ | 1-bromochartarin δ | ∫ | m | J₁ | J₂ |
|---|---|---|---|---|---|---|---|---|---|---|---|---|---|---|---|---|---|---|---|---|
| 1 | | | | | | 8.27 | 1 | dd | 6.1 | 2.7 | | | | | | | | | | |
| 1a | 2.88 | 3 | s | | | | | | | | 8.33 | 1 | dd | 17.5 | 11.0 | | | | | |
| 1b$^E$ | | | | | | | | | | | 5.82 | 1 | dd | 17.5 | 1.2 | | | | | |
| 1b$^Z$ | | | | | | | | | | | 5.46 | 1 | dd | 11.0 | 1.2 | | | | | |
| 2 | 7.39 | 1 | d | 8.4 | | 7.76-7.63 | 3 | m | | | 7.81 | 1 | d | 8.6 | | 7.93 | 1 | d | 8.6 | |
| 3 | 7.54 | 1 | d | 8.3 | | 7.76-7.63 | 3 | m | | | 7.61 | 1 | d | 8.7 | | 7.52 | 1 | d | 8.7 | |
| 6 OH | | | | | | | | | | | | | | | | | | | | |
| 7 | 8.26 | 1 | dd | 8.2 | 1.1 | 8.30 | 1 | dd | 8.1 | 0.9 | 8.29 | 1 | dd | 8.2 | 0.9 | 8.22 | 1 | dd | 8.1 | 1.1 |
| 8 | 7.63 | 1 | t | 7.9 | | 7.76-7.63 | 3 | m | | | 7.61 | 1 | t | 8.0 | | 7.67 | 1 | t | 7.9 | |
| 9 | 7.55 | 1 | dd | 7.8 | 1.1 | 7.61 | 1 | dd | 7.7 | 0.9 | 7.52 | 1 | dd | 7.7 | 1.2 | 7.52 | 1 | t | 7.7 | 1.1 |

FIG. 3B

| | chartarin | norchartarin | 1-vinylchartarin | 1-bromochartarin | 1-ethynylchartarin |
|---|---|---|---|---|---|
| 1 | 139.9 | 126.6 | 140.3 | 119.9 | 121.2 |
| 1a | 22.6 | | 135.8 (under solvent peak) | | 82.5 |
| 1b | | | 118.5 | | 87.5 |
| 2 | 133.2 | 130.7 | 129.2 | 136.5 | 137.2 |
| 3 | 121.3 | 121.4 | 121.6 | 122.5 | 121.0 |
| 3a | 147.3 | 149.1 | 148.7 | 148.5 | 148.9 |
| 3a$^1$ | 118.6 | 120.1 | 120.8 | 122.5 | 121.9 |
| 5 | 165.2 | 164.9 | 164.7 | 164.4 | 164.5 |
| 5a | 97.4 | 97.5 | 97.0 | 97.0 | 97.3 |
| 5a$^1$ | 108.5 | 108.4 | 108.6 | 107.8 | 107.9 |
| 6 | 157.4 | 158.2 | 158.1 | 158.2 | 158.0 |
| 6a | 128.0 | 128.3 | 128.7 | 128.4 | 128.4 |
| 7 | 115.7 | 115.8 | 116.0 | 115.7 | 115.8 |
| 8 | 129.5 | 129.5 | 129.4 | 129.9 | 129.9 |
| 9 | 117.4 | 117.5 | 117.4 | 117.6 | 117.7 |
| 10 | 156.6 | 156.7 | 155.5 | 156.9 | 156.9 |
| 10a | 120.7 | 119.0 | 118.5 | 118.5 | 118.7 |
| 10b | 140.3 | 140.2 | 140.4 | 140.5 | 140.9 |
| 12 | 159.5 | 160.1 | 159.4 | 157.3 | 158.1 |
| 12a | 118.3 | 120.6 | 116.6 | 118.6 | 121.3 |

FIG. 4A

| position | chartarin δ | ∫ | m | J₁ | J₂ | norchartarin δ | ∫ | m | J₁ | J₂ | 1-bromochartarin δ | ∫ | m | J₁ | J₂ |
|---|---|---|---|---|---|---|---|---|---|---|---|---|---|---|---|
| 1 | | | | | | 7.72 | 1 | dd | 7.0 | 1.1 | | | | | |
| 1a | 2.88 | 3 | s | | | | | | | | | | | | |
| 1b | | | | | | | | | | | | | | | |
| 1b' | | | | | | | | | | | | | | | |
| 2 | 7.52 | 1 | d | 8.3 | | 7.76 | 1 | t | 7.7 | | 7.79 | 1 | d | 8.6 | |
| 3 | 7.57 | 1 | d | 8.1 | | 8.23 | 1 | dd | 7.7 | 1.1 | 7.54 | 1 | d | 8.6 | |
| 6 OH | 11.68 | 1 | s | | | 11.51 | | s | | | 11.63 | 1 | s | | |
| 7 | 8.22 | 1 | dd | 8.1 | 0.8 | 8.28 | 1 | dd | 8.4 | 1.0 | 8.27 | 1 | dd | 8.4 | 1.0 |
| 8 | 7.64 | 1 | t | 8.1 | | 7.78 | 1 | t | 8.1 | | 7.70 | 1 | t | 8.1 | |
| 9 | 7.46 | 1 | dd | 7.8 | 0.6 | 7.52 | 1 | dd | 7.9 | 0.9 | 7.51 | 1 | dd | 7.9 | 1.0 |
| 10-OCH₂OCH₃ | 5.46 | 2 | s | | | 5.48 | 2 | s | | | 5.47 | 2 | s | | |
| 10-OCH₂OCH₃ | 3.69 | 3 | s | | | 3.68 | 3 | s | | | 3.67 | 3 | s | | |

FIG. 4B

| | 10-MOM-chartarin | 10-MOM-norchartarin | 10-MOM-1-bromochartarin | 10-MOM-1-ethynylchartarin |
|---|---|---|---|---|
| 1 | 140.5 | 126.0 | 120.3 | 120.7 |
| 1a | 22.6 | | | 102.6 |
| 1b | | | | 103.9 |
| 2 | 133.5 | 130.9 | 139.7 | 137.1 |
| 3 | 121.4 | 121.7 | 122.5 | 121.3 |
| 3a | 147.2 | 149.1 | 148.4 | 148.4 |
| 3a¹ | 120.5 | 120.0 | 120.1 | 122.0 |
| 5 | 165.4 | 165.4 | 164.8 | 164.9 |
| 5a | 97.2 | 97.3 | 96.7 | 96.9 |
| 5a¹ | 109.4 | 109.1 | 108.5 | 108.5 |
| 6 | 157.9 | 158.2 | 158.3 | 158.1 |
| 6a | 127.5 | 127.8 | 127.9 | 127.8 |
| 7 | 118.4 | 118.6 | 118.4 | 118.5 |
| 8 | 128.7 | 130.9 | 129.3 | 129.1 |
| 9 | 117.8 | 118.0 | 117.9 | 118.1 |
| 10 | 154.6 | 154.6 | 154.7 | 154.7 |
| 10-OCH₂OCH₃ | 96.8 | 96.8 | 96.7 | 96.7 |
| 10-OCH₂OCH₃ | 57.3 | 57.2 | 57.3 | 57.2 |
| 10a | 120.3 | 120.8 | 120.1 | 120.3 |
| 10b | 139.4 | 139.4 | 139.7 | 139.9 |
| 12 | 159.0 | 160.0 | 157.3 | 157.8 |
| 12a | 118.4 | 135.5 | 118.7 | 120.7 |

FIG. 5

| position | chartreusin[a] δ | J m | J1 | J2 | norchartreusin[a] δ | J m | J1 | J2 | homochartreusin[b] δ | J m | J1 | J2 | 1-vinylchartreusin[a] δ | J m | J1 | J2 | 1-bromochartreusin[a] δ | J m | J1 | J2 |
|---|---|---|---|---|---|---|---|---|---|---|---|---|---|---|---|---|---|---|---|---|
| 1 | 2.73 | 3 s | | | 8.09 | 1 m | | | 3.27 | 2 m | | | 8.19 | 1 dd | 17.5 | 11.0 | | | | |
| 1a | | | | | | | | | 1.23* | 3 t | 7.4 | | 5.63 | 1 d | 11.8 | | | | | |
| 1b | | | | | | | | | | | | | 5.74 | 1 d | 17.4 | | | | | |
| 1b' | | | | | | | | | | | | | | | | | | | | |
| 2 | 7.32 | 1 d | 8.8 | | 7.56 | 1 m | | | 7.65 | 1 d | 8.5 | | 7.76 | 1 d | 8.7 | | 7.87 | 1 d | 8.6 | |
| 3 | 7.47 | 1 d | 8.3 | | 7.56 | 1 m | | | 7.76* | 1 d | 8.3 | | 7.55 | 1 d | 8.5 | | 7.45 | 1 d | 8.6 | |
| 6 OH | | | | | 11.46 | 1 s | | | 11.53 | 1 s | | | | | | | | | | |
| 7 | 8.36 | 1 dd | 8.3 | 0.6 | 8.36 | 1 d | 8.2 | | 8.09 | 1 d | 8.0 | | 8.39 | 1 dd | 8.2 | 0.9 | 8.34 | 1 d | 8.2 | |
| 8 | 7.66 | 1 t | 8.1 | | 7.66 | 1 pt | 8.1 | | 7.73* | 1 t | 8.1 | | 7.66 | 1 pt | 8.1 | | 7.67 | 1 pt | 8.1 | |
| 9 | 7.77 | 1 d | 7.8 | | 7.77 | 1 d | 8.0 | | 7.53 | 1 d | 7.9 | | 7.70 | 1 dd | 7.2 | 1.0 | 7.79 | 1 d | 7.8 | |
| 1' | 5.83 | 1 d | 4.1 | | 5.80 | 1 d | 7.7 | | 5.37 | 1 d | 7.8 | | 5.83 | 1 d | 7.7 | | 5.87 | 1 d | 7.6 | |
| 2' | 5.08 | 1 dd | 9.5 | 7.7 | 5.09 | 1 dd | 9.5 | 7.7 | 3.98 | 1 dd | 9.5 | 7.9 | 5.09 | 1 dd | 9.6 | 7.7 | 5.08 | 1 t | 8.6 | |
| 3' | 3.87 | 1 dd | 10.1 | 3.12 | 4.35 | 1 dd | 9.6 | 3.5 | 3.65* | 1 | ** | | 4.35 | 1 dd | 9.6 | 3.4 | 4.35 | 1 dd | 9.6 | 3.3 |
| 4' | 4.22 | 1 d | 3.4 | | 4.22 | 1 d | 3.5 | | 3.63* | 1 | ** | | 4.22 | 1 d | 3.2 | | 4.22 | 1 d | 3.2 | |
| 5' | 4.12 | 1 q | 6.5 | | 4.13 | 1 q | 6.5 | | 3.95 | 1 q | 6.6 | | 4.12 | 1 q | 6.5 | | 4.13 | 1 q | 6.5 | |
| 6' | 1.58 | 3 d | 6.5 | | 1.58 | 3 d | 6.4 | | 1.22* | 3 d | 6.6 | | 1.58 | 3 d | 6.5 | | 1.56 | 3 d | 7.2 | |
| 1" | 6.56 | 1 d | 4.1 | | 6.58 | 1 d | 4.1 | | 5.44 | 1 d | 4.0 | | 6.57 | 1 d | 4.0 | | 6.49 | 1 d | 4.0 | |
| 2" | 4.57 | 1 dd | 10.0 | 4.1 | 4.53 | 1 dd | 10.1 | 4.1 | 3.38 | 1 dd | 10.1 | 4.0 | 4.58 | 1 dd | 10.1 | 4.0 | 4.59 | 1 dd | 10.0 | 4.0 |
| 3" | 4.34 | 1 dd | 9.6 | 3.5 | 3.85 | 1 dd | 10.1 | 3.2 | 3.09 | 1 dd | 10.1 | 3.1 | 3.88 | 1 dd | 10.1 | 3.1 | 3.88 | 1 dd | 10.1 | 2.9 |
| 3"OMe | 3.34 | 3 s | | | 3.31 | 3 s | | | 3.14 | 3 s | | | 3.34 | 3 s | | | 3.34 | 3 s | | |
| 4" | 4.16 | 1 d | 1.7 | | 4.14 | 1 s | | | 3.60* | 1 dd | ** | 1.8 | 4.16 | 1 d | 1.8 | | 4.15 | 1 s | | |
| 5" | 5.03 | 1 dq | 6.3 | 0.9 | 5.06 | 1 dq | 6.4 | 1.5 | 4.20 | 1 q | 6.5 | | 5.05 | 1 dq | 6.5 | 1.3 | 5.02 | 1 q | 6.4 | |
| 6" | 1.59 | 3 d | 6.5 | | 1.60 | 3 d | 6.5 | | 0.95 | 3 d | 6.5 | | 1.59 | 3 d | 6.5 | | 1.58 | 3 d | 7.2 | |

FIG. 6

| | chartreusin[a,b] | chartreusin[c] | norchartreusin[c] | homochartreusin[a] | 1-vinylchartreusin[c] | 1-bromchartreusin |
|---|---|---|---|---|---|---|
| 1 | 138.4 | 139.8 | 126.6 | 144.7 | 138.6 | 119.9 |
| 1a | 21.6 | 22.5 | - | 27.2 | 136.0 (under solvent peak) | - |
| 1b | - | - | - | 15.6 | 118.3 | - |
| 2 | 133.0 | 133.2 | 130.7 | 131.8 | 129.2 | 136.7 |
| 3 | 120.6 | 121.1 | 121.3 | 121.2 | 121.5 | 122.3 |
| 3a | 146.0 | 147.2 | 148.9 | 146.4 | 148.5 | 148.3 |
| 3a1 | 119.3 | 120.5 | 119.8 | 120.0 | 120.5 | 122.1 |
| 5 | 163.6 | 165.1 | 164.8 | 163.9 | 164.8 | 164.3 |
| 5a | 96.6 | 97.8 | 97.9 | 97.0 | 97.5 | 97.3 |
| 5a1 | 108.1 | 109.5 | 109.1 | 108.5 | 109.4 | 108.7 |
| 6 | 155.4 | 159.5 | 157.5 | 155.4 | 158.1 | 157.5 |
| 6a | 126.0 | 127.7 | 127.8 | 126.1 | 128.7 | 128.0 |
| 7 | 116.3 | 119.9 | 117.9 | 116.3 | 118.1 | 118.0 |
| 8 | 128.3 | 128.8 | 128.9 | 128.4 | 128.9 | 129.4 |
| 9 | 114.3 | 115.5 | 115.5 | 114.4 | 115.6 | 115.7 |
| 10 | 154.0 | 155.5 | 155.5 | 154.2 | 155.5 | 155.5 |
| 10a | 117.8 | 119.7 | 119.8 | 117.9 | 119.7 | 118.7 |
| 10b | 138.5 | 139.9 | 139.8 | 138.5 | 143.0 | 140.1 |
| 12 | 158.3 | 157.4 | 159.9 | 158.0 | 159.4 | 157.1 |
| 12a | 116.8 | 118.5 | 120.6 | 116.3 | 116.7 | 119.5 |
| 1' | 99.6 | 101.6 | 101.7 | 99.5 | 101.6 | 101.4 |
| 2' | 79.8 | 80.7 | 80.4 | 77.9 | 80.7 | 80.7 |
| 3' | 72.0 | 74.6 | 74.6 | 71.9 | 74.6 | 74.6 |
| 4' | 71.2 | 73.1 | 73.1 | 71.2 | 73.1 | 73.0 |
| 5' | 70.2 | 72.3 | 72.2 | 70.2 | 72.3 | 72.3 |
| 6' | 16.5 | 17.5 | 17.5 | 16.5 | 17.6 | 17.5 |
| 1" | 99.3 | 102.3 | 102.3 | 99.5 | 102.4 | 102.2 |
| 2" | 67.4 | 67.8 | 69.3 | 66.9 | 69.4 | 69.4 |
| 3" | 77.9 | 82.0 | 81.9 | 79.8 | 82.0 | 81.9 |
| 3"OMe | 55.8 | 57.2 | 57.5 | 55.8 | 57.1 | 57.1 |
| 4" | 66.9 | 69.4 | 69.7 | 67.4 | 69.8 | 69.7 |
| 5" | 65.7 | 67.2 | 67.7 | 65.8 | 67.8 | 67.9 |
| 6" | 16.4 | 17.5 | 17.5 | 16.5 | 17.5 | 17.5 |

| | | | ESI-MS | ESI-MS² | | | |
|---|---|---|---|---|---|---|---|
| | | | | [M-sugar]⁻ | | [M-sugar₂]⁻ | |
| | R = | M | [M-H]⁻ | observed (frag. 1) | Δm ([M-H]⁻-frag. 1) | observed (frag. 2) | Δm ([M-H]⁻-frag. 2) |
| norchartreusin | H | 626 | 625 (100) | 465 (12) | 160 | 318 (100) | 307 |
| chartreusin | Me | 640 | 639 (100) | 479 (12) | 160 | 332 (100) | 307 |
| homo chartreusin | Et | 654 | 653 (100) | 493 (11) | 160 | 346 (100) | 307 |
| 1-vinyl chartreusin | vinyl | 652 | 651 (100) | 491 (12) | 160 | 344 (100) | 307 |
| 1-bromo chartreusin | Br | 704 | 703 (95) | 543 (14) | 160 | 396 (100) | 307 |
| hydroxy chartreusin (47) | OH | 642 | 641 (100) | 481 (13) | 160 | 334 (100) | 307 |
| methoxy chartreusin (48) | OMe | 656 | 655 (100) | 495 (9) | 307 | 348 (56) | 307 |
| Ethynyl chartreusin (49) | Ethynyl | 650 | 649 (100) | 489 (8) | 160 | 342 (100) | 307 |

FIG. 9

| position | (56) MeOOC-...Br | (57) MeOOC-...Me | (58) MeOOC-...Et | (59) MeOOC-...vinyl | (60) MeOOC-...C≡C-TMS |
|---|---|---|---|---|---|
| 2 | 158.8 | 159.9 | 160.0 | 159.8 | 159.3 |
| 3 | 118.1 | 116.1 | 116.8 | 117.5 | 118.2 |
| 4 | 140.6 | 141.2 | 141.2 | 141.0 | 140.6 |
| 4a | 117.6 | 116.1 | 116.3 | 117.8 | 118.4 |
| 5 | 128.5 | 127.2 | 127.3 | 127.8 | 127.5 |
| 5-COOMe | 164.8 | 166.1 | 166.2 | 166.0 | 165.4 |
| 5-COOMe | 52.9 | 52.5 | 52.5 | 52.7 | 52.7 |
| 6 | 130.3 | 128.3 | 127.3 | 125.2 | 130.6 |
| 7 | 124.6 | 142.0 | 148.2 | 140.5 | 126.1 |
| 7a | - | 21.5 | 28.7 | 134.6 | 102.1 |
| 7b | - | - | 14.8 | 118.3 | 99.7 |
| 8 | 124.1 | 121.3 | 120.1 | 118.1 | 123.6 |
| 8a | 154.9 | 154.7 | 154.9 | 155.1 | 154.4 |
| TMS | - | - | - | - | -0.4 |

FIG. 10

| position | (1→2) abeo 10-MOM-chararin (62) | | | | | (1→2) abeo-10-MOM-homochartarin (63) | | | | | (1→2) abeo-10-MOM-(TMS)ethynylchartarin (65) | | | | | (1→2) abeo-10-MOM-bromochartarin (61) | | | | |
|---|---|---|---|---|---|---|---|---|---|---|---|---|---|---|---|---|---|---|---|---|
| | δ | ∫ | m | J₁ | J₂ | δ | ∫ | m | J₁ | J₂ | δ | ∫ | m | J₁ | J₂ | δ | ∫ | m | J₁ | J₂ |
| 1 | 8.05 | 1 | s | | | 8.09 | 1 | d | 1.1 | | 8.28 | 1 | d | 1.4 | | 8.37 | 1 | d | 1.4 | |
| 2a | 2.61 | 3 | s | | | 2.93 | 2 | q | 7.6 | | | | - | | | | | - | | |
| 2b | | | - | | | 1.39 | 3 | t | 7.6 | | | | - | | | | | - | | |
| 3 | 7.55 | 1 | s | | | 7.60 | 1 | d | 1.4 | | 7.72 | 1 | d | 1.4 | | 7.87 | 1 | d | 1.8 | |
| 6 OH | 11.54 | 1 | s | | | 11.58 | 1 | s | | | 11.52 | 1 | s | | | 11.48 | 1 | s | | |
| 7 | 8.26 | 1 | dd | 8.3 | 0.9 | 8.28 | 1 | dd | 8.3 | 1.0 | 8.26 | 1 | dd | 8.3 | 1.1 | 8.28 | 1 | dd | 8.4 | 0.8 |
| 8 | 7.65 | 1 | dd | 8.1 | 8.1 | 7.67 | 1 | dd | 8.1 | 8.1 | 7.68 | 1 | dd | 8.1 | 8.1 | 7.70 | 1 | dd | 8.1 | 8.1 |
| 9 | 7.50 | 1 | dd | 7.9 | 0.9 | 7.52 | 1 | dd | 7.8 | 1.0 | 7.52 | 1 | dd | 7.9 | 1.0 | 7.54 | 1 | dd | 7.8 | 0.9 |
| 10- OCH₂OCH₃ | 5.48 | 2 | s | | | 5.49 | 2 | s | | | 5.48 | 2 | s | | | 5.48 | 2 | s | | |
| 10- OCH₂OCH₃ | 3.68 | 3 | s | | | 3.70 | 3 | s | | | 3.67 | 3 | s | | | 3.67 | 3 | s | | |
| -C≡C-TMS | | | - | | | | | - | | | 0.30 | 9 | s | | | | | - | | |

FIG. 11

| position | (1→2) abeo-10-MOM-chartarin (62) | (1→2) abeo-10-MOM-homochartarin (63) | (1→2) abeo-10-MOM-(TMS)ethynylchartarin (65) | (1→2) abeo-10-MOM-bromochartarin (61) |
|---|---|---|---|---|
| 1 | 126.1 | 125.0 | 129.5 | 128.7 |
| 2 | 142.5 | 158.8 | 119.8 | 123.7 |
| 2a | 22.3 | 29.8 | 102.8 | - |
| 2b | - | 15.7 | 99.4 | - |
| 3 | 122.4 | 121.5 | 124.0 | 124.9 |
| 3a | 149.1 | 149.3 | 148.3 | 149.5 |
| 3a$^1$ | 117.5 | 117.7 | 120.5 | 119.0 |
| 5 | 165.6 | 165.6 | 165.1 | 164.8 |
| 5a | 97.3 | 97.3 | 97.0 | 96.7 |
| 5a$^1$ | 109.4 | 109.5 | 108.7 | 108.6 |
| 6 | 158.1 | 158.2 | 158.3 | 158.5 |
| 6a | 127.5 | 127.5 | 127.9 | 127.9 |
| 7 | 118.6 | 118.6 | 118.5 | 118.6 |
| 8 | 128.5 | 128.5 | 129.1 | 129.2 |
| 9 | 118.0 | 118.0 | 117.9 | 118.0 |
| 10 | 154.5 | 154.5 | 154.7 | 154.7 |
| 10a | 96.8 | 96.9 | 96.7 | 96.7 |
| 10-OCH$_2$OCH$_3$ | 57.2 | 57.2 | 57.2 | 57.3 |
| 10-OCH$_2$OCH$_3$ | 120.7 | 120.6 | 120.7 | 120.6 |
| 10b | 138.9 | 138.9 | 139.7 | 139.5 |
| 12 | 160.2 | 160.3 | 159.3 | 158.9 |
| 12a | 120.5 | 120.8 | 126.0 | 121.7 |
| TMS | - | - | -0.1 | - |

FIG. 12

| position | (1→2) abeo chartarin (67) | | | | (1→2) abeo-homochartarin (68) | | | | (1→2) abeo-ethynylchartarin (69) | | | | (1→2) abeo bromochartarin (66) | | | |
|---|---|---|---|---|---|---|---|---|---|---|---|---|---|---|---|---|
| | δ | ʃ | m | $J_1$ $J_2$ | δ | ʃ | m | $J_1$ $J_2$ | δ | ʃ | m | $J_1$ $J_2$ | δ | ʃ | m | $J_1$ $J_2$ |
| 1 | 8.07 | 1 | d | 1.4 | 8.15 | 1 | d | 1.4 | 8.45 | 1 | d | 1.3 | 8.45 | 1 | d | 1.7 |
| 2a | 2.38 | 3 | s | | 2.70 | 2 | q | 7.6 | | | | | | | | |
| 2b | | | | | 1.20 | 3 | t | 7.6 | 4.53 | 1 | s | | | | | |
| 2b' | | | - | | | | - | | | | - | | | | - | |
| 3 | 7.45 | 1 | d | 1.4 | 7.52 | 1 | d | 1.4 | 7.84 | 1 | d | 1.3 | 7.95 | 1 | d | 1.7 |
| 7 | 8.29 | 1 | dd | 8.2 1.2 | 8.53 | 1 | dd | 8.2 1.0 | 8.31 | 1 | dd | 8.1 1.0 | 8.32 | 1 | dd | 8.2 0.9 |
| 8 | 7.63 | 1 | dd | 8.0 8.0 | 7.65 | 1 | dd | 7.9 7.9 | 7.67 | 1 | dd | 7.9 7.9 | 7.67 | 1 | dd | 7.9 7.9 |
| 9 | 7.56 | 1 | dd | 7.7 1.2 | 7.58 | 1 | dd | 8.0 1.0 | 7.62 | 1 | dd | 7.6 1.1 | 7.59* | | | |

FIG. 13

| position | (1→2) abeo chartarin (67) | (1→2) abeo-homochartarin (68) | (1→2) abeo-ethynylchartarin (69) | (1→2) abeo bromochartarin (66) |
|---|---|---|---|---|
| 1 | 125.9 | 127.4 | 129.3 | 128.3 |
| 2 | 140.8 | 148.1 | 123.5 | 126.8 |
| 2a | 21.9 | 29.5 | 82.6 | - |
| 2b | - | 15.7 | 83.3 | - |
| 3 | 122.2 | 121.2 | 124.3 | 124.7* |
| 3a | 149.2 | 149.3 | 149.1 | 149.7 |
| 3a¹ | 117.7 | 118.0 | 120.7 | 119.3 |
| 5 | 165.2 | 165.2 | 164.5 | 164.3 |
| 5a | 97.5 | 97.6 | 97.2 | 97.2 |
| 5a¹ | 108.6 | 108.7 | 107.9 | 107.9 |
| 6 | 158.2 | 158.3 | 158.2 | 158.4 |
| 6a | 128.0 | 128.2 | 128.6 | 128.6 |
| 7 | 115.9 | 115.9 | 115.8 | 115.9 |
| 8 | 129.2 | 129.2 | 129.8 | 129.8 |
| 9 | 117.4 | 117.4 | 117.6 | 117.7 |
| 10 | 156.5 | 156.5 | 156.9 | 156.8 |
| 10a | 119.1 | 119.1 | 118.9 | 119.0 |
| 10b | 139.7 | 139.8 | 140.7 | 140.4 |
| 12 | 160.1 | 160.2 | 159.4 | 159.0 |
| 12a | 120.3 | 120.5 | 120.4 | 121.6 |

FIG. 14A

| pos. | chartreusin (1) | | | | | (1→2) abeo-chartreusin (70) | | | | | (1→2) abeo-homochartreusin (71) | | | | |
|---|---|---|---|---|---|---|---|---|---|---|---|---|---|---|---|
| | δ | ∫ | m | $J_1$ | $J_2$ | δ | ∫ | m | $J_1$ | $J_2$ | δ | ∫ | m | $J_1$ | $J_2$ |
| 1 | | | - | | | 7.86 | 1 | s | | | 7.95 | 1 | m | | |
| 1a | 2.73 | 3 | s | | | | | - | | | | | - | | |
| 2 | 7.32 | 1 | d | 8.8 | | | | - | | | | | - | | |
| 2a | | | - | | | 2.32 | 3 | s | | | 2.64 | 2 | m | | |
| 2b | | | - | | | | | - | | | 1.16 | 3 | t | 6.9 | |
| 2b' | | | - | | | | | - | | | | | - | | |
| 3 | 7.47 | 1 | d | 8.3 | | 7.31 | 1 | s | | | 7.39 | 1 | m | | |
| 7 | 8.36 | 1 | dd | 8.3 | 0.6 | 8.48 | 1 | d | 6.8 | | 8.44 | 1 | m | | |
| 8 | 7.66 | 1 | t | 8.1 | | 7.61 | 1 | dd | 8.0 | 8.0 | 7.63 | 1 | m | | |
| 9 | 7.77 | 1 | d | 7.8 | | 7.73 | 1 | d | 7.4 | | 7.75 | 1 | d | 7.7 | |
| 1' | 5.83 | 1 | d | 4.1 | | 5.78 | 1 | d | 7.1 | | 5.79 | 1 | d | 7.6 | |
| 2' | 5.08 | 1 | dd | 9.5 | 7.7 | 5.10 | 1 | dd | 9.6 | 7.6 | 5.11 | 1 | m | | |
| 3' | 4.34 | 1 | dd | 9.6 | 3.5 | 4.34 | 1 | dd | 9.6 | 3.5 | 4.34 | 1 | dd | 9.5 | 3.5 |
| 4' | 4.22 | 1 | d | 3.4 | | 4.21 | 1 | d | 3.7 | | 4.21 | 1 | dd | 2.9 | 2.9 |
| 5' | 4.12 | 1 | q | 6.5 | | 4.11 | 1 | dq | 6.5 | 0.7 | 4.12 | 1 | m | | |
| 6' | 1.58 | 3 | d | 6.5 | | 1.59 | 3 | d | 6.4 | | 1.58 | 3 | d | 6.0 | |
| 1" | 6.56 | 1 | d | 4.1 | | 6.62 | 1 | d | 4.1 | | 6.63 | 1 | m | | |
| 2" | 4.57 | 1 | dd | 10.0 | 4.1 | 4.55 | 1 | dd | 10.1 | 4.1 | 4.55 | 1 | m | | |
| 3" | 3.87 | 1 | dd | 10.1 | 3.1 | 3.87 | 1 | dd | 10.0 | 3.2 | 3.87 | 1 | m | | |
| 3"OMe | 3.34 | 3 | s | | | 3.33 | 3 | s | | | 3.33 | 3 | s | | |
| 4" | 4.16 | 1 | d | 1.7 | | 4.15 | 1 | dd | 3.2 | 1.5 | 4.15 | 1 | dd | 3.1 | 1.3 |
| 5" | 5.03 | 1 | dq | 6.3 | 0.9 | 5.06 | 1 | dq | 6.3 | 1.3 | 5.06 | 1 | q | 6.4 | |
| 6" | 1.59 | 3 | d | 6.5 | | 1.60 | 3 | d | 6.5 | | 1.60 | 3 | d | 6.7 | |

FIG. 14B

| pos. | (1→2) abeo-vinylchartreusin (74) | | | | | (1→2) abeo-ethynylchartreusin (73) | | | | | (1→2) abeo-bromochartreusin (72) | | | | |
|---|---|---|---|---|---|---|---|---|---|---|---|---|---|---|---|
| | δ | ∫ | m | $J_1$ | $J_2$ | δ | ∫ | m | $J_1$ | $J_2$ | δ | ∫ | m | $J_1$ | $J_2$ |
| 1 | 8.14 | 1 | d | 1.3 | | 8.23 | 1 | s | | | 8.17 | 1 | m | | |
| 1a | | | - | | | | | - | | | | | - | | |
| 2 | | | - | | | | | - | | | | | - | | |
| 2a | 6.81 | 1 | dd | 17.5 | 10.9 | | | - | | | | | - | | |
| 2b | 5.38 | 1 | d | 10.9 | | 4.34 | 1 | s | | | | | - | | |
| 2b' | 5.94 | 1 | d | 17.5 | | | | - | | | | | - | | |
| 3 | 7.62 | 1 | m | | | 7.56 | 1 | s | | | 7.65 | 1 | m | | |
| 7 | 8.64 | 1 | m | | | 8.71 | 1 | m | | | 8.64 | 1 | m | | |
| 8 | 7.62 | 1 | m | | | 7.56 | 1 | dd | 7.9 | 7.9 | 7.59 | 1 | | | |
| 9 | 7.73 | 1 | dd | 8.2 | 0.8 | 7.71 | 1 | d | 7.9 | | 7.73 | 1 | d | 7.6 | |
| 1' | 5.79 | 1 | d | 7.6 | | 5.79 | 1 | d | 7.7 | | 5.77 | 1 | d | 7.7 | |
| 2' | 5.10 | 1 | dd | 9.7 | 7.6 | 5.09 | 1 | dd | 9.5 | 7.8 | 5.08 | 1 | dd | 9.5 | 7.8 |
| 3' | 4.33 | 1 | dd | 9.7 | 3.5 | 4.33 | 1 | dd | 9.7 | 3.5 | 4.33 | 1 | dd | 9.5 | 3.4 |
| 4' | 4.20 | 1 | d | 4.0 | | 4.20 | 1 | d | 3.6 | | 4.20 | 1 | d | 3.6 | |
| 5' | 4.10 | 1 | q | 6.6 | | 4.09 | 1 | q | 6.3 | | 4.21 | 1 | q | 6.4 | |
| 6' | 1.57 | 3 | d | 6.4 | | 1.56 | 3 | d | 6.4 | | 1.57 | 3 | d | 6.3 | |
| 1" | 6.62 | 1 | d | 4.1 | | 6.59 | 1 | d | 4.1 | | 6.57 | 1 | d | 3.9 | |
| 2" | 4.56 | 1 | dd | 10.1 | 4.1 | 4.58 | 1 | dd | 10.0 | 3.9 | 4.56 | 1 | dd | 10.1 | 3.9 |
| 3" | 3.88 | 1 | dd | 10.1 | 3.2 | 3.89 | 1 | dd | 10.0 | 3.1 | 3.87 | 1 | dd | 10.1 | 2.9 |
| 3"OMe | 3.35 | 3 | s | | | 3.37 | 3 | s | | | 3.35 | 3 | s | | |
| 4" | 4.15 | 1 | dd | 3.2 | 1.4 | 4.15 | 1 | d | 3.1 | | 4.15 | 1 | dd | 3.0 | 1.1 |
| 5" | 5.05 | 1 | dq | 6.5 | 1.3 | 5.06 | 1 | q | 6.5 | | 5.05 | 1 | q | 6.4 | |
| 6" | 1.60 | 3 | d | 6.5 | | 1.59 | 3 | d | 6.5 | | 1.60 | 3 | d | 6.5 | |

FIG. 15A

| pos. | chartreusin (1) | (1→2) abeo-chartreusin (70) | (1→2) abeo-homochartreusin (71) |
|---|---|---|---|
| 1 | 139.8 | 125.5 | 124.5 |
| 1a | 22.5 | - | - |
| 2 | 133.2 | 141.4 | 147.8 |
| 2a | - | 21.8 | 29.4 |
| 2b | - | - | 15.6 |
| 3 | 121.1 | 121.7 | 120.5 |
| 3a | 147.2 | 149.4 | 147.7 |
| 3a$^1$ | 120.5 | 120.2 | 120.8 |
| 5 | 165.1 | 164.8 | 164.9 |
| 5a | 97.8 | 97.2 | 97.5 |
| 5a$^1$ | 109.5 | 110.1 | 109.7 |
| 6 | 159.5 | 160.5 | 160.2 |
| 6a | 127.7 | 129.2 | 128.2 |
| 7 | 119.9 | 118.6 | 120.6 |
| 8 | 128.8 | 128.0 | 128.3 |
| 9 | 115.5 | 115.3 | 115.3 |
| 10 | 155.5 | 155.3 | 155.4 |
| 10a | 119.7 | 120.4 | 120.2 |
| 10b | 139.9 | 137.9 | 140.4 |
| 12 | 157.4 | 160.2 | 160.2 |
| 12a | 118.5 | 117.9 | 120.7 |
| 1' | 101.6 | 101.8 | 101.8 |
| 2' | 80.7 | 80.6 | 80.6 |
| 3' | 74.6 | 74.6 | 74.7 |
| 4' | 73.1 | 73.1 | 73.1 |
| 5' | 72.3 | 72.2 | 72.2 |
| 6' | 17.5 | 17.6 | 17.6 |
| 1" | 102.3 | 102.3 | 102.3 |
| 2" | 67.8 | 69.4 | 69.4 |
| 3" | 82.0 | 82.0 | 82.0 |
| 3"OMe | 57.2 | 57.2 | 57.2 |
| 4" | 69.4 | 69.4 | 69.8 |
| 5" | 67.2 | 67.7 | 67.7 |
| 6" | 17.5 | 17.6 | 17.6 |

FIG. 15B

| pos. | (1→2) abeo-vinylchartreusin (74) | (1→2) abeo-ethynylchartreusin (73) | (1→2) abeo bromochartreusin (72) |
|---|---|---|---|
| 1 | 122.9 | 128.1 | 127.1 |
| 1a | - | - | - |
| 2 | 139.9 | 123.5 | 127.1 |
| 2a | 136.1 | 83.1 | - |
| 2b | 117.3 | 82.2 | - |
| 3 | 117.6 | 122.7 | 121.6 |
| 3a | 148.7 | 150.1* | 151.3 |
| 3a$^1$ | 120.9 | 121.7 | 120.1 |
| 5 | 164.4 | 163.3 | 164.5 |
| 5a | 96.0 | 95.0 | 95.4 |
| 5a$^1$ | 110.8 | 111.2 | 110.5 |
| 6 | 159.5 | 163.4 | 163.2 |
| 6a | 127.6 | 128.1 | 127.0 |
| 7 | 119.5 | 120.1 | 119.5 |
| 8 | 127.7 | 127.4 | 127.6 |
| 9 | 115.4 | 115.4 | 115.4 |
| 10 | 155.3 | 155.2 | 155.2 |
| 10a | 120.5 | 120.9 | 120.4 |
| 10b | 139.9 | 140.7 | 140.1 |
| 12 | 160.4 | 159.9 | 159.3 |
| 12a | 119.5 | 120.6 | 122.4 |
| 1' | 101.7 | 101.6 | 101.6 |
| 2' | 80.5 | 80.5 | 80.5 |
| 3' | 74.6 | 74.6 | 74.5 |
| 4' | 73.2 | 73.2 | 73.1 |
| 5' | 72.2 | 72.1 | 72.1 |
| 6' | 17.5 | 17.5 | 14.5 |
| 1" | 102.2 | 102.1 | 102.1 |
| 2" | 69.3 | 69.3 | 69.3 |
| 3" | 82.0 | 82.0 | 81.9 |
| 3"OMe | 57.2 | 57.2 | 57.1 |
| 4" | 69.8 | 69.9 | 69.7 |
| 5" | 67.7 | 67.7 | 67.7 |
| 6" | 17.5 | 17.6 | 15.5 |

| | R = | M | ESI–MS | ESI–MS² | | | |
|---|---|---|---|---|---|---|---|
| | | | | [M−sugar]⁻ | | [M−sugar₂]⁻ | |
| | | | [M−H]⁻ | observed (frag. 1) | Δm ([M−H]⁻ frag. 1) | observed (frag. 2) | Δm ([M−H]⁻ frag. 2) |
| chartreusin (1) | | 640 | 639 (100) | 479 (12) | 160 | 332 (100) | 307 |
| (1→2) abeo chartreusin (70) | Me | 640 | 639 (100) | 479 (11) | 160 | 332 (100) | 307 |
| (1→2) abeo homo chartreusin (71) | Et | 654 | 653 (100) | 493 (7) | 160 | 346 (100) | 307 |
| (1→2) abeo vinyl chartreusin (74) | vinyl | 652 | 651 (100) | 491 (8) | 160 | 344 (100) | 307 |
| (1→2) abeo alkynyl chartreusin (73) | alkynyl | 650 | 649 (100) | 489 (8) | 160 | 342 (100) | 307 |
| (1→2) abeo bromo chartreusin (72) | Br | 704 | 703 (96) | 543 (10) | 160 | 396 (100) | 307 |

FIG. 17A

| pos. | (33) δ | J | m | J | (35) δ | J | m | J | (34) δ | J | m | J | (36) δ | J | m | J | (37) δ | J | m | J |
|---|---|---|---|---|---|---|---|---|---|---|---|---|---|---|---|---|---|---|---|---|
| 3 | 6.45 | 1 | d | 10.2 | 6.46 | 1 | d | 9.8 | 6.45 | 1 | d | 9.8 | 6.56 | 1 | d | 10.0 | 6.64 | 1 | d | 9.9 |
| 4 | 8.65 | 1 | d | 10.2 | 7.74 | 1 | d | 9.8 | 7.74 | 1 | d | 9.8 | 8.11 | 1 | d | 10.0 | 7.87 | 1 | d | 9.9 |
| COOMe | 4.04 | 3 | s | - | 3.97 | 3 | s | - | 3.97 | 3 | s | - | 4.02 | 3 | s | - | 3.97 | 3 | s | - |
| OH | 11.22 | 1 | s | - | - | - | - | - | - | - | - | - | - | - | - | - | - | - | - | - |
| OMe | - | - | - | - | 3.88 | 3 | s | - | 3.48 | 3 | s | - | - | - | - | - | - | - | - | - |
| OCH₂O | - | - | - | - | - | - | - | - | 5.18 | 2 | s | - | - | - | - | - | - | - | - | - |
| 6/6a | - | - | - | - | - | - | - | - | - | - | - | - | - | - | - | - | - | - | - | - |
| 7 | 7.15 | 1 | d | 9.2 | 7.15 | 1 | d | 9.2 | 7.38 | 1 | d | 9.2 | 7.45 | 1 | d | 9.2 | 7.62 | 1 | d | 8.7 |
| 8 | 7.39 | 1 | d | 9.2 | 7.37 | 1 | d | 9.2 | 7.33 | 1 | d | 9.2 | 7.50 | 1 | d | 9.2 | 7.31 | 1 | d | 8.7 |
| TMS | - | - | - | - | - | - | - | - | - | - | - | - | - | - | - | - | 0.23 | 9 | s | - |

| pos. | δ | J | m | J |
|---|---|---|---|---|
| 3 | 6.47 | 1 | d | 9.9 |
| 4 | 7.64 | 1 | d | 9.9 |
| COOMe | 4.00 | 3 | s | - |
| 6 | - | | | |
| 7 | 7.67 | 1 | d | 8.9 |
| 8 | 7.25 | 1 | d | 9.1 |

FIG. 17B

FIG. 18

| pos. | (32) Br-MeOOC-coumarin | (33) OH-MeOOC-coumarin | (35) OMe-MeOOC-coumarin | (34) OMOM-MeOOC-coumarin | (36) OTf-MeOOC-coumarin δ | (36) m | (36) J | (37) TMS-ethynyl-MeOOC-coumarin |
|---|---|---|---|---|---|---|---|---|
| 2 | 158.9 | 159.5 | 159.9 | 159.9 | 158.5 | | | 159.4 |
| 3 | 118.6 | 117.7 | 118.3 | 118.1 | 119.3 | | | 118.5 |
| 4 | 139.7 | 141.6 | 140.2 | 140.1 | 139.8 | | | 140.4 |
| 4a | 117.7 | 117.2 | 117.2 | 117.0 | 118.7 | | | 116.9 |
| 5 | 133.4 | 106.8 | 119.6 | 121.1 | 124.4 | | | 134.3 |
| 5-COOMe | 165.8 | 170.4 | 166.0 | 165.9 | 163.0 | | | 166.5 |
| 5-COOMe | 53.2 | 53.0 | 52.8 | 52.8 | 53.4 | | | 53.0 |
| 6 | 114.8 | 160.0 | 153.4 | 151.0 | 143.0 | | | 118.7 |
| 6a | - | - | - | 95.6 (CH$_2$) | | | | 100.9 |
| 6b | - | - | - | 56.4 (CH$_3$) | | | | 99.8 |
| 7 | 119.7 | 124.7 | 115.7 | 119.9 | 125.0 | | | 135.9 |
| 8 | 135.6 | 122.5 | 119.4 | 119.5 | 121.1 | | | 119.0 |
| 8a | 153.0 | 148.4 | 148.0 | 148.9 | 153.2 | | | 153.8 |
| TMS | - | - | 56.9 (CH$_3$) | | | | | 0.0 |
| CF$_3$ | - | - | - | - | 118.5 | q | 320.5 | - |

FIG. 19

| pos. | δ | ∫ | m | $J_1$ | $J_2$ |
|---|---|---|---|---|---|
| 1 | | | - | | |
| 1a | | | - | | |
| 1b | 4.72 | 1 | s | | |
| 2 | 7.93 | 1 | d | 8.4 | |
| 3 | 7.63 | 1 | d | 8.5 | |
| 6 OH | | | | | |
| 7 | 8.29 | 1 | dd | 7.8 | 0.7 |
| 8 | 7.66 | 1 | dd | 7.9 | 7.9 |
| 9 | 7.55 | 1 | dd | 7.7 | 0.8 |

FIG. 20

| pos. | δ | ∫ | m | $J_1$ | $J_2$ |
|---|---|---|---|---|---|
| TMS | 0.34 | 9 | 1 | | |
| 1 | | | | | |
| 1a | | | | | |
| 1b | | | | | |
| 2 | 7.84 | 1 | d | 8.5 | |
| 3 | 7.61 | 1 | d | 8.5 | |
| 6 OH | 11.57 | 1 | s | | |
| 7 | 8.23 | 1 | dd | 8.4 | 1.1 |
| 8 | 7.66 | 1 | dd | 8.1 | 8.1 |
| 9 | 7.50 | 1 | dd | 7.9 | 1.0 |
| 10-$OCH_2OCH_3$ | 5.32 | 2 | S | | |
| 10-$OCH_2OCH_3$ | 3.67 | 3 | s | | |

FIG. 21

| position | hydroxychartreusin (47)[a] | | | | | ethynylchartreusin (49)[a] | | | | | methoxychartreusin (48)[b] | | | | |
|---|---|---|---|---|---|---|---|---|---|---|---|---|---|---|---|
| | $\delta$ | $\int$ | m | $J_1$ | $J_2$ | $\delta$ | $\int$ | m | $J_1$ | $J_2$ | $\delta$ | $\int$ | m | $J_1$ | $J_2$ |
| 1 | - | | | | | - | | | | | - | | | | |
| 1a | - | | | | | - | | | | | - | | | | |
| 1b | - | | | | | 4.53 | 1 | s | | | 3.94 | 3 | s | | |
| 2 | 7.17 | 1 | d | 8.9 | | 7.77 | 1 | d | 8.3 | | 7.20 | 1 | d | 9.2 | |
| 3 | 7.53 | 1 | d | 8.9 | | 7.38 | 1 | d | 8.4 | | 7.56 | 1 | d | 9.0 | |
| 6 OH | | | | | | | | | | | | | | | |
| 7 | 8.36 | 1 | d | 8.2 | | 8.65 | 1 | d | 8.3 | | 8.19 | 1 | d | 8.1 | |
| 8 | 7.65 | 1 | dd | 8.0 | 8.0 | 7.57 | 1 | m | 8.0 | | 7.95 | 1 | dd | 8.0 | 8.0 |
| 9 | 7.77 | 1 | d | 7.8 | | 7.75 | 1 | dd | 8.4 | 1.1 | 7.30 | 1 | d | 7.9 | |
| 1' | 5.81 | 1 | d | 7.6 | | 5.92 | 1 | d | 7.6 | | 5.30 | 1 | d | 7.8 | |
| 2' | 5.05 | 1 | dd | 9.6 | 7.6 | 5.12 | 1 | dd | 7.5 | 9.6 | 3.94 | 1 | dd | 8.9 | 7.2 |
| 3' | 4.34 | 1 | dd | 9.5 | 3.3 | 4.37 | 1 | dd | 3.5 | 9.6 | 3.62 | 1 | m | | |
| 4' | 4.22 | 1 | dd | 3.8 | 0.9 | 4.20 | 1 | d | 3.6 | | 3.60 | 1 | m | | |
| 5' | 4.12 | 1 | dq | 6.7 | 1.0 | 5.08 | 1 | dd | 3.6 | 0.9 | 3.90 | 1 | q | 6.5 | |
| 6' | 1.59 | 3 | d | 6.4 | | 1.53 | 3 | d | 6.2 | | 1.19 | 1 | d | 6.4 | |
| 1" | 6.53 | 1 | d | 4.0 | | 6.51 | 1 | d | 4.1 | | 5.48 | 1 | d | 3.5 | |
| 2" | 4.59 | 1 | dd | 10.0 | 3.9 | 4.62 | 1 | dd | 4.1 | 10.0 | 3.40 | 1 | dd | 10.2 | 4.2 |
| 3" | 3.87 | 1 | dd | 10.0 | 2.8 | 3.94 | 1 | dd | 3.2 | 10.0 | 3.12 | 1 | dd | 10.1 | 3.0 |
| 3"OMe | 3.34 | 3 | s | | | 3.39 | 1 | s | | | 3.17 | 3 | s | | |
| 4" | 4.18 | 1 | dd | 3.3 | 1.5 | 4.14 | 1 | dd | 3.1 | 1.2 | 3.60 | 1 | m | | |
| 5" | 5.06 | 1 | dq | 7.0 | 1.4 | 5.04 | 1 | dd | 6.5 | 1.4 | 5.24 | 1 | q | 6.3 | |
| 6" | 1.64 | 3 | d | 6.4 | | 1.51 | 1 | d | 6.5 | | 0.99 | 3 | d | 6.5 | |

FIG. 22

| pos. | hydroxychartreusin (47)[a] | Ethynyl(49)[a] | Methoxy (48)[b] |
|---|---|---|---|
| 1 | 158.3 | 119.4 | 156.4 |
| 1a |  | 83.1 | - |
| 1b |  | 86.2 | 56.3 |
| 2 | 117.8 | 136.8 | 112.7 |
| 3 | 124.6 | 120.1 | 121.3 |
| 3a | 141.1 | 149.8 | 142.6 |
| 3a[1] | 119.0 | 122.1 | 121.9 |
| 5 | 165.1 | 164.6 | 164.6 |
| 5a | 97.8 | 95.3 | 92.4 |
| 5a[1] | 110.1 | 110.8 | 110.8 |
| 6 | 157.9 | 163.2 | 156.2 |
| 6a | 127.9 | 126.8 | 133.7 |
| 7 | 117.8 | 119.7 | 118.8 |
| 8 | 128.9 | 127.6 | 125.7 |
| 9 | 115.6 | 125.6 | 113.6 |
| 10 | 155.3 | 155.0 | 153.4 |
| 10a | 119.7 | 120.5 | 118.7 |
| 10b | 139.1 | 138.4 | 132.4 |
| 12 | 163.1 | 158.5 | 161.3 |
| 12a | 104.5 | 121.3 | 106.7 |
| 1' | 101.6 | 101.1 | 99.0 |
| 2' | 80.7 | 80.3 | 77.5 |
| 3' | 74.7 | 74.3 | 72.0 |
| 4' | 73.1 | 73.1 | 71.3 |
| 5' | 72.3 | 72.2 | 70.1 |
| 6' | 17.5 | 17.5 | 16.5 |
| 1" | 102.6 | 101.6 | 99.4 |
| 2" | 69.4 | 69.4 | 67.1 |
| 3" | 82.0 | 81.9 | 79.9 |
| 3"OMe | 57.2 | 57.2 | 56.0 |
| 4" | 69.8 | 69.8 | 67.5 |
| 5" | 67.8 | 67.8 | 65.7 |
| 6" | 17.6 | 17.4 | 16.5 |

CHARTREUSIN ANALOGUES

CROSS-REFERENCE TO RELATED APPLICATIONS

This application is a national stage application, filed under 35 U.S.C §371, of International Application No. PCT/EP2013/002257 filed on Jul. 30, 2013, which claims priority to European application no. 12005528.0, filed Jul. 30, 2012, the contents of which are incorporated herein by reference.

INCORPORATION-BY-REFERENCE OF SEQUENCE LISTING

The contents of the text file named "48361-002N01US.txt", which was created on Jan. 28, 2015 and is 3.09 KB in size, are hereby incorporated by reference in their entireties.

The present invention relates to novel Chartreusin analogues, pharmaceutical compositions comprising the same and to their use for the treatment of cancer and other diseases.

One of the biggest medicinal challenges is the treatment of cancer, which has recently become the second leading cause of death among seniors (Jemal, A. et al. Global Cancer Statistics. *CA: A Cancer Journal for Clinicians* 61, 69-90 (2011)). Although much progress has been made in the development of monoclonal antibodies and small-molecule compounds that specifically target tumor cells, natural products from plant, fungi and bacteria still represent the prime source of antitumoral agents that help expanding the life expectancy of the patients (Grothaus, P. G., Cragg, G. M. & Newman, D. J. Plant Natural Products in Anticancer Drug Discovery. *Current Organic Chemistry* 14, 1781-1791 (2010)). The most effective chemotherapeutics either interfere with the tumor cell cycle and division or bind to DNA and cause apoptosis through various downstream processes.

This prominent mode of action is known for the bacterial metabolites chartreusin and elsamicin A. Common to both of these polyketide glycosides is the pentacyclic benzo-naphtho pyranone aglycone named chartarin.

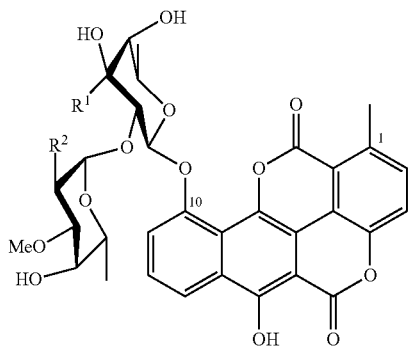

Chartreusin: $R^1 = H$, $R^2 = OH$
Elsamicin A: $R^1 = CH_3$, $R^2 = NH_2$
Chartarin: Aglycone

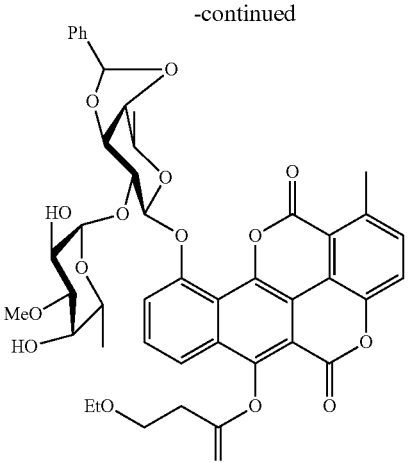

IST-622

This rare chromophore is capable of intercalating into DNA, inhibiting RNA synthesis and causing radical-mediated single-strand scission of DNA. Moreover, chartreusin and elsamicin efficiently inhibit topoisomerase II, a prime target of chemotherapeutics used to treat human malignancies (Lorico, A. & Long, B. H. Biochemical-Characterization of Elsamicin and Other Coumarin-Related Antitumor Agents as Potent Inhibitors of Human Topoisomerase-Ii. *Eur. J. Cancer* 29A, 1985-1991 (1993)). Indeed, chartreusin proved to be highly effective against various cancer cell lines (such as murine P388, L1210 leukemia, and B16 melanoma cells). Additionally, recent in-silico docking studies suggested potential activity of chartreusin against glioblastoma multiforme, one of the most common and most malignant brain tumors (Kirubakaran, P. et al. In silico studies on marine actinomycetes as potential inhibitors for Glioblastoma multiforme. *Bioinformation* 6, 100-106 (2011)). Unfortunately, due to unfavorable pharmacokinetics and rapid biliary excretion, chartreusin has not yet found any clinical application (Tashiro, T. et al. Antitumor effects of IST-622, a novel synthetic derivative of chartreusin, against murine and human tumor lines following oral administration. *Cancer Chemother. Pharmacol.* 34, 287-292 (1994)). Likewise, elsamicin A has so far not gone beyond phase II, as it was not effective enough in vivo (Verweij, J. et al. Phase-II Studies of Elsamitrucin in Breast-Cancer, Colorectal-Cancer, Nonsmall Cell Lung-Cancer and Ovarian-Cancer. *Annals of Oncology* 5, 375-376 (1994)). A program focusing on the chemical modification of the hydroxyl moieties of chartreusin yielded a semi-synthetic derivative IST-622, which may be regarded as a prodrug with improved solubility. IST-622 has entered phase II of clinical trials in Japan for the treatment of patients with breast cancer (Asai, G. et al. Pharmacokinetic and pharmacodynamic study of IST-622, a novel synthetic derivative of chartreusin, by oral administration in a phase II study of patients with breast cancer. *Cancer Chemother. Pharmacol.* 49, 468-472 (2002)).

Accordingly, it has been the object of the present invention to provide new analogues of Chartreusin having improved properties.

The present invention provides compounds of formula (I)

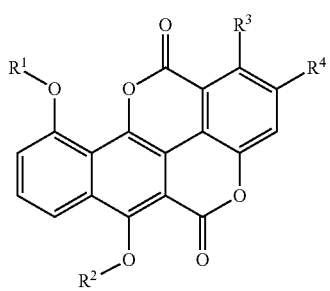

(I)

wherein
R$^1$ is hydrogen or a mono-, di-, tri- or tetra saccharide or a derivative thereof or a 1,4'-bipiperidine-1'carboxylate group;
R$^2$ is a hydrogen atom, or a 1,4'-bipiperidine-1'carboxylate group, or a group of formula —X—(CH$_2$—CH$_2$—O)$_n$—R$^5$ wherein X is a bond, a —C(=O)—, —C(=O)—O— or a —C(=O)—Y—O— group wherein Y is an alkylene group, n is an integer of from 2 to 100, and R$^5$ is hydrogen or an alkyl group;
R$^3$ is selected from a hydrogen atom, a halogen atom, a hydroxy group, a (C$_1$-C$_8$) alkoxy group, a (C$_2$-C$_8$) alkyl group, a (C$_2$-C$_8$) haloalkyl group, a (C$_2$-C$_8$) alkenyl group, or a (C$_2$-C$_8$) alkynyl group and R$^4$ is hydrogen; or
R$^3$ is hydrogen and R$^4$ is selected from a hydrogen atom, a halogen atom, a hydroxy group, a (C$_1$-C$_8$) alkoxy group, a (C$_2$-C$_8$) alkyl group, a (C$_2$-C$_8$) haloalkyl group, a (C$_2$-C$_8$) alkenyl group, or a (C$_2$-C$_8$) alkynyl group;
or a pharmaceutically acceptable salt, solvate or hydrate or a pharmaceutically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expression (C$_2$-C$_8$) alkyl refers to an alkyl group that contains from 2 to 8 (e.g. 2, 3 or 4) carbon atoms.

The expression alkoxy refers to an alkyl group as defined above which is bonded to an oxygen atom, i.e. to a group of formula alkyl-O—. for example a methyloxy (methoxy), ethyloxy (ethoxy), propyloxy, iso-propyloxy, n-butyloxy, iso-butyloxy, sec-butyloxy or tert-butyloxy group. The expression (C$_1$-C$_8$) alkoxy group refers to a group of formula (C$_1$-C$_8$) alkyl-O—.

The expression alkenyl refers to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl(vinyl), propenyl(allyl), iso-propenyl, butenyl, isoprenyl or hex-2-enyl group. Preferably, alkenyl groups have one or two (especially preferably one) double bond(s).

The expression (C$_2$-C$_8$) alkenyl refers to an alkenyl group that contains from 2 to 8 (e.g. 2, 3 or 4) carbon atoms and preferably one or two (especially one) double bond(s).

The expression alkynyl refers to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethynyl(acetylenyl), propynyl, butynyl or propargyl group. Preferably, alkynyl groups have one or two (especially preferably one) triple bond(s).

The expression (C$_2$-C$_8$) alkynyl refers to an alkynyl group that contains from 2 to 8 (e.g. 2, 3 or 4) carbon atoms and preferably one or two (especially one) triple bond(s).

The term haloalkyl refers to an alkyl group in which one or more hydrogen atoms (e.g. 1, 2, 3, 4 or 5) have been replaced by a halogen atom (preferably F or Cl) such as, for example, a 2,2,2-trichloroethyl or a 2,2,2-trifluoroethyl group.

The expression (C$_2$-C$_8$) haloalkyl refers to a haloalkyl group that contains from 2 to 8 (e.g. 2, 3 or 4) carbon atoms.

The expression halogen atom refers to a fluorine, chlorine, bromine or iodine atom; preferably to a chlorine or bromine atom; especially preferably a bromine atom.

The expression mono-, di-, tri- or tetra saccharide refers to groups containing one, two, three or four saccharide moieties, preferably selected from glucoside, fucoside, digitaloside, elsaroside or elsamiside that are preferably bound to each other via a glycosidic bond. The term derivative thereof preferably relates to acetates, methyethers or acetals (preferably of benzaldehyde) thereof.

According to a preferred embodiment, the present invention provides compounds of formula (I) wherein
R$^1$ is hydrogen or a mono-, di-, tri- or tetra saccharide or a derivative thereof;
R$^2$ is a hydrogen atom, or a group of formula —X—(CH$_2$—CH$_2$—O)$_n$—R$^5$ wherein X is a bond, a —C(=O)—, —C(=O)—O— or a —C(=O)—Y—O— group wherein Y is an alkylene group, n is an integer of from 2 to 100, and R$^5$ is hydrogen or an alkyl group;
R$^3$ is a group selected from a halogen atom, a (C$_2$-C$_8$) alkyl group, a (C$_2$-C$_8$) haloalkyl group, or a (C$_2$-C$_8$) alkenyl group and R$^4$ is hydrogen; or
R$^3$ is hydrogen and R$^4$ is a group selected from a halogen atom, a (C$_2$-C$_8$) alkyl group, a (C$_2$-C$_8$) haloalkyl group, or a (C$_2$-C$_8$) alkenyl group;
or a pharmaceutically acceptable salt, solvate or hydrate or a pharmaceutically acceptable formulation thereof.

Preferably, R$^1$ is hydrogen.

Further preferably, R$^1$ is a disaccharide or a derivative thereof.

Moreover preferably, R$^1$ is a 1,4'-bipiperidine-1'carboxylate group:

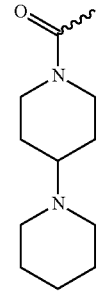

1,4'-bipiperidine-1'-carboxylate

Especially preferably, R¹ is selected from the following groups:

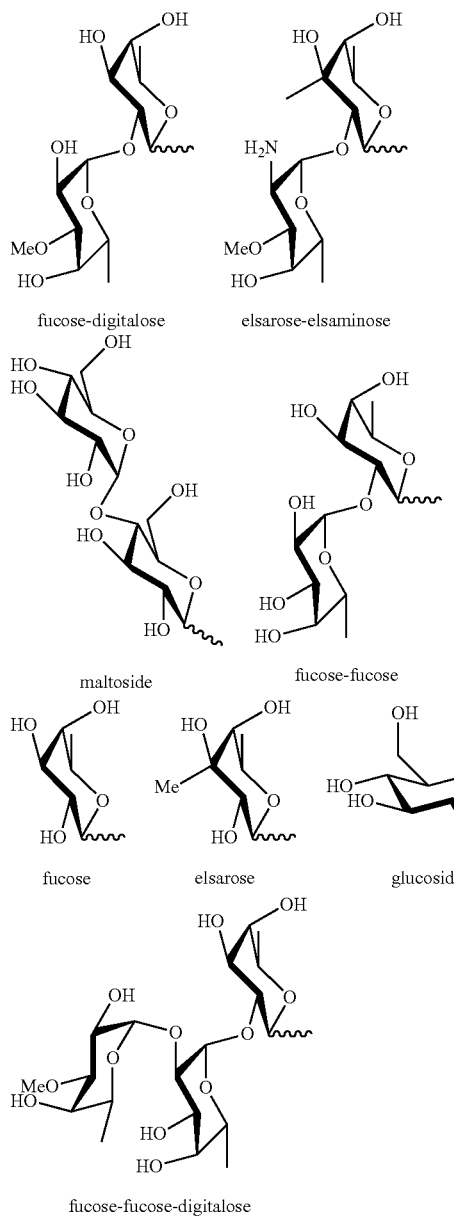

Most preferably, R¹ is fucose-digitalose or a 1,4'-bipiperidine-1'carboxylate group (especially most preferably, R¹ is fucose-digitalose).

Preferably, R² is a hydrogen atom.

Further preferably, R² is a 1,4'-bipiperidine-1'carboxylate group.

Further preferably, R² is a group of formula —X—(CH₂—CH₂—O)$_n$—R⁵ wherein X is a bond, a —C(=O)—, —C(=O)—O— or a —C(=O)—Y—O— group wherein Y is an alkylene group, n is an integer of from 2 to 100, and R⁵ is hydrogen or an alkyl group.

Especially preferably, Y is a group of formula (CH₂)$_m$, wherein m is an integer from 1 to 20.

Moreover preferably, R³ is an ethyl or a vinyl group and R⁴ is a hydrogen atom.

Further preferably, R⁴ is an ethyl or a vinyl group and R³ is a hydrogen atom.

Further preferably, R⁵ is hydrogen, methyl or ethyl.

Especially preferably, the compounds of formula (I) are selected from the following compounds:

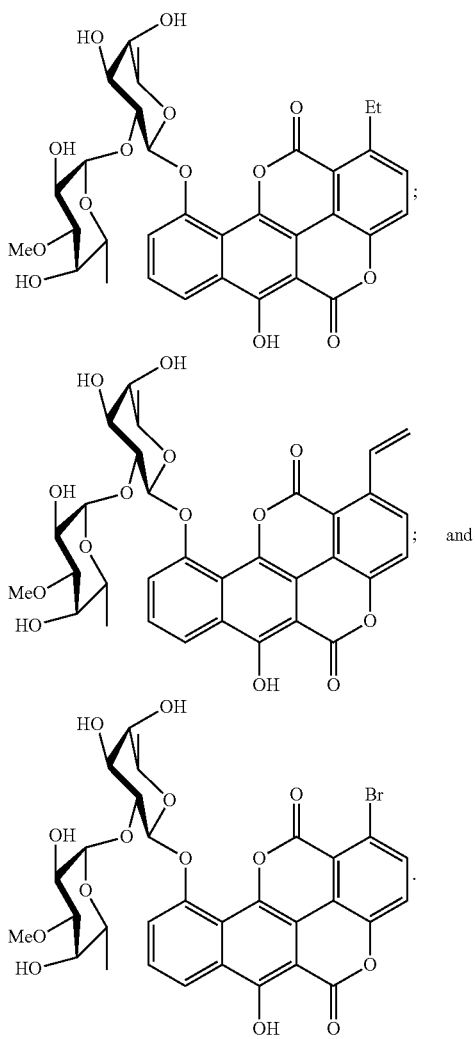

Further preferred are compounds of formula (II):

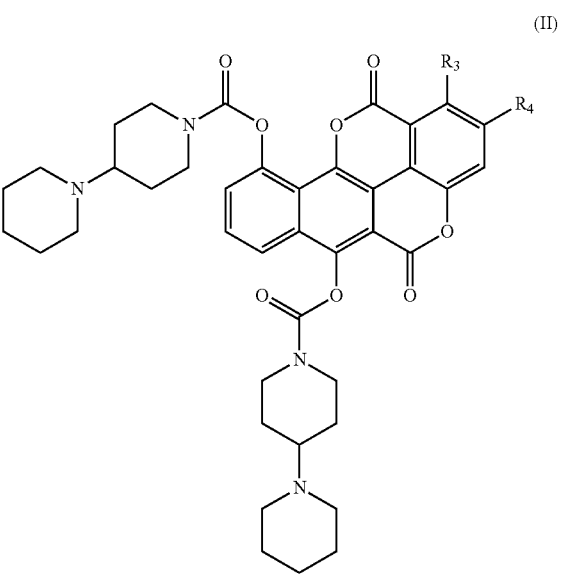

(II)

wherein

R³ is selected from a hydrogen atom, a halogen atom, a hydroxy group, a ($C_1$-$C_8$) alkoxy group, a ($C_1$-$C_8$) alkyl group, a ($C_1$-$C_8$) haloalkyl group, a ($C_2$-$C_8$) alkenyl group, or a ($C_2$-$C_8$) alkynyl group and R⁴ is hydrogen; or R³ is hydrogen and R⁴ is selected from a hydrogen atom, a halogen atom, a hydroxy group, a ($C_1$-$C_8$) alkoxy group, a ($C_1$-$C_8$) alkyl group, a ($C_1$-$C_8$) haloalkyl group, a ($C_2$-$C_8$) alkenyl group, or a ($C_2$-$C_8$) alkynyl group;

or a pharmaceutically acceptable salt, solvate or hydrate or a pharmaceutically acceptable formulation thereof.

Further preferred are compounds of formula (II) wherein R³ and R⁴ are as defined above for compounds of formula (I).

The present invention further provides pharmaceutical compositions comprising one or more compounds of formula (I) or (II) as defined herein or a pharmaceutically acceptable salt, solvate or hydrate thereof, optionally in combination with a pharmaceutically acceptable carrier.

It is a further object of the present invention to provide a compound of formula (I) or (II) as defined herein or a pharmaceutical composition as defined herein for the preparation of a medicament for the treatment of cancer and/or one or more other diseases mentioned herein (e.g. psoriasis and bacterial infections).

The compounds of the present invention are useful in the treatment of different cancers, such as, for example, breast, colon, lung and prostate tumors, as well as osteosarcoma, acute myeloid leukaemia, sporadic endometrial cancer, melanoma, malignant melanoma, soft tissue Sarcoma, B-cell chronic lymphocytic leukaemia, gastric cancers, cervical cancer, hepatocellular carcinoma, pancreatic cancer; renal cancer/kidney cancer and colorectal cancer, bladder cancer, esophageal cancer as well as cancers of glioblastoma multiforme as Well as all other endoscopic accessible areas; and in the treatment of psoriasis; and in the treatment of bacterial infections (such as infections caused by mycobacteria).

Examples of pharmacologically acceptable salts of sufficiently basic compounds of formula (I) or (II) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula (I) or (II) may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of compounds of formula (I) or (II). Compounds of formula (I) or (II) may be solvated, especially hydrated. The hydratization/hydration may occur during the process of production or as a consequence of the hygroscopic nature of the initially water free compounds of formula (I) or (II). The solvates and/or hydrates may e.g. be present in solid or liquid form.

It should be appreciated that certain compounds of formula (I) or (II) may have tautomeric forms from which only one might be specifically mentioned or depicted in the following description, different geometrical isomers (which are usually denoted as cis/trans isomers or more generally as (E) and (Z) isomers) or different optical isomers e.g. as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of formula (I) or (II) may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

The therapeutic use of compounds according to formula (I) or (II), their pharmacologically acceptable salts, solvates and hydrates, respectively, as well as formulations and pharmaceutical compositions also lie within the scope of the present invention.

The pharmaceutical compositions according to the present invention comprise at least one compound of formula (I) or (II) and, optionally, carrier substances and/or adjuvants.

As mentioned above, therapeutically useful agents that contain compounds of formula (I) or (II), their solvates, salts or formulations are also comprised in the scope of the present invention. In general, compounds of formula (I) or (II) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 1 mg to about 10,000 mg, preferably from about 5 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

Compounds of formula (I) can e.g. be prepared by biosynthesis employing anthracyclin starter unit genes. The methyl substituent at C-1 represents the methyl group of the acetyl starter unit of the cha polyketide synthase (PKS) (Xu, Z., Jakobi, K., Welzel, K. & Hertweck, C. Biosynthesis of the antitumor agent chartreusin involves the oxidative rearrangement of an anthracyclic polyketide. *Chem. Biol.* 12, 579-588 (2005)). It has been found that it is possible to exchange the chartreusin methyl substituent for another substituent (e.g. an ethyl substituent) by swapping the anthracycline precursors.

Alternatively, compounds of formula (I) may be prepared synthetically using e.g. the reaction sequence shown in Scheme 1:

Scheme 1: Synthesis of chartarin (1b) and its derivatives norchartarin (13), 1-bromochartarin (14) and 1-vinylchartarin (15).

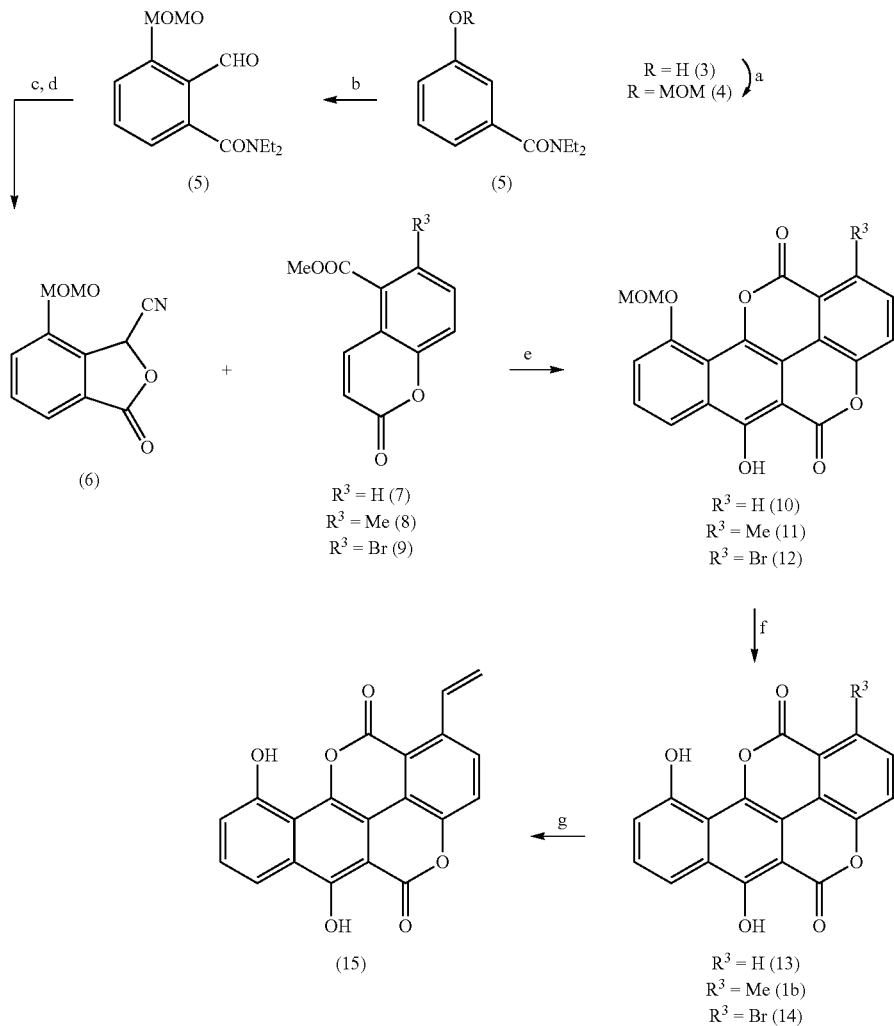

a) MOM-Cl, DIPEA, CH$_2$Cl$_2$, 65%;
b) tBuLi, TMEDA, THF, DMF, 71%;
c) TMS-CN, KCN, 18-crown-6, THF;
d) AcOH, 60% (2 steps);
e) tBuOLi, THF, 66-92%;
f) BBr$_3$, CH$_2$Cl$_2$, 93-100%;
g) Pd(dppp)Cl$_2$, LiCl, nBu$_3$Sn-vinyl, DMF 20%.

Compounds 7, 8 and 9 can e.g. be prepared according to the following reaction sequence:

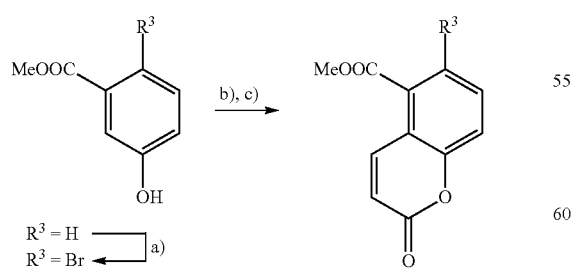

Reagents and conditions:
a) CCl$_4$, Br$_2$, 5 h, rt, 57%;
b) TFA, hexamethylenetetramine, 5-15 min, 120° C., 29-48%;
c) DMA, Ph$_3$P=CH—COOMe, 20 min, reflux, 83%

Further, compounds of formula (I) may be prepared synthetically using e.g. the reaction sequence shown in Scheme 2:

Patra, A. & Roy, H. Convergent and rapid assembly of benzonaphthopyranone cores of chartreusin, chrymutasins and hayumicins. *Tetrahedron Lett.* 45, 7895-7898 (2004)).

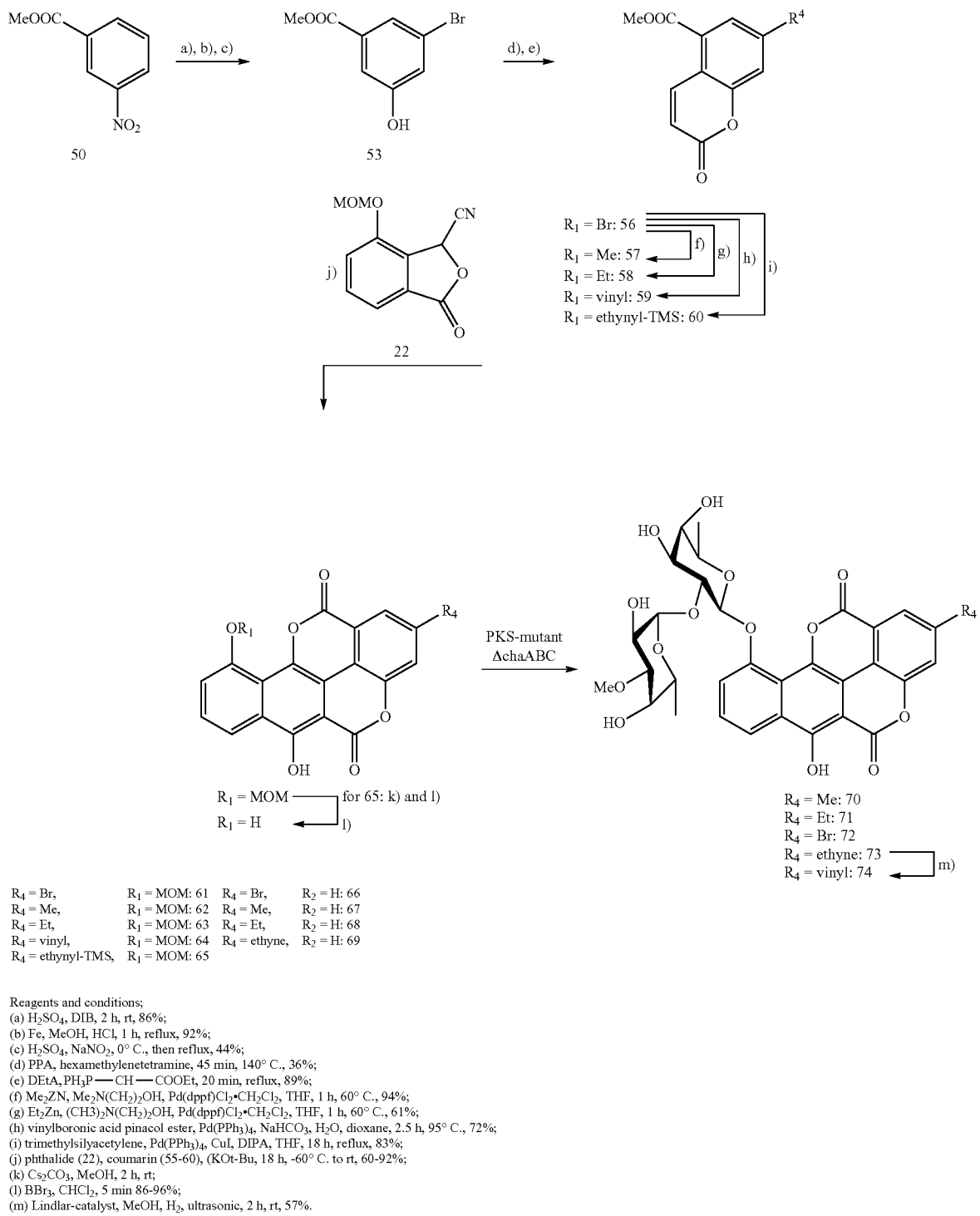

Reagents and conditions;
(a) H$_2$SO$_4$, DIB, 2 h, rt, 86%;
(b) Fe, MeOH, HCl, 1 h, reflux, 92%;
(c) H$_2$SO$_4$, NaNO$_2$, 0° C., then reflux, 44%;
(d) PPA, hexamethylenetetramine, 45 min, 140° C., 36%;
(e) DEtA, PH$_3$P—CH—COOEt, 20 min, reflux, 89%;
(f) Me$_2$ZN, Me$_2$N(CH$_2$)$_2$OH, Pd(dppf)Cl$_2$·CH$_2$Cl$_2$, THF, 1 h, 60° C., 94%;
(g) Et$_2$Zn, (CH3)$_2$N(CH$_2$)$_2$OH, Pd(dppf)Cl$_2$·CH$_2$Cl$_2$, THF, 1 h, 60° C., 61%;
(h) vinylboronic acid pinacol ester, Pd(PPh$_3$)$_4$, NaHCO$_3$, H$_2$O, dioxane, 2.5 h, 95° C., 72%;
(i) trimethylsilyacetylene, Pd(PPh$_3$)$_4$, CuI, DIPA, THF, 18 h, reflux, 83%;
(j) phthalide (22), coumarin (55-60), (KOt-Bu, 18 h, -60° C. to rt, 60-92%;
(k) Cs$_2$CO$_3$, MeOH, 2 h, rt;
(l) BBr$_3$, CHCl$_2$, 5 min 86-96%;
(m) Lindlar-catalyst, MeOH, H$_2$, ultrasonic, 2 h, rt, 57%.

For the synthesis of chartarin variants a Hauser tandem annulation strategy can be employed, which has proven successful for the synthesis of the native aglycone (Mal, D., Alternatively, the following modified synthetic route can be used: Therein, the methoxy substituent was exchanged for the more readily cleavable methoxymethyl (MOM) ether and also the synthesis of the building blocks employed in the annulation reaction has been streamlined. Specifically, 3-hydroxy benzamide 3 was transformed into the corresponding MOM ether 4, and ortho-directed lithiation-formylation sequence yielded 5. The aldehyde was converted into phthalide 6 in the presence of trimethyl silylcyanide and KCN-18-crown-6, followed by treatment with acetic acid. 10-MOM-protected chartarin 11 was obtained by Hauser annulation of phthalide 6 with coumarin 8 (Mal, D., Patra, A. & Roy, H. Convergent and rapid assembly of benzonaphthopyranone cores of chartreusin, chrymutasins and hayumicins. *Tetrahedron Lett.* 45, 7895-7898 (2004); Harayama, T. et al. Convenient Synthesis of a Simple Coumarin from Salicylaldehyde and Wittig Reagent 0.2. Synthesis of Bromocoumarin and Methoxycarbonylcoumarin. *Chem. Pharm. Bull.* 42, 2170-2173 (1994)) (yield 66%). Finally, the MOM group was rapidly (<5 min) and nearly quantitatively removed using boron tribromide, and pure synthetic chartarin 1b was added to the ΔchaABC mutant (*S. albus*:: pXU41/pXU343). HPLC-MS monitoring of the fermentation broth showed that the exogenously supplied aglycone was incorporated by the mutant and processed by glycosylation to restore chartreusin biosynthesis.

For the synthesis of the desmethyl analogue 13, coumarin 7 was synthesized and subjected to Hauser annulation with phthalide 6. After deprotection, the expected structure of 13 was verified by NMR- and MS techniques. Glycosylation was carried out as described above.

Further, a vinyl residue as a photoreactive group has been introduced into chartreusin. For this purpose, a bromo substituent has been introduced that could be replaced for another functional group at a later stage in the synthesis. Indeed it has been found that bromo-substituted coumarin 9 was a suitable reactant in the Hauser annulation, yielding the desired bromochartarin 14 after deprotection.

Stille-type reactions with $Pd^{II}$ salts in the presence of lithium chloride gave acceptable results for the synthesis of the vinyl-substituted aglycone. Best results (20% yield) were obtained with the bridged $Pd(dppp)Cl_2$ catalyst. Glycosylation was carried out as described above.

Further, compounds of formula (I) may be prepared synthetically using e.g. the reaction sequence shown in Scheme 3:

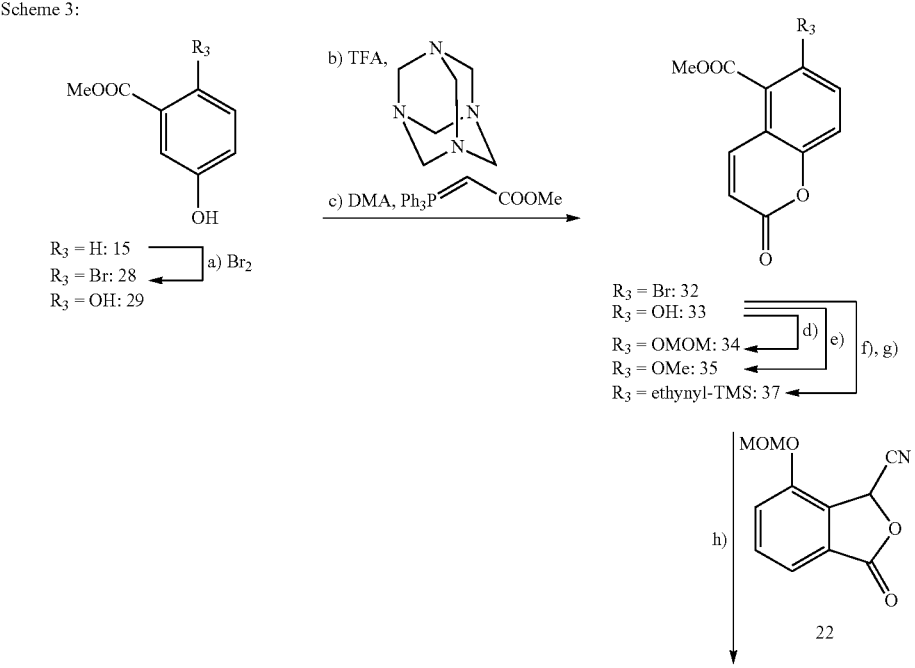

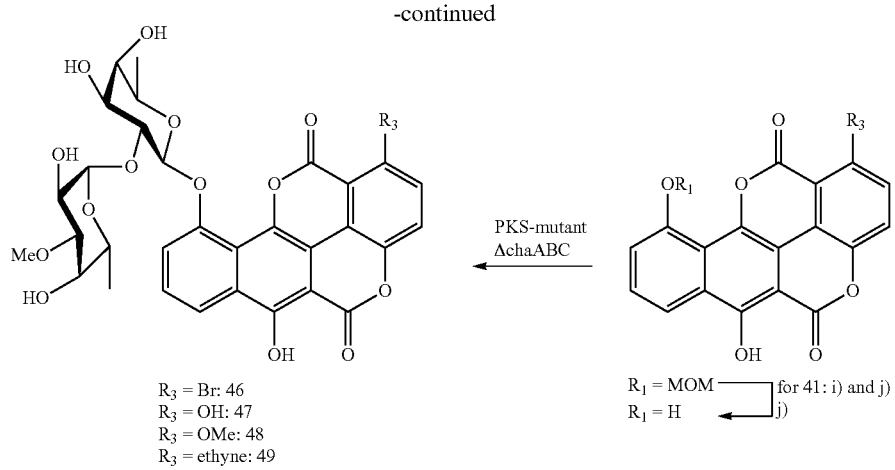

$R_3$ = Br: 46
$R_3$ = OH: 47
$R_3$ = OMe: 48
$R_3$ = ethyne: 49

$R_3$ = Br,        $R_1$ = MOM: 38    $R_3$ = Br,    $R_1$ = H: 42
$R_3$ = OMOM,      $R_1$ = MOM: 39    $R_3$ = OH,    $R_1$ = H: 43
$R_3$ = OMe,       $R_1$ = MOM: 40    $R_3$ = OMe,   $R_1$ = H: 44
$R_3$ = TMS-ethyne, $R_1$ = MOM: 41   $R_3$ = ethyne, $R_1$ = H: 45

Reagents and conditions:
(a) $CCl_4$, $Br_2$, 5 h, rt, 57%;
(b) TFA, hexamethylenetetramine, 5-15 min, 120° C., 29-48%;
(c) DMA, $Ph_3P$=CH—COOMe, 20 min, reflux, 72-83%;
(d) MeI, $K_2CO_3$, DMF, 2 h, rt, 84%;
(e) MOMCl, DIPEA, $CH_2Cl_2$, 2 h, rt, 96%;
(f) $Tf_2O$, DIPEA, $CH_2Cl_2$, 2 h, rt, 78%;
(g) trimethylsilylacetylene, $Pd(PPh_3)_4$, CuI, DIPA, THF, 18 h, reflux, 63%
(h); phthalide (22), coumarin (32, 34, 35 or 37), (KOt-Bu, 18 h, -60° C. to rt, 59-71%;
(i) $Cs_2CO_3$, MeOH, 2 h, rt;
(j) $BBr_3$, $CH_2Cl_2$, 5 min, 98%.

Antimicrobial (MIC value [µM]), cytotoxic ($CC_{50}$ [µM] for HeLa) and antiproliferative ($GI_{50}$ [µM] for HUVEC, K-562, HT-29 and MEL-HO) activities of chartreusin and its derivatives. Test strain: *Mycobacterium vaccae* 10670.

The $GI_{50}$ values of both alkyl-substituted compounds (Chartreusin and Homochartreusin) against HUVEC were similarly low, but marked differences in the cytotoxic activities were found against HeLa cells. As can be seen from this

| | Mycobacterium vaccae | HUVEC | K-562 | HeLa | HT-29 w/o light | HT-29 420 nm, 3 × 8 h | Mel-HO w/o light | Mel-HO 420 nm, 3 × 8 h |
|---|---|---|---|---|---|---|---|---|
| Norchartreusin | 2.5 | 79.8 | 31.6 | 70.7 | | | | |
| Chartreusin | 1.2 | 6.24 | 1.56 | 12.6 | 7.96 | 7.65 | 1.56 | 2.34 |
| Homochartreusin | 9.6 | 7.18 | 2.14 | 23.10 | | | | |
| Vinylchartreusin | 4.8 | 32.8 | 3.06 | 24.7 | 7.05 | 0.61 | 0.11 | 0.08 |
| Bromchartreusin | 8.9 | 65.8 | 8.79 | 48.2 | | | | |
| Ethinylchartreusin | 19.2 | >77 | 64.1 | >77 | 33.2 | 26.9 | | |
| Hydroxychartreusin | 2.4 | 35.0 | 4.82 | 25.5 | | | | |
| Methoxychartreusin | 76 | >76 | >76 | >76 | | | | |
| (1→2)Abeochartreusin | 4.87 | 5.78 | 2.03 | 14.2 | | | | |
| (1→2)Abeohomochartreusin | 19.1 | 26.6 | 11.6 | 58.1 | | | | |
| (1→2)Abeovinylchartreusin | 19.2 | 16.9 | 4.90 | 33.7 | 9.35 | 3.06 | 1.03 | 0.48 |
| (1→2)Abeobromchartreusin | 17.7 | 25.1 | 8.65 | 26.1 | | | | |
| (1→2)Abeo-ethinylchartreusin | 19.2 | 7.84 | 3.23 | 13.4 | 8.61 | 1.69 | 2.00 | 1.38 |
| Chartarin-1,10-bis-1,4'-bipiperidin-1'-carboxylat | >100 | 4.43 | 3.18 | 10.1 | | | | |
| Bromchartarin-1,10-bis-1,4'-bipiperidin-1'-carboxylat | >100 | 10.0 | 9.27 | 20.2 | | | | |
| Norchartarin-1,10-bis-1,4'-bipiperidin 1'-carboxylat | >100 | 52.3 | 52.2 | >71 | | | | |
| Vinylchartarin-1,10-bis-1,4'-bipiperidin-1'-carboxylat | >100 | >68 | >68 | >68 | | | | | data, the compound wherein $R^3$ is an ethyl group therefore shows a higher selectivity.

It has been found that vinylchartreusin shows an extraordinary photoreactivity. Therefore, 1-vinylchartreusin is a strong in vivo drug to form covalent DNA adducts.

In standardized cytotoxic and antiproliferative assays the activity of vinylchartreusin was only slightly lower than chartreusin and homochartreusin using K562 and HeLa tumor cells, but about 4-fold less active than chartreusin using the HUVEC cell line. However, the situation changed substantially under photoinducing conditions. A GaN laser has been used for an induced DNA-adduct assay because a laser warrants high spectral purity combined with a high power density. Furthermore, the emission wavelength (405 nm) fits to the absorption maximum of chartreusin, which is a prerequisite to efficiently activating the molecule.

For the assay defined DNA fragments (1.5 kb) were treated with either chartreusin or 1-vinylchartreusin, and the effect of blue laser irradiation was compared to negative controls incubated in the dark or with daylight.

In the samples containing chartreusin or not irradiated 1-vinylchartreusin as well as negative controls the electrophoretic properties of the DNA fragment could be fully reserved. Irradiated DNA with 1-vinylchartreusin was affected in this manner that a clear band shift to a higher molecular mass is visible. Contrary to this, not irradiated 1-vinylchartreusin shows no shift.

In order to verify the extraordinary in vitro photo induced activity a human foreskin fibroblast cell line (Hs27) has been chosen to evaluate the antiproliferative activity against human cells. During this assay a control group without light has been tested under standard conditions. One group was irradiated with a very homogenous LED cluster under the same conditions. The $GI_{50}$ value for 1-vinylchartreusin without light was 6.8 µg/mL whereas the value with light was more than 10 fold lower (0.5 µg/mL). Native chartreusin was not affected by treatment with light. This indicates the high potential of this new chartreusin-like structure motive as a drug for epithel cell carcinomas. Not only superficial areas like the skin in case of melanoma can be irradiated also endoscopic accessible areas like the bladder, colon, esophageal or laryngeal cancers are conceivable for a treatment.

In addition to the antitumor activity, the chartreusin derivatives also possess strong antibiotic properties including against methicillin-resistant *Staphylococcus aureus* (MRSA) and vancomycin-resistant *Enterococcus* (VRE). 1-Vinyl- and 2-ethynyl-chartreusin are as active as the natural product and are even more potent than the reference antibiotic ciprofloxacin. A similar scenario becomes apparent in case of the VRE assay. Chartreusin, 1-vinyl chartreusin and the compound of formula (I) wherein $R^1$, $R^2$, and $R^4$ are H and $R^3$ is OH are highly active against this strain (MIC 9.59 to 9.76 µM).

Especially preferred are compounds of formula (I) wherein $R^3$ and $R^4$ are both hydrogen atoms for use in the treatment of bacterial infections.

EXAMPLES

Instrumentation

IR spectra were recorded on a Jasco FT/IR 4100 ATR spectrometer. All 1D ($^1H$, $^{13}C$, DEPT) and 2D NMR ($^1H$—$^1H$ COSY, $^1H$—$^{13}C$ HSQC, $^1H$—$^{13}C$ HMBC) have been recorded in deuterated solvents on a Bruker AVANCE II 300, a AVANCE III 500 or 600 MHz instrument equipped with a Bruker Cryo Platform. The chemical shifts are reported in ppm relative to the solvent residual peak (δ $^1H$ (DMSO-$D_6$)=2.50 ppm, δ $^{13}C$ (DMSO-$D_6$)=39.52 ppm, δ $^1H$ (CDCl$_3$)=7.24 ppm, δ $^{13}C$ (CDCl$_3$)=77.23 ppm, δ $^1H$ (CD$_2$Cl$_2$)=5.32 ppm, δ $^{13}C$ (CD$_2$Cl$_2$)=54.00 ppm, δ $^1H$ (pyridine-D$_5$)=7.22 ppm, δ $^{13}C$ (pyridine-D$_5$)=123.87 ppm, δ $^1H$ (D$_3$CCOCD$_3$)=2.05 ppm, δ $^{13}C$ (D$_3$CCOCD$_3$)=29.92 ppm). Following abbreviations are used for multiplicities of resonance signals: s=singlet, d=doublet, t=triplet, q=quartet, br broad. HPLC-MS was performed on a Hewlett Packard Series 1100 system, equipped with a DAD and an electro spray ionization (ESI)-quadrupole mass analyzer. HRESI-MS measurements were conducted either on a Thermo Exactive or a TSQ Quantum Ultra apparatus. Melting points of solid products were studied with a Büchi Melting Point B-540 device and are uncorrected. Gas-chromatographic analytics were executed on a Thermo Trace GC Ultra equipped with Combi PAL auto sampler and coupled with a FID and a Thermo Polaris Q electron impact (EI)-ion trap mass spectrometer. Preparative HPLC was performed on a Gilson 321 Pump with a UVNIS 156 detector system using a Phenomenex column Luna C18, 10 µm, Ø21 mm×250 mm at 21 mL/min and a gradient of water/acetonitrile. Flash chromatography was performed using a CombiFlash® RETRIEVE system by Teledyne Isco (Lincoln, Nebr.) with 120 g RediSep™ silica columns. Analytical HPLC was performed on a Shimadzu HPLC system consisting of an autosampler, high pressure pumps, column oven and PDA. HPLC conditions: C18 column (Grom Sil 100 ODS OAB, 3 µm, 250×4.6 mm) and gradient elution (MeCN/0.1% TFA (H$_2$O) 1/99 in 30 min to MeCN/0.1% TFA (H$_2$O) 100/0, MeCN 100% for 10 min), flow rate 1 mL/min. Preparative HPLC was performed on a Shimadzu LC-8a series HPLC system with UV detector.

General Methods

All reagents were obtained from commercial suppliers (Sigma Aldrich, Acros, TCI, etc.) and used without further purification unless otherwise explained. All solvents used were spectral grade or distilled prior to use. Reactions were carried out under inert gas (Ar) by using the Schlenk technique in dried solvents. Dry N,N' dimethylformamide (DMF) and dichloromethane (DCM) was generated by distillation from calcium hydride suspension. Tetrahydrofurane was pre dried over potassium hydroxide and freshly distilled over lithium aluminum hydride (note: sodium/benzophenone drying was not sufficient enough which resulted in lower yields). Amines were dried over potassium hydroxide and distilled. Methanol, dichloromethane, chloroform and ethyl acetate were distilled prior to use. Open column chromatographic separations were executed on silica gel (Kieselgel 60, 15-40 µm, Merck KGaA). Reaction progresses were monitored by thin layer chromatography (TLC) (silica gel on aluminum sheets with fluorescent dye 254 nm, Merck KGaA), GC-MS or HPLC-MS.

Combinatorial Biosynthesis

Bacterial Strains, Culture Conditions and Molecular Manipulation:

Chartreusin producer *Streptomyces chartreusis* HKI-249 was obtained from the HKI strain collection. For chartreusin and derivatives production, mutant and complementary strains were cultivated in MS medium (mannitol soya flour medium)' for 6 days at 30° C. with shaking. Exconjugants were selected with apramycin (50 µg/mL) and thiostrepton (8 µg/mL) in both solid and liquid medium. *E. coli* strains XL1 blue was served as host for routine subcloning. For intergenic conjugation, *E. coli* ET12567 containing the RP4 derivative pUZ8002 was used. *E. coli* strains grew in LB medium supplemented with ampicillin (100 µg/mL), spectinomycin (100 µg/mL) or apramycin (50 µg/mL) for preservation of plasmids. DNA isolation, plasmid preparation, restriction digests, gel electrophoresis, and ligation reactions were conducted according to standard methods[2]. All the genetic manipulation regarding *Streptomyces* were according to the protocols provided in the handbook Practical *Streptomyces* Genetics[1]. The *E. coli-Streptomyces* shuttle vector pOJ436[3], pKJ55[4] and pWHM4*[5] were used for expression experiments in *Streptomyces*. Restriction enzyme digested DNA fragments and PCR products were recovered from agarose gel by the GFX PCR DNA and Gel Band Purification Kit (Amersham).

Inactivation of Minimal PKS Genes chaABC

The chaABC null mutant was constructed by using the λred system according to the manual of the manufacturers (Plant Bioscience Limited). To amplify the spectinomycin resistance gene (aadA) flanked by FRT sites (FLP recognition targets), two long primers were designed. chaABC-PTL: 5'-TCAATGGGCCGCACTTGTCGGCTCGAGAG-GATTTCCATGATTCCGGGGATCCGTC GACC-3', and chaABC-PTR: 5'-GGCCCCGGCCCGGCTGCCGGGC-CCGGTCCCGCTTCGTCATGTAGGCTGGAGCTGC TTC-3'. The PCR product was introduced into *E. coli* BW25113/pIJ790 containing cosmid pSC5P21 with concomitant substitution of the chaABC gene by the spectinomycin cassette. The inserted cassette was removed through expression of the FLP-recombinase in *E. coli* DH5α_BT340, yielding an 81 bp "scar" in the preferred reading frame. The resulting plasmid, pXU41, was then introduced into *S. albus* by intergenic conjugation with the help of *E. coli* ET12567 containing the RP4 derivative pUZ8002. The exconjugant *S. albus*::pXU41 was selected by its apramycin resistance.

Complementation of chaABC Null Mutant with Both Cha and Akn Genes

A 3.4 kb-FspI-fragment containing chaABC and a 5.5 kb-NruI-fragment with addition of chaR1, respectively, downstream of a constitutive promoter were cloned into *E. coli-Streptomyces* shuttle vector pKJ01[4]. The resultant constructs pXU66 and pXU67 were respectively introduced into the minimal PKS null mutant *S. albus*::pXU41 via intergenic conjugation. For redirecting the biosynthesis of chartreusin, the 5 kb aklavinone synthase genes, aknBCDE$_2$F, were applied to recombine with the retained Cha enzymes. The 5-gene-cassette was installed downstream of a constitutive promoter PermE* on the multi-copy freestanding *E. coli-Streptomyces* shuttle vector pWHM4*. The resultant plasmid pMMK1 carried an operon encode the minimal PKS, consisting of ketosynthase (AknB), chain length factor (AknC), and acyl carrier protein (AknD), followed by the propionate starter unit synthase, the KASIII homolog lacking the active cysteine residue (AknE$_2$), and the acyltransferase homolog (AknF)[6]. This cassette was used to complement the cha PKS-null mutant *S. albus*::pXU41 in parallel with pXU67.

Supplementation of the Transcriptional Activator ChaR1

In order to get higher production of chartreusin and its derivatives, a transcriptional activator encoded by chaR1 was co-expressed with corresponding genes. The fragment containing chaR1 (1.2 kb) was extracted from the cha cluster by a double-digestion of PmlI and StuI. It was then subjected to the EcoRV site of pXU55, which harbours oriT-site for conjugation and a constitutive promoter upstream of the multicloning site. The achieved oriT-promoter-chaR1 cassette was further subcloned into the *E. coli-Streptomyces* shuttle vector pWHM4* derivative, namely pXU343, for co-expression experiments.

[1] T. Kieser, M. J. Bibb, M. J. Buttner, K. F. Chater, D. A. Hopwood, *Practical Streptomyces Genetics*, The John Innes Foundation, Norwich, U.K., 2000.

[2] J. Sambrook, E. F. Fritsch, T. Maniatis, *Molecular Cloning: a Laboratory Manual*, 2nd ed., Cold Spring Harbor, N.Y., 1989.

[3] M. Bierman, R. Logan, K. O'Brien, E. T. Seno, R. N. Rao, B. E. Schoner, *Gene* 1992, 116, 43.

[4] K. Jakobi, C. Hertweck, *J Am Chem Soc* 2004, 126, 2298.

[5] J. Vara, M. Lewandowska-Skarbek, Y. G. Wang, S. Donadio, C. R. Hutchinson, *J Bacteriol* 1989, 171, 5872.

[6] K. Raty, J. Kantola, A. Hautala, J. Hakala, K. Ylihonko, P. Mantsala, *Gene* 2002, 293, 115.

FIG. 1 shows the supplementation of Cha minimal PKS-null mutant *S. albus*::pXU41 (chaABC cassette was replaced by an 81-bp scar) with freestanding chaR1ABC (pXU67) from original cha gene cluster and aknBCDE$_2$F (pMMK1) out of aklavinone biosynthetic genes, respectively. Both constructs complemented the scarce of polyketide backbone of the mutant. The metabolite from each cassette was consequently tailored by Cha post-PKS enzymes to give rise to the authentic chartreusin and novel ethyl-chartreusin, respectively. chaR1ABC code for the *Streptomyces* antibiotic regulatory protein (SARP), ketosynthase (KS), chain length factor (CLF), and acyl carrier protein (ACP), respectively. aknBCDE2F encode the minimal PKS (KS-CLF-ACP), the ketosynthase III homolog (AknE2), and acyltransferase homolog (AknF), which is responsible for the propionate starter unit incorporation.

Culture Material and Fermentation

The strain was stored in 50% glycerol at −20° C. The strain was grown in a suitable Erlenmeyer flask with J Medium (tryptone, 30 g; sucrose, 100 g; yeast extract, 10.0 g; and MgCl$_2$.6H$_2$O, 10.0 g, in 1.0 L distilled water) for 24 hrs at 28° C. One volume of this culture was used to inoculate 20 volumes containing Medium 10 (yeast extract, 4.0 g; malt extract, 10.0 g; glucose, 4.0 g in 1.0 L distilled water). The cultures were shaken on a rotary shaker (180 rpm) at 28° C. for 1 day. Then the 0.08 volumes of substrate solution (1 mg/mL substrate in DMSO) were added and the cultures were shaken on a rotary shaker (180 rpm) at 28° C. for 1 day.

If the fermentation was carried out in a fermenter the culture was held at a pH range of 6.5-7.5. All media were treated with apramycin and thiostreptone to a final concentration of 50 µg/mL and 15 µg/mL respectively.

Extraction and Isolation

The fermentation liquid was extracted three times with each the double volume of ethyl acetate. The solvent was removed and the crude extract was suspected to sephadex LH20 chromatography using chloroform/methanol 1:1 and silica gel column with a gradient from 100% chloroform to chloroform/methanol 9:1. The product was then ~90% pure (HPLC). At this stage the yellow solid was washed twice with DCM and dried to yield the pure product. The DCM solution was dried and suspected to preparative HPLC to yield the total fermentation amount.

Isolation of Homochartreusin:

The entire fermentation broth was extracted with ethyl acetate and the combined extracts were concentrated under reduced pressure. The crude extract was separated by flash chromatography on silica gel using CHCl$_3$/MeOH mixtures of increasing polarity as eluents (CHCl$_3$:MeOH 98:2, CHCl$_3$:MeOH 95:5, CHCl$_3$:MeOH 90:10, CHCl$_3$:MeOH 80:20) and a flow rate of 30 mL·min$^{-1}$. Metabolite-containing fractions were further purified by preparative HPLC (column: Nucleosil 100-5 250×20, gradient mode with MeCN/0.1% TFA (H₂O): 1% MeCN to 83% MeCN in 30 min, then 83% MeCN for 10 min, flow rate 12 mL·min⁻¹).

Gel Electrophoresis with a Specified DNA Fragment

DNA-Adduct formation was carried out using a pure specified DNA fragment with the following sequence:

```
ccaaggatccaccttggctcacacaaaatattaccaacgacttgctaccatcggccttcactatggaccggctttccagtgccttagcgg gaatgtggagtgtggtaaaggcttcgcaactggagaaatcacctgggagcctaagagggtttccactggtgatgactccagcgccagt gtgcttcatcctaccttcttggattcctcctccacccaatcttcgctgcagtggaaggtctcatgggcacagtattacggagtcctttatc cctactttcatgcgctctttgaaaatttctggtcttcttaaccgtaaggagtacaaatgcgatggattcaaggccaacgttgctgtcgacagc tggatgcacggacccgtgttgccattagcaatattggtattgagtccaaggagggccagcttcttgcggatattgaaggtctagaactc accagccttggaagcgatgctgatgaccagcagaagagaactcttttcttcggcatccagtggaagccggctttcgagttcctgactcct gctcaagcccagaacctcagcgtccctgagattgttgacctctacgtccaccagaaccctaatttgcacttccttcactactctgactccca tacctctaccttggacatcctgaaccatcttggtggctctaatggagagaggcgcaaattcggcaaaatgactgtggtgccagttggttca gcggaggaggcaagcttctctcccctttgttgaacgctggaatggccttgtttcgctcgaggtcactcttgatgagaagtttgatgtgataat aatctcctcttcagctgaagctgcttccattgagaatctccatgagaacggccttgttatatcccatcctgcaaaggctcccactgccgaca accttagacaattatgggccacttcggatgtggccgtcttgaagggcggtgatgaatcagtgttcactcctgagactcttaccattctcatg ccatctaatccatctacagagactgaagctctcgccaaaagaattgaatcgaccacctcagcaaaggttactagaaaagacttcctgtct ctcagaaatggcacacgaatggacgacaatgttatttctctctacgccctcgatgtaaacatcttctacgatgagccatccaaggctttga acgaattcaaggcagtccagtccctcacaagcgatgcaaaccgcaacattgtttggcttagccagggtaccttcatggattgccctgcc cagagcaagctatgttcccaggccttgctcgctctgttcgtcatgaaactgaagacttgagaattgcaattcttgatataactaagtctgcta aagctgatctctctgccgatctcattctccgcatcctcaacccaaccctccatgaagaagaaattgcgcttcgaaatggccaaatccatgt ctcccgattgcacgcaaatgatgagttgaactctaagattgccggaggctacggatccttgg
```
35

Figure 2:
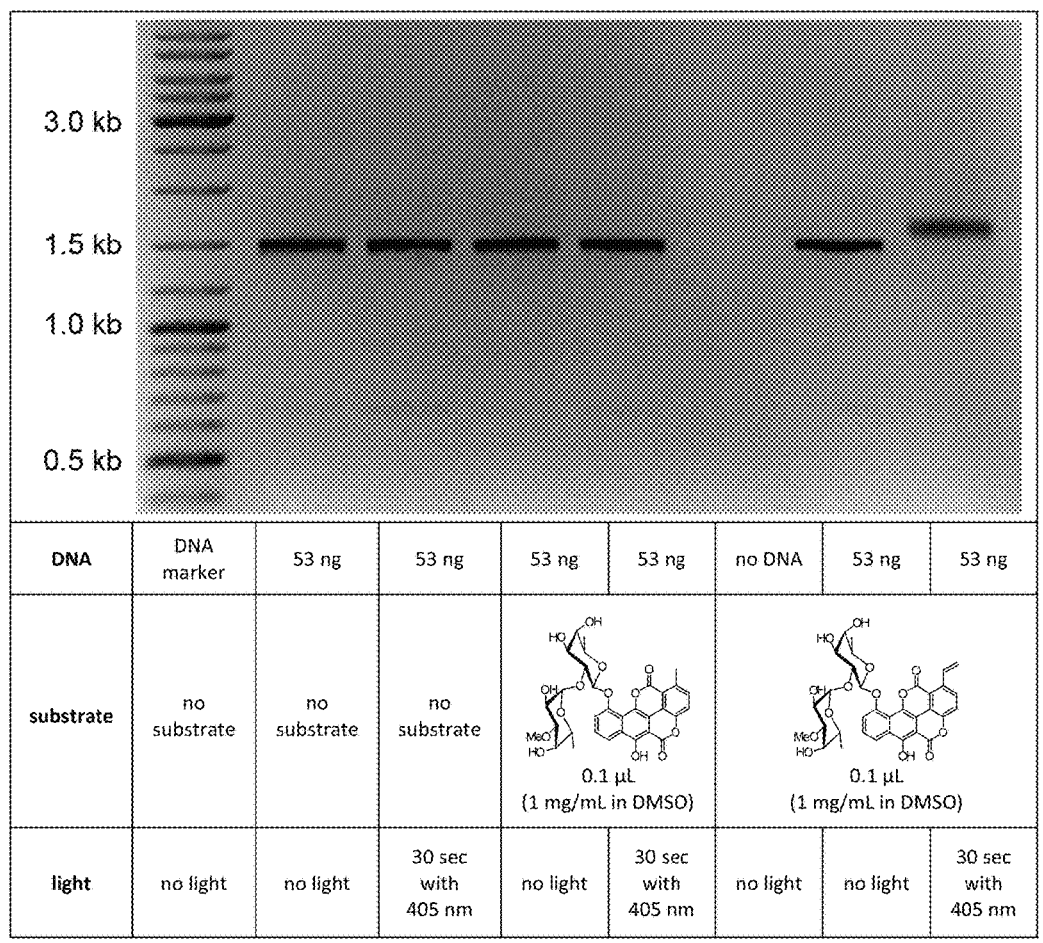
Figure 7:
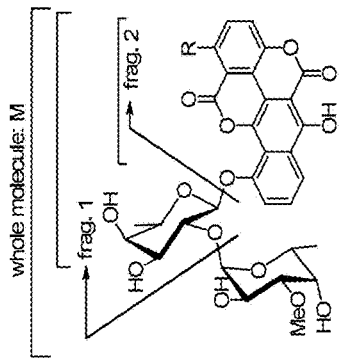
Figure 8:
Figure 16:
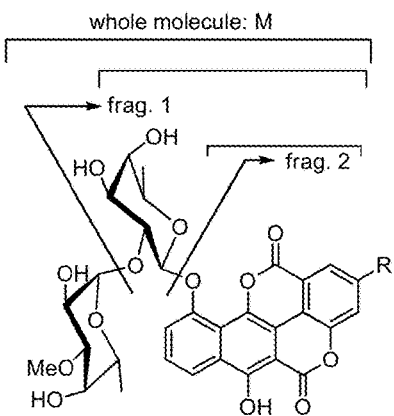

8 µL of water, 2 µL of DNA (25.7 ng/µL) were either directly treated with 2 µL loading buffer or were treated additionally with 0.1 µL (1 mg/mL in DMSO) substrate. The solution was irradiated with a laser (405 nm, 20 mW) for 30 sec. and then treated with loading buffer. The DNA was loaded on 1% agarose gel with ethidium bromide operating at 120 V (FIG. 2).

Chemical Synthesis and Analytical Data

N,N-diethyl-3-(methoxymethoxy)benzamide (4)

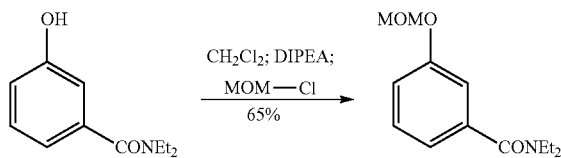

10 g (51.8 mmol, 1 eq.) N,N-diethyl-3-hydroxybenzamide (3) were placed in a round bottom flask and dissolved in 160 mL dichloromethane. Then 9.7 mL, (56.9 mmol, 1.1 eq.) Diisoproyl amine (DIPEA) and 4.13 mL (54.4 mmol, 1.05 eq.) methoxy methylchloride were added and the reaction flask was equipped with a drying tube filed with blue gel. The solution was stirred for 18 h at RT. Then additional 0.79 mL (10.36 mmol, 0.2 eq.) methoxy methylchloride were added and the solution was stirred for further 24 h at RT until no changes in GC/MS could be observed.

The solvent was removed under reduced pressure and the resulting oil was distilled at 2 mbar. The fraction from 156-158° C. was collected to yield 8.15 g (35.9 mmol, 69%) of the desired product as a clear oil.

$R_f$ silica gel 60; cyclohexane/ethyl acetate 2:1=0.25
bp. 156-158° C. at 2 mbar.

$^1$H NMR (300 MHz; CDCl₃): δ=7.30-7.25 [m, 1H, Ar—CH—CH—CH]; 7.04-7.01 [m, 2H, Ar—CH—COMOM-CH]; 6.98-3.95 [m, 1H, Ar—CH—CH—CCONEt₂]; 5.15 [s, 2H; OCH₂O]; 3.50 [br s, 2H, NCH'₂]; 3.44 [s, 3H, OCH₃]; 3.22 [br s, 2H, NCH₂]; 1.21 [br s, 3H, NCH₂CH'₃]; 1.09 [br s, 3H, NCH₂CH₃] ppm.

$^{13}$C NMR (75 MHz; CDCl₃): δ=170.8 (CONEt₂); 157.1 (Ar—COMOM); 138.5 (Ar-CCONEt₂); 129.5 (Ar—CH—CH—CH—CCONEt₂); 119.6 (Ar—CH—CH—CH—CCONEt₂); 116.9 (Ar—CH—CH—CH—CCONEt₂); 114.1 (Ar—COMOM-CH—CCONEt₂); 94.4 (OCH₂O); 55.9 (OCH₃); 43.2 (NCH'₂CH'₃); 39.1 (NCH₂CH₃); 14.1 (NCH'₂CH'₃); 12.8 (NCH₂CH₃) ppm.

IR (ATR): ṽ ($T_{rel}$)=3494 (w), 3247 (w), 3065 (w), 2971 (m), 2934 (m), 2900 (m), 2849 (w), 2826 (w), 2789 (w), 2069 (w), 2000 (w), 1928 (w), 1627 (s), 1578 (s), 1489 (m), 1470 (s), 1456 (s), 1437 (s), 1424 (s), 1381 (m), 1364 (m), 1349 (m), 1315 (m), 1288 (s), 1237 (s), 1219 (m), 1206 (m), 1150 (s), 1099 (s), 1078 (s), 1014 (s), 1006 (s), 987 (s), 944 (m), 922 (s), 905 (m), 879 (m), 824 (m), 793 (s), 751 (s), 706 (m), 688 (m), 667 (m) cm⁻¹.

EI-MS (EI+, 70 eV): m/z=237 (30) [M]·⁺, 236 (49), 192 (100), 165 (62), 164 (39), 135 (15), 121 (8), 107 (9), 77 (10).

ESI-MS (ESI+): m/z=238 (100) [M+H]⁻, 260 (21) [M+Na]⁺, 475 (25) [2M+H]⁺, 497 (68) [2M+Na]⁺ amu.

HRMS (ESI+) 238.1438 for C₁₁H₈NO₄ [M+H]⁺; 238.1439 found.

N,N-diethyl-2-formyl-3-(methoxymethoxy)benzamide (5)

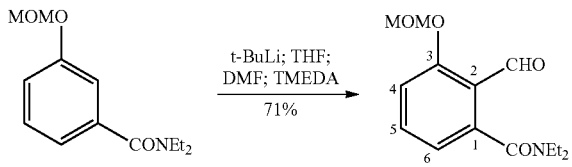

549 mg (2.31 mmol, 1 eq.) N,N-diethyl-3-(methoxymethoxy)benzamide (4) were placed in a Schlenk tube evacuated and flushed with argon 3 times. Then 3.7 mL freshly prepared dry THF and 384 µL, (2.55 mmol, 1.1 eq.) N,N,N',N'-tetramethyl-ethane-1,2-diamine (TMEDA) were added and the clear, colorless solution was cooled to −78° C. in an ethanol/dry ice bath. After temperature equilibration (5 min) 1.1 eq. of tert-butyl lithium solution (1.7 mol/L in pentane) were added with a syringe pump with 1 mL/min. After 45 min 590 µL (7.64 mmol, 3.3 eq.) DMF were added as with a syringe pump at 0.7 mL/min. The yellow solution was allowed to warm to RT overnight. The solution was then quenched with water and extracted 3 times with diethyl ether. The solvent was removed in vacuo and the resulting suspension was suspected to column chromatography with cyclohexane/ethyl acetate 2:1 to yield 436 mg (1.65 mmol, 71%) of the desired product as a pale yellow oil.

$R_f$ silica gel 60; cyclohexane/ethyl acetate 2:1=0.06
$^1$H NMR (300 MHz; CDCl$_3$): δ=10.47 [s, 1H, CHO]; 7.48 [m, 1H, Ar—CH-5]; 7.19 [d, 1H, $^3J_{H-H}$=8.4 Hz, Ar—CH-4]; 6.85 [d, 1H, $^3J_{H-H}$=7.4 Hz, Ar—CH-6]; 5.27 [s, 2H, OCH$_2$O]; 3.54 [q, 2H, $^3J_{H-H}$=7.1 Hz, NCH$_2$CH$_3$]; 3.04 [q, 2H, $^3J_{H-H}$=7.1 Hz, NCH$_2$'CH$_3$']; 1.28 [t, 3H, $^3J_{H-H}$=7.1 Hz, NCH$_2$CH$_3$]; 0.98 [t, 3H, $^3J_{H-H}$=7.1 Hz, NCH$_2$'CH$_3$'] ppm.
$^{13}$C NMR (75 MHz; CDCl$_3$): δ=189.2 (CHO); 169.6 (CON); 159.9 (Ar—C-3); 139.2 (Ar—C-1); 135.4 (Ar—CH-5); 121.8 (Ar—C-2); 120.1 (Ar—CH-6); 115.0 (Ar—CH-4); 94.7 (OCH$_2$O); 56.5 (OCH$_3$); 42.4 (NCH$_2$CH$_3$); 38.6 (NCH$_2$'CH$_3$'); 13.5 (NCH$_2$CH$_3$); 12.0 (NCH$_2$'CH$_3$') ppm.
ESI-MS (ESI+): m/z=266 (35) [M+H]$^+$, 288 (100) [M+Na]$^+$, 320 (36) [M+Na+MeOH]$^+$, 531 (12) [2M+H]$^+$553 (54) [2M+Na]$^+$, 585 (14) [2M+Na+MeOH]$^+$. (ESI+) with NH$_4$OAc: m/z=266 (100) [M+H]$^+$, 531 (60) [2M+H]$^+$.
HRMS (ESI+) for C$_{14}$H$_{20}$NO$_4$ [M+H]$^+$ 266.1387. found. 266.1375.

7-(methoxymethoxy)-3-oxo-1,3-dihydroisobenzofuran-1-carbonitrile (6)

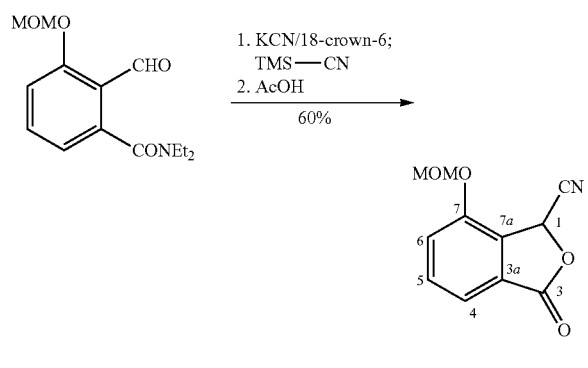

418 mg (1.6 mmol, 1 eq.) N,N-diethyl-3-(methoxymethoxy)benzamide (5) were dissolved in 6.3 mL dichloro methane and treated with 1.6 mL (31.5 µmol, 0.02 eq.) of a 20 mmol/L potassium cyanide/18-crown-6 solution in THF and cooled to 0° C. Then 296 µL (2.4 mmol, 1.5 eq.) trimethylsilyl cyanide were added and the solution was stirred for 30 min at 0° C. The solvent was removed under reduced pressure and then 6.3 mL glacial acetic acid were added and the solution was stirred at RT over night. The clear solution was poured into 100 mL saturated sodium bicarbonate solution and extracted three times with each 100 mL ethyl acetate. The combined organics were washed with saturated sodium bicarbonate solution, brine solution and dried over sodium sulfate. After filtration the solvent was removed and the crude product was recrystallized from cyclohexane to yield 273 mg (1.2 mmol, 79%) 7-(methoxymethoxy)-3-oxo-1,3-dihydroisobenzofuran-1-carbonitrile (6) as a white crystalline powder.

$R_f$ silicagel 60; chloroform/methanol 95:5=0.91
mp. 126.9° C.
$^1$H NMR (300 MHz; D$_3$CCOCD$_3$): δ=7.75 [m, 1H, Ar—CH-5]; 7.61 [dd, 1H, $^3J_{H-H}$=8.5 Hz, $^4J_{H-H}$=0.5 Hz, Ar—CH-6]; 7.58 [dd, 1H, $^3J_{H-H}$=7.5 Hz, $^4J_{H-H}$=0.5 Hz, Ar—CH-4]; 6.58 [s, 1H, CHCN]; 5.52 [d, 1H, $^2J_{H-H}$=6.9 Hz, OCH$_2$O]; 5.45 [d, 1H, $^2J_{H-H}$=6.9 Hz, OCH$_2$O], 3.52 [s, 3H, OCH$_3$] ppm.
$^{13}$C NMR (75 MHz; D$_3$CCOCD$_3$): δ=168.4 (CO-3); 153.0 (Ar—C-4); 134.2 (Ar—CH-5); 131.5 (Ar—C-7a); 127.1 (Ar—C-3a); 120.9 (Ar—CH-6); 119.2 (Ar—CH-4); 114.9 (CN); 95.3 (OCH$_2$O); 65.3 (CHCN); 56.8 (OCH$_3$) ppm.
IR (ATR) $\tilde{v}$ (T$_{rel}$)=3093 (w), 3023 (w), 2973 (w), 2939 (w), 2852 (w), 2832 (w), 2529 (w), 2342 (w), 2191 (w), 2165 (w), 2068 (w), 2009 (w), 1957 (w), 1771 (s), 1737 (m), 1617 (m), 1486 (m), 1442 (m), 1404 (w), 1308 (m), 1281 (m), 1265 (s), 1255 (s), 1204 (m), 1173 (m), 1156 (s), 1088 (m), 1072 (m), 1055 (m), 1021 (m), 986 (s), 957 (s), 917 (s), 890 (s), 854 (m), 809 (m), 779 (m), 757 (s), 747 (s), 686 (m), 667 (m) cm$^{-1}$.
EI-MS (EI+, 70 eV): m/z=219 (9) [M]$^{•+}$, 189 (23), 188 (24), 160 (13), 148 (27), 133 (21), 120 (91), 105 (16), 92 (60), 75 (91), 63 (100).
ESI-MS (ESI−): m/z=218 (100) [M−H]$^−$ amu.
ESI-MS$^2$ (ESI−): m/z=218 (15) [M−H]$^−$; 173 (100); 117 (12) amu.
HRMS (ESI−) for C$_{11}$H$_8$N$_4$O [M−H]$^−$ 218.0459. found. 218.0419 amu.

General Procedure for Annulation:
1.0 eq. 7-(methoxymethoxy)-3-oxo-1,3-dihydroisobenzofuran-1-carbonitrile was weighed into a Schlenk flask, evacuated and flushed with argon 3 times. Then freshly prepared dry THF was added and the clear, colorless solution was cooled to −60° C. in an ethanol/dry ice bath. After equilibration (5 min) 3 eq. of lithium tert-butoxide solution (1 mol/L in THF) were added with a syringe pump with 12 mL/min. After 45 min the coumarin was added as solution in THF again with a syringe pump at 12 mL/min. After additional 1 h at −60° C. the deep yellow-orange solution was allowed to warm to RT over night. The solution was then treated with 10% (m/v) ammonium chloride solution and stirred vigorously for 30 min at RT. The THF was removed in vacuo and the resulting suspension was filtered. The filter cake was washed with water, acetone and pentane/ether 1:1 and then dried overnight in fine vacuum to yield the pure product as a yellow powder.

General Procedure for MOM-Deprotection:

The MOM protected phenol was weighed into a two necked round-bottom flask, evacuated and flushed 3 times with argon. The solid was dissolved in the minimal necessary amount of dry methylene chloride (about 1 mL per 1 mg of substrate) and treated with 5 eq. of a solution of boron tribromide in methylene chloride (1 mol/L). Immediately the yellow solution changed from yellow to red-orange. After 5 min a saturated sodium bicarbonate solution was added (25% (v/v) of total solvent volume) where the solution changed to yellow and a yellow precipitate occurs. The methylene chloride was removed in vacuo and the resulting suspension was filtered. The filter cake was washed with water, acetone and pentane/ether 1:1 and then dried overnight in fine vacuum to yield the pure phenol as yellow powder.

10-MOM-norchartarin (10)

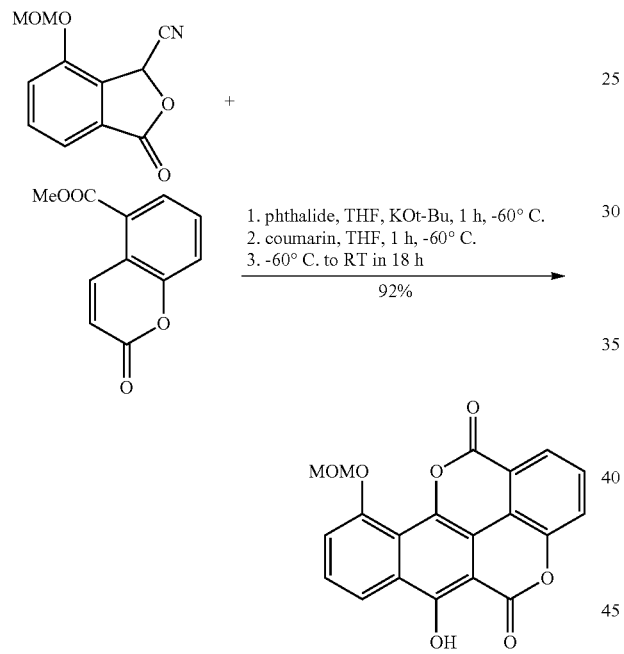

This compound was prepared as a yellow solid in (92)% yield by the reaction between (6) and (7) according to the general procedure for annulation as described.

$R_f$ silicagel 60; chloroform/methanol 95:5=0.91 mp. 234.5° C.

$^1$H NMR (600 MHz; CD$_2$Cl$_2$): see Table 3.

$^{13}$C NMR (150 MHz; CD$_2$Cl$_2$): see Table 4.

IR (ATR): ṽ (% T)=3220 (w), 3096 (w), 3056 (w), 2981 (w), 2839 (w), 1733 (s), 1712 (s), 1611 (m), 1577 (w), 1550 (w), 1510 (m), 1496 (s), 1469 (m), 1442 (m), 1402 (m), 1378 (m), 1335 (m), 1281 (m), 1264 (m), 1240 (s), 1206 (s), 1153 (m), 1108 (s), 1081 (s), 1069 (s), 1017 (s), 986 (m), 941 (m), 930 (m), 905 (m), 875 (m), 819 (m), 778 (m), 761 (s), 743 (s), 707 (w), 685 (w), 668 (w), 659 (m) cm$^{-1}$.

ESI-MS (ESI-): m/z=363 (100) [M-H]$^-$.

HRMS (ESI-) for C$_{20}$H$_{11}$O$_7$ [M-H]$^-$ 363.0510. found. 363.0513 amu.

10-MOM-1-bromochartarin (12)

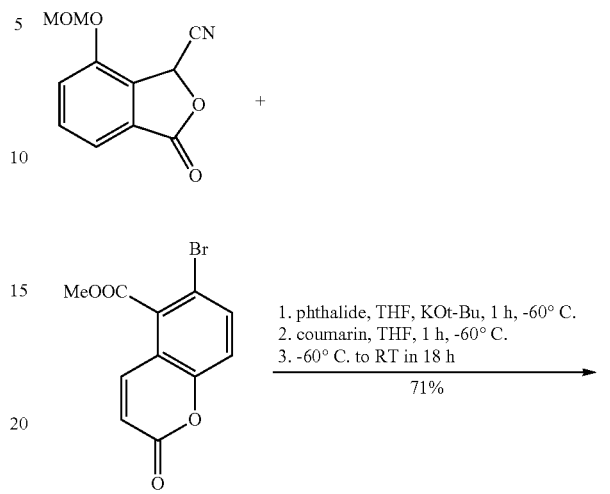

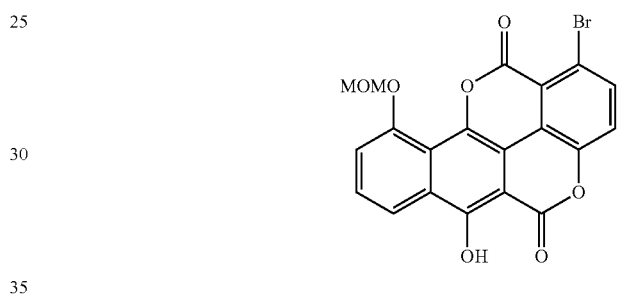

This compound was prepared as a yellow solid in (71)% yield by the reaction between (6) and (9) according to the general procedure for annulation as described.

$R_f$ silicagel 60; chloroform/methanol 95:5=0.93 mp. 290.4° C.

$^1$H NMR (600 MHz; CD$_2$Cl$_2$): see Table 3.

$^{13}$C NMR (150 MHz; CD$_2$Cl$_2$): see Table 4.

IR (ATR): ṽ (% T)=3095 (w), 3008 (w), 2827 (w), 1739 (s), 1691 (s), 1633 (w), 1605 (m), 1588 (m), 1497 (m), 1463 (m), 1441 (m), 1395 (m), 1370 (s), 1342 (m), 1322 (m), 1310 (m), 1276 (m), 1252 (m), 1237 (s), 1211 (m), 1160 (s), 1140 (s), 1111 (m), 1091 (s), 1066 (s), 1010 (s), 924 (s), 873 (m), 836 (m), 816 (m), 788 (m), 774 (s), 720 (m), 702 (m), 685 (m), 677 (w), 660 (m) cm$^{-1}$.

HRMS (ESI-) for C$_{20}$H$_{10}$O$_7$$^{79}$Br [M-H]$^-$ 440.9615. found. 440.9620 amu.

10-MOM-chartarin (11)

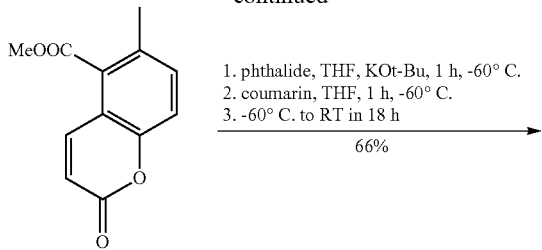

1. phthalide, THF, KOt-Bu, 1 h, -60° C.
2. coumarin, THF, 1 h, -60° C.
3. -60° C. to RT in 18 h

66%

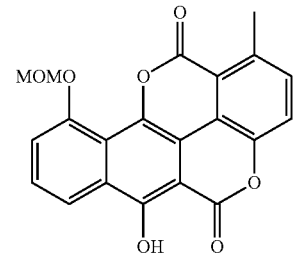

This compound was prepared as a yellow solid in (66)% yield by the reaction between (6) and (8) according to the general procedure for annulation as described.

$R_f$ silicagel 60; chloroform/methanol 95:5=0.91 mp. 273.1° C.

$^1$H NMR (500 MHz; $CD_2Cl_2$): see Table 3.

$^{13}$C NMR (125 MHz; $CD_2Cl_2$): see Table 4.

IR (ATR): $\tilde{v}$ (% T)=3078 (w), 2928 (w), 1727 (s), 1635 (w), 1588 (m), 1474 (w), 1397 (m), 1345 (m), 1255 (s), 1209 (m), 1143 (s), 1103 (m), 1065 (s), 933 (s), 832 (m), 794 (m), 724 (m), 661 (m), 2970 (w), 2831 (w), 1683 (m), 1609 (m), 1502 (m), 1448 (m), 1371 (s), 1316 (m), 1236 (s), 1155 (s), 1124 (m), 1083 (m), 1017 (s), 875 (m), 813 (m), 775 (s), 687 (w) cm$^{-1}$.

ESI-MS (ESI-): m/z=377 (100) [M-H]$^-$.

HRMS (ESI-) for $C_{21}H_{13}O_7$ [M-H]$^-$ 377.0667. found. 377.0666 amu.

Chartarin (1 b)

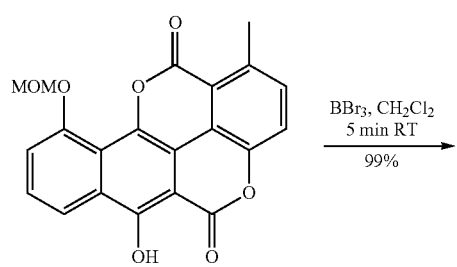

This compound was prepared as a yellow solid in (99)% yield by the reaction of (11) according to the general procedure for MOM-deprotection as described.

$R_f$ silicagel 60; chloroform/methanol 95:5=0.91 mp. 306.5° C.

$^1$H NMR (500 MHz; pyridine-$D_5$): see Table 1.

$^{13}$C NMR (125 MHz; pyridine-$D_5$): see Table 2.

IR (ATR): $\tilde{v}$ (% T)=3055 (w), 2929 (w), 1688 (s), 1607 (m), 1534 (w), 1457 (w), 1392 (m), 1331 (m), 1290 (m), 1236 (m), 1180 (m), 1117 (m), 1036 (m), 971 (w), 943 (w), 882 (w), 815 (m), 722 (m), 687 (m), 3213 (w), 2968 (w), 1740 (w), 1636 (m), 1582 (m), 1505 (m), 1421 (m), 1371 (s), 1316 (m), 1254 (m), 1219 (s), 1149 (m), 1072 (m), 985 (m), 961 (m), 890 (w), 841 (m), 776 (s), 712 (m), 662 (m) cm$^{-1}$.

HRMS (ESI-) for $C_{19}H_9O_6$ [M-H]$^-$ 333.0410. found. 333.0405 amu.

Norchartarin (13)

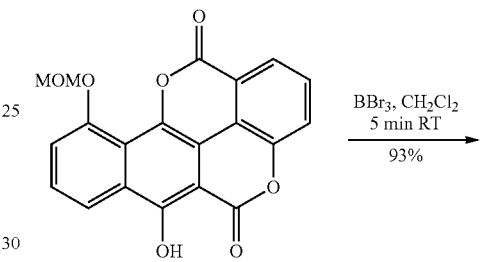

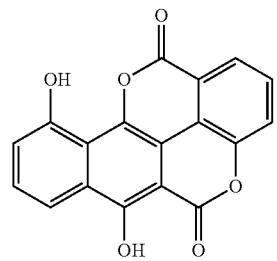

This compound was prepared as a yellow solid in (93)% yield by the reaction of (10) according to the general procedure for MOM-deprotection as described.

$R_f$ silicagel 60; chloroform/methanol 95:5=0.89 mp. 329.9° C.

$^1$H NMR (600 MHz; pyridine-$D_5$): see Table 1.

$^{13}$C NMR (150 MHz; pyridine-$D_5$): see Table 2.

IR (ATR): $\tilde{v}$ (% T)=3206 (m), 1685 (s), 1617 (m), 1578 (m), 1507 (m), 1462 (w), 1368 (m), 1329 (m), 1264 (m), 1227 (m), 1144 (m), 1090 (s), 1022 (m), 977 (s), 913 (m), 879 (m), 811 (m), 747 (s), 678 (s), 1703 (m), 1634 (w), 1590 (w), 1534 (w), 1474 (m), 1421 (m), 1341 (m), 1288 (m), 1242 (m), 1202 (s), 1119 (s), 1061 (m), 997 (m), 929 (m), 903 (m), 827 (m), 773 (m), 711 (s) cm$^{-1}$.

HRMS (ESI-) for $C_{18}H_7O_6$ [M-H]$^-$ 319.0248. found. 319.0255 amu.

1-Bromochartarin (14)

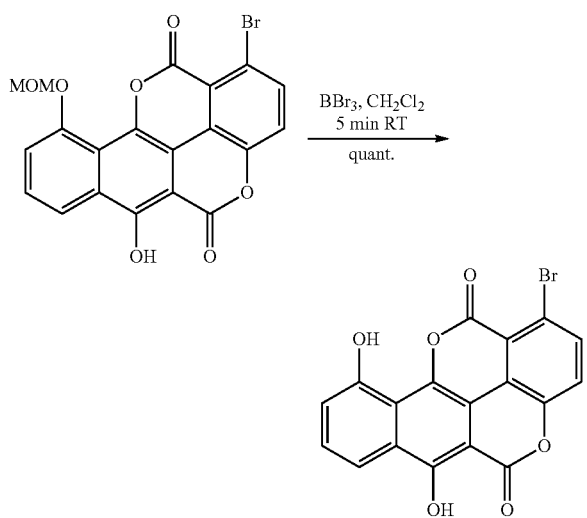

This compound was prepared as a yellow solid in quatitative yield by the reaction of (12) according to the general procedure for MOM-deprotection as described.

$R_f$ silicagel 60; chloroform/methanol 95:5=0.91
mp. 302.7° C.
$^1$H NMR (500 MHz; pyridine-$D_5$): see Table 1.
$^{13}$C NMR (125 MHz; pyridine-$D_5$): see Table 2.
IR (ATR): $\tilde{v}$ (% T)=3243 (m), 3080 (w), 1689 (s), 1605 (s), 1562 (w), 1499 (m), 1423 (m), 1325 (m), 1288 (s), 1220 (s), 1136 (s), 1095 (s), 1002 (w), 966 (m), 895 (m), 846 (m), 816 (m), 773 (s), 682 (s), 3099 (w), 1717 (m), 1632 (w), 1584 (m), 1532 (m), 1456 (m), 1360 (s), 1306 (m), 1252 (m), 1204 (s), 1114 (s), 1072 (s), 982 (m), 928 (m), 881 (m), 826 (m), 791 (m), 700 (s), 660 (s) cm$^{-1}$.
ESI-MS (ESI-): m/z=397 (100) [M-H]$^-$.
HRMS (ESI-) for $C_{18}H_6O_6^{79}Br$ [M-H]$^-$ 396.9358. found. 396.9358 amu.

1-Vinylchartarin (15)

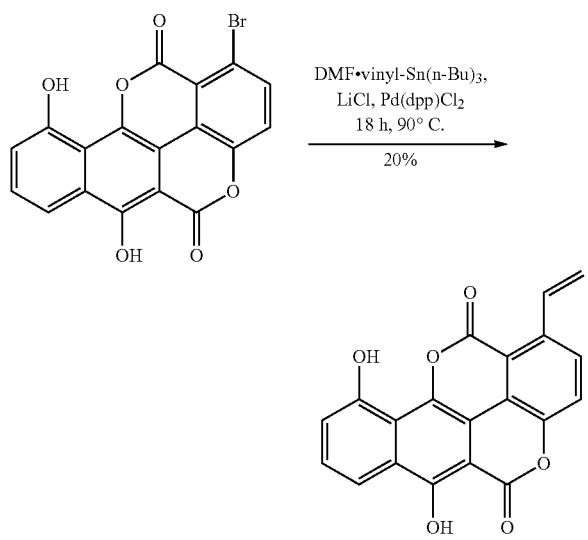

107 mg (267 μmol, 1.0 eq.) 1-bromochartarin (14), 57 mg (1.34 mmol, 5 eq.) lithium chloride and 39 mg (66.83 mmol), dichloro(1,3-bis(diphenylphosphino) propane) palladium were placed in a Schlenk tube, evacuated and flushed with argon for three times. Under argon counter flow 40 mL dried DMF and 390 μL (1.34 mmol, 5 eq.) tri-n-butyl(vinyl) tin were added. The Schlenk tube was equipped with a cooling finger and stirred at 90° C. overnight. After cooling to RT 130 mg potassium fluoride were added and the slurry was stirred for 30 min. The solvent was removed and the resulting brownish solid was dissolved in dichloro methane and washed with water. The organic phase was flushed through Celite with 50% potassium fluoride. The Celite® was extracted with methanol. After evaporation 18.5 mg (53 μmol, 20%) 1-vinylchartarin (15) were yielded as a yellow solid. (Note: the yield is much higher, but the separation from tin organic residues limits the yield drastically)

$R_f$ silicagel 60; chloroform/methanol 95:5=0.93
$^1$H NMR (300 MHz; pyridine-$D_5$): see Table 1.
$^{13}$C NMR (75 MHz; pyridine-$D_5$): see Table 2.
ESI-MS (ESI-): m/z=345 (100) [M-H]$^-$.
HRMS (ESI-) for $C_{20}H_9O_6$ [M-H]$^-$ 345.0405. found. 345.0412.

Norchartreusin

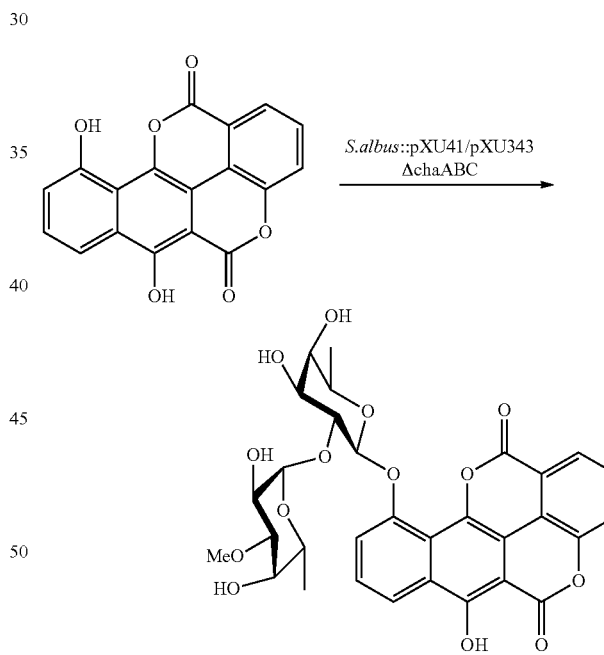

This compound was isolated as a yellow solid by fermentation of (13) according to the general procedure for fermentation and isolation as described.

$R_f$ silicagel 60; chloroform/methanol 95:5=0.07
$^1$H NMR (600 MHz; pyridine-$D_5$): see Table 5.
$^{13}$C NMR (150 MHz; pyridine-$D_5$): see Table 6.
ESI-MS (ESI-): see Table 7.
ESI-MS$^2$ (ESI-): see Table 7.
HRMS (ESI-) for $C_{31}H_{29}O_{14}$ [M-H]$^-$ 625.1563. found. 625.1556 amu.

Chartreusin (1)

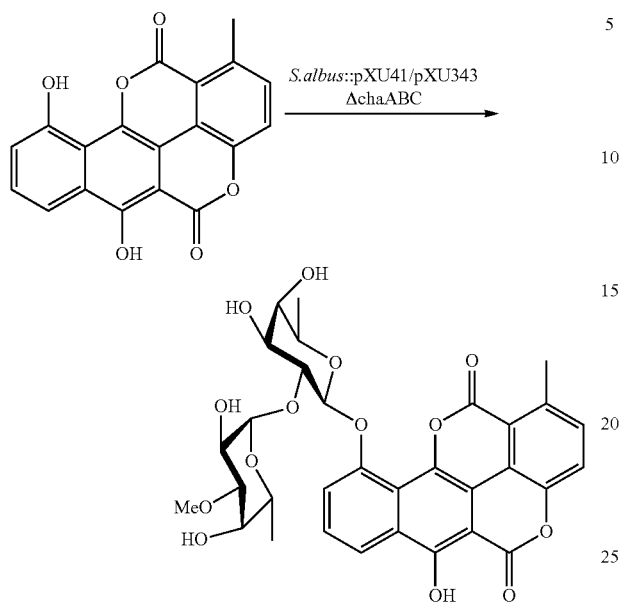

This compound was isolated as a yellow solid by fermentation of (1b) according to the general procedure for fermentation and isolation as described.

$R_f$ silicagel 60; chloroform/methanol 95:5=0.53
$^1$H NMR (600 MHz; pyridine-$D_5$): see Table 5.
$^{13}$C NMR (150 MHz; pyridine-$D_5$): see Table 6.
ESI-MS (ESI−): see Table 7.
ESI-MS$^2$ (ESI−): see Table 7.
HRMS (ESI−) for $C_{32}H_{31}O_{x4}$, [M−H]$^−$ 639.1719. found. 639.1732 amu.

Homochartreusin

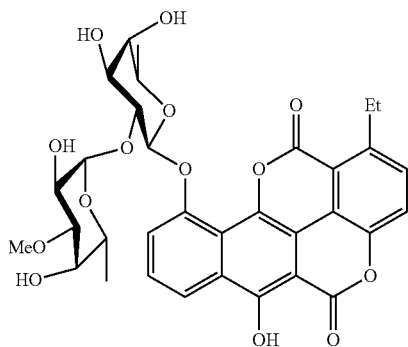

$R_f$ silicagel 60; chloroform/methanol 95:5=0.64
$^1$H NMR (500 MHz; DMSO-$D_6$): see Table 5.
$^{13}$C NMR (125 MHz; DMSO-$D_6$): see Table 6.
ESI-MS (ESI−): see Table 7.
ESI-MS (ESI+): m/z=677 [M+Na]$^+$
ESI-MS$^2$ (ESI−): see Table 7.
HRMS (ESI+): 677.1864 [M+Na]$^+$ (calcd. for $C_{33}H_{34}O_{14}Na$ 677.1846).

1-Vinylchartreusin

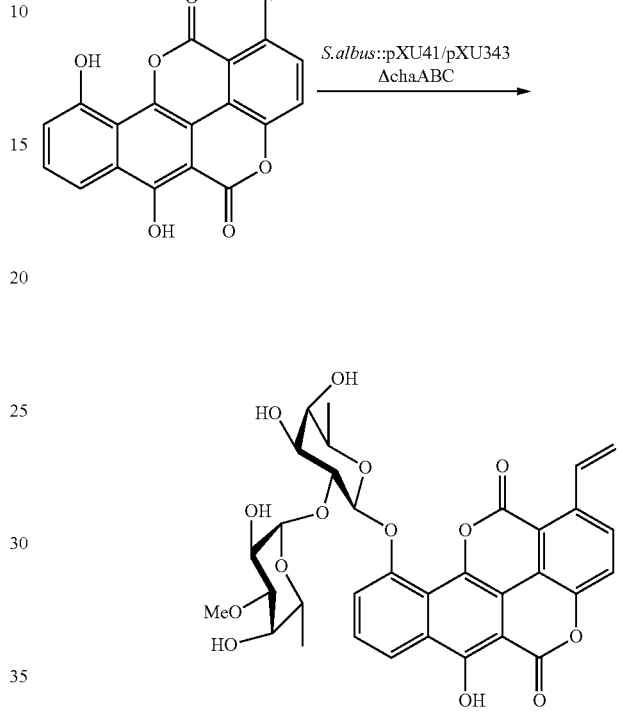

This compound was isolated as a yellow solid by fermentation of (15) according to the general procedure for fermentation and isolation as described.

$R_f$ silicagel 60; chloroform/methanol 95:5=0.53
$^1$H NMR (500 MHz; pyridine-$D_5$): see Table 5.
$^{13}$C NMR (125 MHz; pyridine-$D_5$): see Table 6.
ESI-MS (ESI−): see Table 7.
ESI-MS$^2$ (ESI−): see Table 7.
HRMS (ESI−) for $C_{33}H_{31}O_{14}$ [M−H]$^−$ 651.1719. found. 651.1723.

1-Bromochartreusin

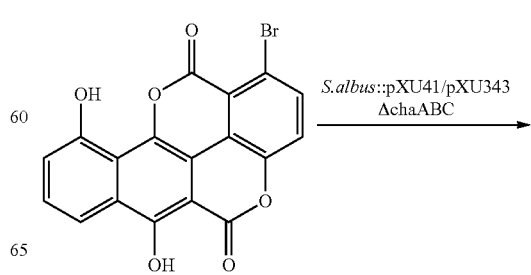

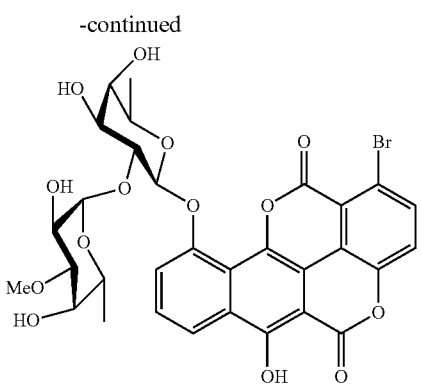

This compound was isolated as a yellow solid by fermentation of (14) according to the general procedure for fermentation and isolation as described.

$R_f$ silicagel 60; chloroform/methanol 95:5=0.36

$^1$H NMR (600 MHz; pyridine-$D_5$): see Table 5.

$^{13}$C NMR (150 MHz; pyridine-$D_5$): see Table 6.

ESI-MS (ESI−): see Table 7.

ESI-MS$^2$ (ESI−): see Table 7.

HRMS (ESI−) for $C_{31}H_{28}O_{14}{}^{79}Br$ [M−H]$^-$ 703.0668. found. 703.0685 amu.

Methyl 2-bromo-5-hydroxybenzoate (28)

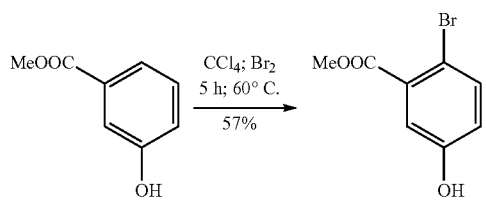 [SMILES: COC(=O)c1cccc(O)c1 ; COC(=O)c1cc(O)ccc1Br]

Methyl 3-hydroxybenzoate (40 g, 263 mmol, 1 eq.) was placed in a round bottom flask and dissolved in tetrachloromethane (600 mL). Then bromine (13.5 mL, 263 mmol, 1 eq.) was added and the solution was stirred for 5 h at 60° C. The resulting solution was concentrated and recrystallized from diisopropylether to yielding the title compound as white crystalline solid (24.74 g, 150 mmol, 57%).

$R_f$ Silica gel 60; dichloromethane: 0.19.

mp. 96-98° C.

$^1$H NMR (300 MHz; CDCl$_3$): δ==7.46 [d; 1H; $^3J_{H-H}$=8.7 Hz; CH-3]; 7.28 [d; 1H; $^4J_{H-H}$=3.1 Hz; CH-6]; 6.83 dd; 1H; $^3J_{H-H}$=8.7 Hz; $^4J_{H-H}$=3.1 Hz; CH-4]; 5.77 [s; 1H; OH]; 3.91 [s; 3H; OCH$_3$] ppm.

$^{13}$C NMR (75 MHz; CDCl$_3$): δ=166.9 (C=O); 154.9 (Ar—C-5); 135.3 (Ar—CH-3); 132.6 (Ar—C-1); 120.3 (Ar—CH-4); 118.3 (Ar—CH-6); 111.7 (Ar—C-2); 52.7 (OCH$_3$) ppm.

EI-MS (EI+, 70 eV): m/z=230/232 (61), 199/201 (100), 171/173 (15), 143/145 (11), 110 (7), 63 (14).

HRMS (ESI+) for $C_8H_7O_3Na$ [M+Na]$^+$: 252.9471. found. 252.9447.

Methyl 6-bromo-2-formyl-3-hydroxybenzoate (30a) and methyl 2-bromo-4-formyl-5-hydroxybenzoate (30b)

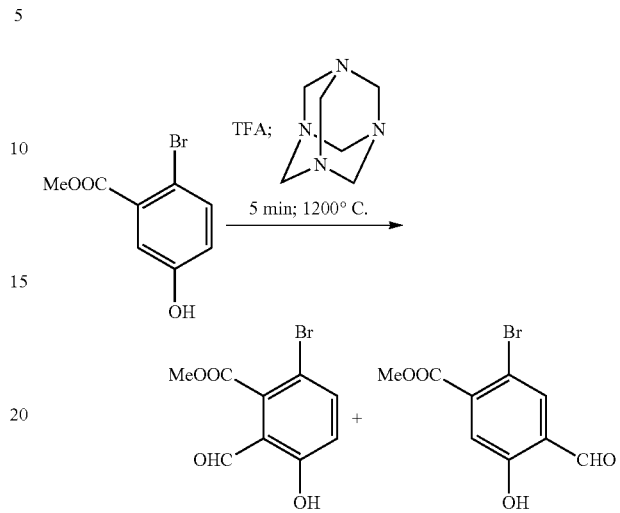

Methyl 2-bromo-5-hydroxybenzoate (28) (5 g, 21.6 mM, 1 eq.) and hexamethylenetetraamine (4.55 g, 32.5 mM, 1.5 eq.) were placed in a 50 mL MLS® fused quartz microwave vial and treated with trifluoroacetic acid (32 mL). The following microwave parameters were set:

| step | time/min | T/° C. | Maximum Power/W |
|---|---|---|---|
| 1 | 2 | 70 | 100 |
| 2 | 3 | 80 | 100 |
| 3 | 5 | 120 | 100 |
| 4 | 1 | 120 | 100 |

After cooling (15 min) the resulting brownish liquid was poured into water and neutralized with sodium bicarbonate. The aqueous phase was extracted trice with ethyl acetate. The crude extract was dried over sodium sulfate, concentrated and suspected to column chromatography with a gradient from chloroform to chloroform/methanol 98:2. The fractions containing the product mixture were recrystallized from hot cyclohexane to yield pure Methyl 6-bromo-2-formyl-3-hydroxybenzoate (29) (1.64 g, 6.33 mmol, 29.3%). A further separation of the mother liquor containing both isomers was carried out for analytical purposes with preparative HLPC using a phenomenex Luna C18 10 μm 250×21.2 mm at 21 mL/min with a gradient from 20 to 83% acetonitrile/water in 30 min.

Data for methyl 6-bromo-2-formyl-3-hydroxybenzoate (30a)

$R_f$ Silica gel 60; chloroform/methanol 95/5: 0.91.

mp. 75.6° C.

$^1$H NMR (300 MHz; CDCl$_3$): δ=11.52 [s, 1H, OH], 9.82 [s, 1H, CHO], 7.63 [d, 1H, $^3J_{H-H}$=9.0 Hz, CH-5], 6.94 [d, 1H, $^3J_{H-H}$=9.0 Hz, CH-4], 3.99 [s, 3H, OCH$_3$] ppm.

$^{13}$C NMR (75 MHz; CDCl$_3$): δ=194.0 (CHO), 165.9 (COOCH$_3$), 161.3 (Ar—COH), 140.6 (Ar—CH-5), 138.6 (ArC—COOCH$_3$), 121.2 (Ar—CH-4), 118.0 (Ar—CCHO), 108.9 (Ar—CBr), 53.3 (OCH$_3$) ppm.

IR (ATR): ṽ (T$_{rel}$)=3075 (w), 2955 (w), 2925 (w), 2846 (w), 1712 (s), 1654 (s), 1441 (s), 1330 (s), 1306 (s), 1279 (s), 1257 (s), 1197 (m), 1173 (s), 1160 (s), 1118 (s), 1011 (s), 928 (s), 828 (s), 799 (s), 752 (s), 742 (s), 707 (s), 653 (s) cm$^{-1}$.

EI-MS (EI+, 70 eV): m/z=258/260 (48), 243/245 (36), 230/232 (65), 199/201 (100), 171/173 (20), 170/172 (20), 143/145 (15), 63 (44).

HRMS (ESI−) calc. for $C_9H_6{}^{79}BrO_4$ [M+H]$^+$: 256.9455. found. 256.9457.

Data for methyl 2-bromo-4-formyl-5-hydroxybenzoate (30b)

$R_f$ Silica gel 60; chloroform/methanol 95/5: 0.91.

mp. 72.3° C.

$^1$H NMR (300 MHz; CDCl$_3$): δ=10.75 [s, 1H, OH], 9.85 [s, 1H CHO], 7.77 [s, 1H, CH-3], 7.27 [s, 1H, CH-6], 3.91 [s, 3H, OCH$_3$] ppm.

$^{13}$C NMR (75 MHz; CDCl$_3$): δ=195.2 (CHO), 165.5 (COOCH$_3$), 159.8 (Ar—COH), 139.5 (Ar—CCOOCH$_3$), 138.0 (Ar—CH-3), 122.6 (Ar—CCHO), 120.4 (Ar—CH-6), 109.5 (Ar—CBr), 52.9 (COOCH$_3$).

IR (ATR): ṽ ($T_{rel}$)=3197 (w), 2952 (w), 2879 (w), 1733 (s), 1666 (s), 1554 (m), 1473 (m), 1433 (m), 1297 (s), 1278 (s), 1213 (s), 1172 (s), 1115 (s), 1003 (s), 888 (s), 820 (s), 760 (s), 717 (s), 655 (s) cm$^{-1}$.

EI-MS (EI+, 70 eV): m/z=258/260 (94), 227/229 (100), 199/201 (19), 171/173 (8), 143/145 (19), 63 (29).

HRMS (ESI−) calc. for $C_9H_6{}^{79}BrO_4$ [M+H]$^+$: 256.9455. found. 256.9457.

Methyl 6-bromo-coumarin-5-carboxylate (9)

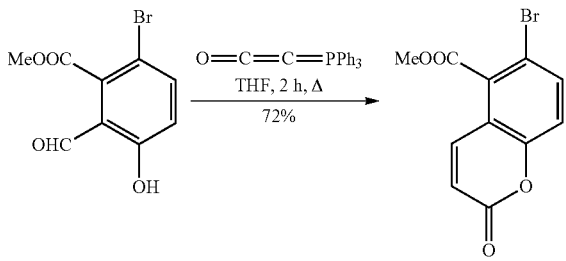

Methyl 6-bromo-2-formyl-3-hydroxybenzoate (30b) (800 mg, 3.09 mmol, 1.0 eq.) and (Triphenylphosphoranylidene) ketene (1.03 g, 3.4 mmol, 1.1 eq.) were placed in a Schlenk tube, flushed with argon three times and dissolved in THF (32 mL) The mixture was heated while refluxing for 2 h, cooled to rt, and concentrated under reduced pressure. The resulting solid was suspected to column chromatography with a gradient from cyclohexane to cyclohexane/ethyl acetate 4:1 yielding the title compound as pale yellow solid (633 mg, 2.24 mmol, 72%).

Methyl 3-bromo-5-nitrobenzoate (51)

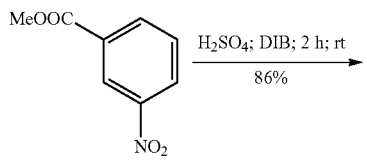

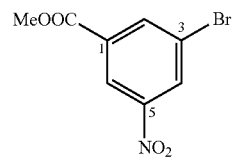

methyl 3-nitrobenzoate (50) (85.4 g; 471 mmol, 1 eq.) were dissolved in concentrated sulfuric acid (500 mL). Then a solution of dibromoisocyanuric acid (67.6 g; 235 mmol, 0.5 eq.) in concentrated sulfuric acid (850 mL) was added. After stirring the clear solution for 2 hours the whole mixture were poured on 5 kg ice. The slurry was extracted 5 times with each 2 L of dichloromethane. The combined organic phases were dried over sodium sulfate. After evaporating of the solvent the crude product were recrystallize from methanol to yield the title compound (105.8 g 406 mmol, 86%) as large pale yellow crystals.

$R_f$ silica gel 60; chloroform/methanol 95:5=0.87.

mp. 74.1° C.

$^1$H NMR (300 MHz; CHCl$_3$): δ=8.75 (dd, 1H, $^4J_{H\text{-}H\,1}$=2.0 Hz, $^4J_{H\text{-}H\,2}$=1.4 Hz, CH-6); 8.51 (dd, 1H, $^4J_{H\text{-}H\,1}$= $^4J_{H\text{-}H\,2}$=2.0 Hz, Ar—CH-4); 8.45 (dd, 1H, $^4J_{H\text{-}H\,1}$=1.7 Hz, $^4J_{H\text{-}H\,2}$=1.5 Hz, Ar—CH-2); 3.96 (s, 3H, OCH$_3$) ppm.

$^{13}$C NMR (75 MHz; CHCl$_3$): δ=163.7 (COOMe), 148.7 (Ar—C—NO$_2$), 138.2 (Ar—CH-2), 133.2 (Ar—CCOOMe), 130.4 (Ar—CH-4), 123.1 (Ar—CH-6), 123.0 (Ar—C—Br), 53.1 (OCH$_3$) ppm.

IR (ATR): ṽ ($T_{rel}$)=3096 (w), 3082 (m), 2955 (w), 2917 (w), 2870 (w), 2847 (w), 1725 (s), 1607 (w), 1527 (m), 1446 (m), 1434 (m), 1420 (m), 1345 (s), 1284 (s), 1243 (m), 1197 (m), 1146 (m), 1087 (m), 980 (m), 919 (m), 902 (s), 842 (m), 770 (m), 733 (s), 726 (s), 653 (m) cm$^{-1}$.

EI-MS (EI+, 70 eV): m/z=259/261 (65) [M]$^{•+}$, 228/230 (100), 213/215 (8), 182/184 (22), 172/172 (6), 154/156 (6), 75 (31), 74 (30).

HRMS (ESI+) calc. for $C_8H_6N^{79}BrO_4$ [M+H]$^+$: 258.9486. found 258.9480 amu.

Methyl 3-amino-5-bromobenzoate (52)

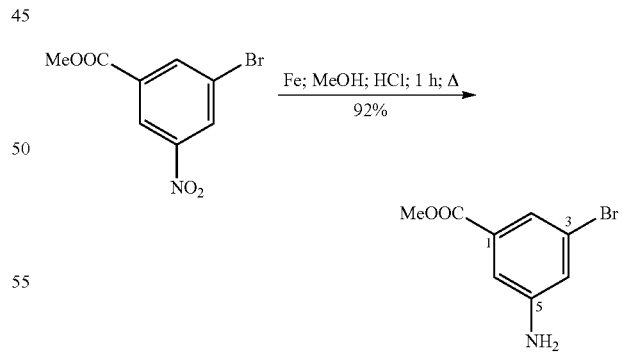

Methyl 3-bromo-5-nitrobenzoate (51) (1.79 g, 6.86 mmol, 1 eq.) and iron (2.3 g, 41.2 mmol, 6 eq.) were suspended in methanol (40 mL) while refluxing hydrochloric acid (28 mL, 6 N) was added dropwise. After the addition the solution was further stirred under reflux for 45 min. After cooling the solution was diluted with water (150 mL) and neutralized with sodium bicarbonate. The greenish brown solution was extracted with chloroform four times. The combined organic phases were dried with sodium sulfate and concentrated, yielding the title compound as pale yellow solid (1.45 g, 6.3 mmol, 92%).

$R_f$ silica gel 60; chloroform/methanol 95:5=0.56.

mp. 190.8° C.

$^1$H NMR (300 MHz; CDCl$_3$): δ=8.14 (s, 1H, NH$_2$), 7.57 (dd, 1H, $^4J_{H-H\ 1}$=$^4J_{H-H\ 2}$=1.6 Hz, Ar—CH-2), 7.54 (dd, 1H, $^4J_{H-H\ 1}$=$^4J_{H-H\ 2}$=1.7 Hz, Ar—CH-6), 7.42 (dd, 1H, $^4J_{H-H\ 1}$=$^4J_{H-H\ 2}$=1.7 Hz, Ar—CH-4), 3.84 (s, 3H, COOCH$_3$) ppm.

$^{13}$C NMR (75 MHz; CDCl$_3$): δ=164.8 (Ar—COOMe), 143.0 (Ar—C—NH$_2$), 132.4 (Ar—C-1), 125.0 (Ar—CH-4), 124.3 (Ar—CH-2), 122.1 (Ar—C—Br), 118.1 (Ar—CH-6), 52.6 (OCH$_3$) ppm.

IR (ATR): ṽ (T$_{rel}$)=3067 (w), 2952 (w), 2839 (m), 2583 (w), 1730 (s), 1536 (m), 1439 (m), 1428 (m), 1290 (s), 1210 (s), 1113 (m), 976 (m), 914 (w), 881 (m), 830 (m), 766 (s), 731 (m), 662 (m) cm$^{-1}$.

EI-MS (EI+, 70 eV): m/z=229/231 (100) [M]$^{•+}$, 198/200 (48), 170/172 (30), 171/173 (35), 143/154 (5), 90/92 (15), 63 (26).

HRMS (ESI–) calc. for C$_8$H$_9$N$^{79}$BrO$_2$ [M+H]$^+$: 229.9811. found 229.9819 amu.

Methyl 3-bromo-5-hydroxybenzoate (53)

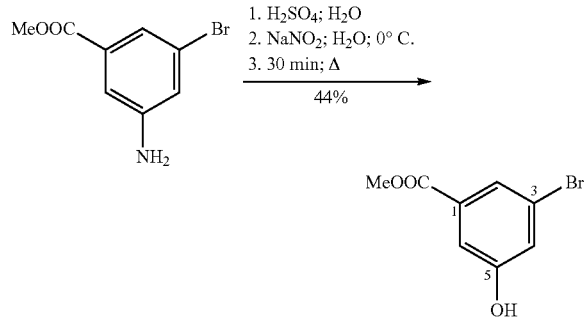

A solution of concentrated sulfuric acid (30 mL) in water (200 mL) and methyl 3-amino-5-bromobenzoate (52) (17.08 g, 74 mmol, 1 eq.) were cooled with an ice bath to 0° C. Then a solution sodium nitrite (5.12 g, 74 mmol, 1 eq.) was added drop wise while the solution turned to yellow. After additional 30 min the solution were heated and refluxed for 30 min After cooling to rt the brownish solution were extracted four times with chloroform. The combined organic phases were dried over sodium sulfate and concentrated under reduced pressure. The crude product was flash purified using a silica gel pad with a gradient from chloroform to chloroform/methanol 95:5. The fraction with the desired product were collected, concentrated a suspected to recrystallization from petroleum ether/toluene to yield a yellow-brownish solid (7.57 g, 33 mmol, 44%). (Note: traces of colored side products cause the reddish brown color of the product, the purity (>95%) of the collected crystals was determined using NMR and GC-MS)

$R_f$ silica gel 60; chloroform/methanol 95:5=0.44.

mp. 125° C.

$^1$H NMR (300 MHz; CDCl$_3$): δ=7.98 (s, 1H, Ar—OH), 7.65 (dd, 1H, $^4J_{H-H\ 1}$=$^4J_{H-H\ 1}$=1.5 Hz, Ar—CH-2), 7.44 (dd, 1H, $^4J_{H-H\ 1}$=2.3 Hz, $^4J_{H-H\ 2}$=1.4 Hz, Ar—CH-6), 7.20 (dd, 1H, $^4J_{H-H\ 1}$=$^4J_{H-H\ 2}$=2.1 Hz, Ar—CH-4), 3.87 (s, 3H, OCH$_3$), ppm.

$^{13}$C NMR (75 MHz; CDCl$_3$): δ=166.0 (COOMe), 157.5 (Ar—C—OH), 132.5 (Ar—C-1), 124.1 (Ar—CH-2), 123.4 (Ar—CH-4), 122.6 (Ar—C—Br), 115.6 (Ar—CH-6), 52.5 (OCH$_3$) ppm.

IR (ATR): ṽ (T$_{rel}$)=3411 (m), 3094 (w), 3062 (w), 2955 (w), 1703 (s), 1591 (s), 1480 (m), 1432 (s), 1308 (s), 1279 (s), 1244 (s), 1214 (s), 1114 (m), 1001 (s), 915 (s), 874 (m), 835 (m), 762 (s), 731 (m), 667 (m) cm$^{-1}$.

EI-MS (EI+, 70 eV): m/z=230/232 (92) [M]$^{•+}$, 199/201 (100), 171/173 (24), 143/145 (14), 63 (24).

HRMS (ESI–) calc. for C$_8$H$_6$$^{79}$BrO$_3$ [M–H]$^-$: 228.9503. found 228.9498 amu.

Methyl 5-bromo-2-formyl-3-hydroxybenzoate (54) and Methyl 3-bromo-4-formyl-5-hydroxybenzoate (55)

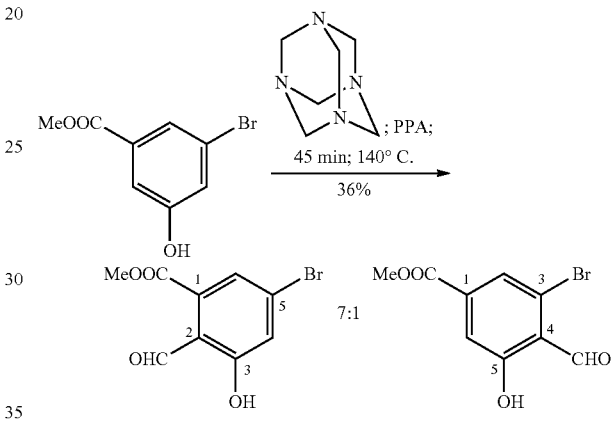

methyl 3-bromo-5-hydroxybenzoate (53) (5 g 21.6 mmol, 1.0 eq.) was placed in a round bottom flask followed by poly phosphoric acid (20 mL). The reactor were equipped with a KPG-stirrer and heated in an oil bath to 120° C. The sequential addition of urotopine (4.55 g, 32.5 mmol, 1.5 eq.) was started after the phenol were melted and completely dissolved into the acid. After 45 min the oil bath were removed and to the cooled mixture water was added. After neutralization with sodium bicarbonate the slurry was extracted trice with ethyl acetate. The crude extract was dried over sodium sulfate, concentrated and suspected to column chromatography with a gradient from cyclohexane to cyclohexane/ethyl acetate 4:1. The fractions containing the product mixture were recrystallized from hot cyclohexane to yield pure methyl 5-bromo-2-formyl-3-hydroxybenzoate (54) (2.02 g, 7.8 mmol, 36%). A further separation of the mother liquor containing both isomers in approximately 1:1 ratio were purified for analytical purposes with preparative HLPC using a phenomenex Synergy Hydro RP 80 250×21.2 mm at 21 mL/min with a gradient from 10 to 83% acetonitrile/20 mM phosphate buffer pH 7.5 in 30 min.

Data for methyl 5-bromo-2-formyl-3-hydroxybenzoate (54)

$R_f$ silica gel 60; chloroform/methanol 95:5=0.78.

mp. 106.9° C.

$^1$H NMR (300 MHz; CDCl$_3$): δ=ppm. 12.28 (s, 1H, OH), 10.59 (s, 1H, CHO), 7.60 (d, 1H, $^4J_{H-H}$=1.9 Hz, Ar—CH-6), 7.34 (d, 1H, $^4J_{H-H}$=1.9 Hz, Ar—CH-4), 3.95 (s, 3H, OCH$_3$) ppm.

$^{13}$C NMR (75 MHz; CDCl$_3$): δ=196.9 (CHO), 165.1 (Ar—COOMe), 163.5 (Ar—C—OH), 134.4 (Ar—CH-1), 130.5 (Ar—C—Br), 125.6 (Ar—CH-6), 125.4 (Ar—CH-4), 117.3 (Ar—C—CHO), 53.1 (COOCH$_3$) ppm.

IR (ATR): ṽ (T$_{rel}$)=3091 (w), 3068 (w), 3023 (w), 2964 (w), 1713 (s), 1681 (w), 1637 (s), 1598 (m), 1558 (m), 1470 (m), 1447 (m), 1432 (m), 1416 (w), 1397 (m), 1335 (m), 1296 (s), 1251 (s), 1203 (s), 1172 (s), 1086 (s), 1019 (s), 927 (s), 882 (m), 868 (s), 859 (s), 792 (s), 768 (s), 718 (m), 668 (m) cm$^{-1}$.

EI-MS (EI+, 70 eV): m/z=258/260 (27) [M]$^{\cdot+}$, 243/245 (100), 225/227 (28), 199/201 (37), 171/173 (13), 143/145 (10), 63 (33).

HRMS (ESI+) calc. for C$_9$H$_6$$^{79}$BrO$_4$ [M+H]$^+$: 256.9455. found 256.9458 amu.

Data for methyl 3-bromo-4-formyl-5-hydroxybenzoate (55)

R$_f$ silica gel 60; chloroform/methanol 95:5=0.78.
mp. 97.6° C.
$^1$H NMR (300 MHz; CDCl$_3$): δ=11.88 (s, 1H, OH), 10.36 (s, 1H, CHO), 7.76 (d, 1H, $^4J_{H\text{-}H}$=1.5 Hz, Ar—CH-2), 7.55 (d, 1H, $^4J_{H\text{-}H}$=1.5 Hz, Ar—CH-6), 3.92 (s, 3H, OCH$_3$) ppm.
$^{13}$C NMR (75 MHz; CDCl$_3$): δ=197.7 (CHO), 164.4 (COOMe), 163.5 (Ar—C—OH), 137.8 (Ar—C—COOMe), 127.3 (Ar—C—Br), 124.8 (Ar—CH-2), 119.8 (Ar—C—CHO), 119.3 (Ar—CH-6), 52.9 (COO—CH$_3$) ppm.

IR (ATR): ṽ (T$_{rel}$)=3091 (w), 2961 (w), 2907 (w), 2849 (w), 1730 (s), 1654 (s), 1556 (s), 1439 (m), 1413 (m), 1387 (s), 1336 (m), 1280 (s), 1247 (s), 1200 (s), 1165 (s), 1092 (s), 1000 (s), 928 (s), 899 (m), 885 (m), 841 (m), 803 (s), 767 (s), 735 (s), 713 (s), 676 (m), 665 (m), 654 (m) cm$^{-1}$.

EI-MS (EI+, 70 eV): m/z=258/260 (100) [M]$^{\cdot+}$, 257/259 (66), 227/229 (50), 199/201 (16), 143/145 (16), 63 (37).

HRMS (ESI+) calc. for C$_9$H$_6$$^{79}$BrO$_4$ [M+H]$^+$: 256.9455. found 256.9458 amu.

Methyl 7-bromo-coumarin-5-carboxylate (56)

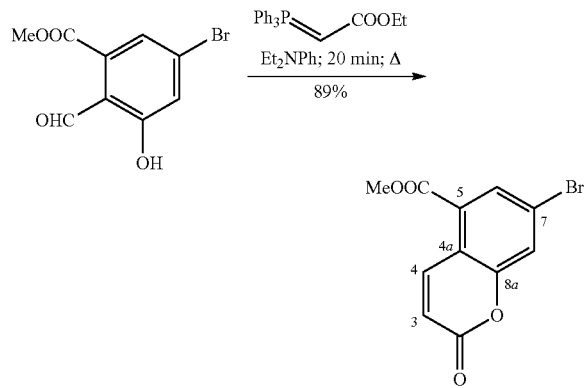

Salicylic aldehyde (54) (1.5 g, 5.79 mmol, 1 eq.) and (carbethoxymethylen)-triphenylphosphorane (2.22 g, 6.37 mmol, 1.1 eq.) were placed in a Schlenk tube and flushed with argon three times. Then N,N-diethylaniline (30 mL) was added and the solution were refluxed for 20 min. After cooling the solution was diluted with ethyl acetate and extracted twice with 2N hydrochloric acid. After concentration the crude product was suspected to column chromatography with a gradient from cyclohexane to cyclohexane/ethyl acetate 4:1. The title compound was isolated as pale yellow powder in 89% yield.

R$_f$ silicagel 60; dichloromethane=0.67.
mp. 157.4-159.2° C.

$^1$H NMR (300 MHz; CDCl$_3$): see Table 8.
$^{13}$C NMR (75 MHz; CDCl$_3$): see Table 9.

IR (ATR): ṽ (T$_{rel}$)=3073 (m), 2958 (w), 2852 (w), 1716 (s), 1579 (s), 1460 (m), 1437 (m), 1398 (m), 1281 (s), 1240 (s), 1190 (s), 1106 (s), 1020 (s), 942 (s), 883 (s), 838 (s), 775 (s), 743 (s), 671 (m) cm$^{-1}$.

EI-MS (EI+, 70 eV): m/z=282/284 (100) [M]$^{\cdot+}$, 254/256 (87), 223/225 (65), 195/197 (27), 62 (46).

HRMS (ESI+) calc. for C$_{11}$H$_7$$^{79}$BrO$_4$ [M+H]$^+$: 282.9600. found 282.9603 amu.

Methyl 7-methyl-coumarin-5-carboxylate (57)

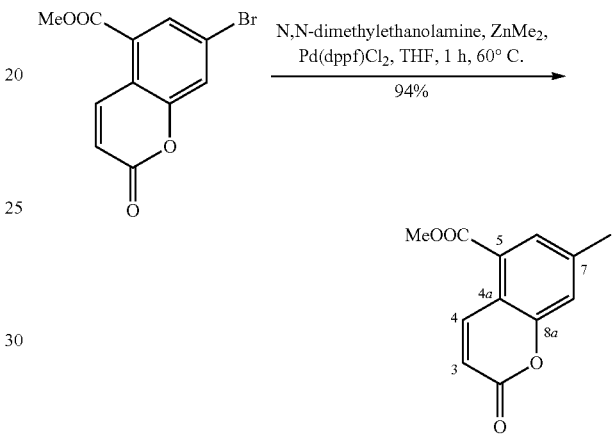

To a solution of bromocoumarin (56) (308 mg, 1.09 mmol, 1 eq.) and [1,1'-bis(diphenylphosphino)ferrocene] dichloropalladium complex with dichloromethane (88.8 mg, 109 μmol, 0.1 eq.) in THF (15 mL) N,N-dimethylethanolamin (22 μL, 218 μmol, 0.2 eq.) and a dimethyl zinc solution in toluene (1.8 mL, 1.2 mol/L, 2.18 mmol, 2 eq.) was added. The yellow solution was stirred for 1 h. Then additional 1 N,N-dimethylethanolamin (0.2 eq.) and dimethyl zinc solution (2 eq.) were added and the mixture were heated to 60° C. After additional 1 h at 60° C. the solution were quenched with a saturated ammonium chloride solution followed by extraction with ethyl acetate for three times. The combined organic phases were dried over sodium sulfate and concentrated in vacuum. The crude product was purified using flash chromatography on silica gel with a gradient from cyclohexane to cyclohexane/ethyl acetate 7:1. The combined fractions yielded 222.4 mg (1.02 mmol, 94%) of the title compound as a pale yellow powder.

R$_f$ silicagel 60; dichloromethane=0.59.
mp. 144.5-144.9° C.
$^1$H NMR (300 MHz; CDCl$_3$): see Table 8.
$^{13}$C NMR (75 MHz; CDCl$_3$): see Table 9.

IR (ATR): ṽ (T$_{rel}$)=3415 (m), 3099 (w), 2952 (w), 2854 (w), 1712 (s), 1607 (m), 1551 (m), 1441 (m), 1393 (m), 1304 (s), 1243 (s), 1200 (s), 1134 (m), 1103 (s), 1031 (s), 998 (s), 876 (s), 830 (s), 759 (m), 714 (m) cm$^{-1}$.

EI-MS (EI+, 70 eV): m/z=218 (100) [M]$^{\cdot+}$, 190 (80), 187 (31), 159 (83), 131 (48), 77 (27).

HRMS (ESI+) calc. for C$_{12}$H$_{11}$O$_4$ [M+H]$^+$: 219.0652. found 219.0650 amu.

Methyl 7-ethyl-coumarin-5-carboxylate (58)

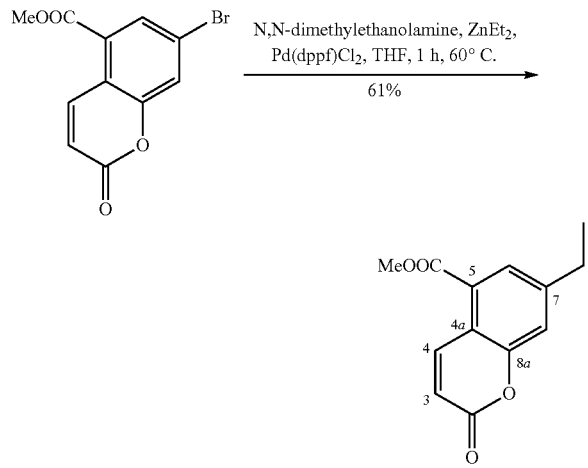 [SMILES: COC(=O)c1cc(Br)cc2oc(=O)ccc12 ; COC(=O)c1cc(C)cc2oc(=O)ccc12]

See procedure of methyl 7-methyl-coumarin-5-carboxylate (56). Diethyl zinc was used instead of dimethyl zinc.

$R_f$ silicagel 60; dichloromethane=0.70.

mp. 119.1-119.7° C.

$^1$H NMR (300 MHz; CDCl$_3$): see Table 8.

$^{13}$C NMR (75 MHz; CDCl$_3$): see Table 9.

IR (ATR): $\tilde{v}$ ($T_{rel}$)=3415 (m), 3099 (w), 2952 (w), 2854 (w), 1712 (s), 1441 (m), 1393 (m), 1304 (s), 1243 (s), 1200 (s), 1134 (m), 1103 (s), 1031 (s), 998 (s), 876 (s), 830 (s), 794 (m), 777 (m), 759 (m), 714 (m) cm$^{-1}$.

EI-MS (EI+, 70 eV): m/z=232 (87) [M]$^{\cdot+}$, 217 (13), 204 (58), 201 (24), 189 (100), 173 (27), 161 (13), 145 (39), 133 (15), 115 (37), 102 (8), 91 (14), 77 (7), 63 (12).

HRMS (ESI+) calc. for C$_{13}$H$_{13}$O$_4$ [M+H]$^+$: 233.0808. found 233.0807 amu.

Methyl 7-(vinyl)-coumarin-5-carboxylate (59)

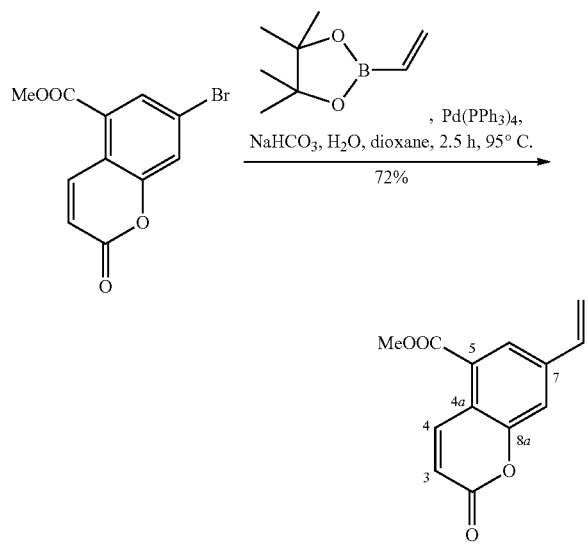

Bromocoumarin (56) (50 mg, 177 µmol, 1 eq.), and tetrakis(triphenylphosphine)palladium(0) (10.2 mg, 8.8 µmol, 0.05 eq.) were placed in a Schlenk tube and flushed with argon three times. Then a degassed mixture of water and dioxane (1:1, v/v, 16 mL) was added followed by 45 µL (265 µmol, 1.5 eq.) vinylboronic acid pinacol ester. The mixture was stirred for 2.5 h at 95° C. After cooling water was added. The solution was extracted trice with ethyl acetate. The combined organic phases were dried over sodium sulfate concentrated and suspected to column chromatography with a gradient from pentane to cyclohexane to cyclohexane/ethyl acetate 9:1. To yield of the title compound as white crystalline solid (29.7 mg, 127 µmol, 72%).

$R_f$ silicagel 60; chloroform/methanol 95:5=0.9.

$^1$H NMR (300 MHz; CDCl$_3$): see Table 8.

$^{13}$C NMR (75 MHz; CDCl$_3$): see Table 9.

EI-MS (EI+, 70 eV): m/z=230 (86) [M]$^{\cdot+}$, 202 (70), 199 (23), 171 (92), 159 (23), 143 (42), 131 (27), 115 (100), 89 (33), 63 (26).

HRMS (ESI+) calc. for C$_{13}$H$_{10}$O$_4$Na [M+Na]$^+$: 253.0471. found 253.0568 amu.

Methyl 7-((trimethylsilyl)ethynyl)-coumarin-5-carboxylate (60)

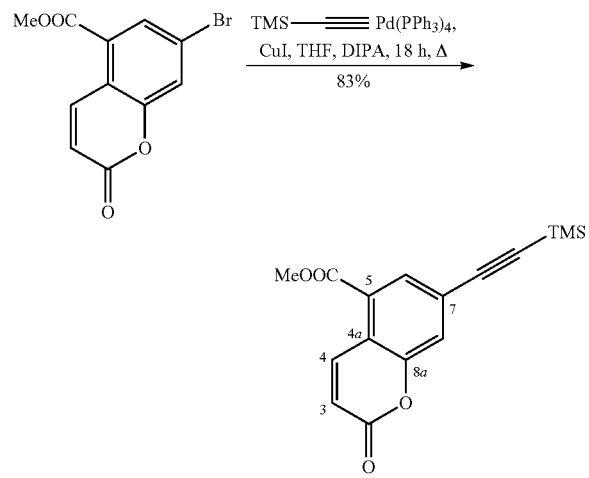

Bromocoumarin (56) (203 mg, 717 µmol, 1 eq.), copper (I)iodide (13.7 mg, 72 µmol, 0.1 eq.) and tetrakis(triphenylphosphine)palladium(0) (83 mg, 72 µmol, 0.1 eq.) were placed in a Schlenk tube and flushed with argon three times. Then of a degassed mixture of dithylamine and THF (16 mL, 1:1, v/v) was added followed by trimethylsilylacetylene (204 µL, 1.43 mmol, 2 eq.). The mixture was stirred overnight while refluxing. 2- and 4 hours after starting the reaction further 2 eq. of trimethylsilylacetylene were added. After cooling mixture were quenched with 1 N hydrochloric acid. The solution was extracted trice with diethyl ether. The combined organic phases were dried over sodium sulfate concentrated and suspected to column chromatography with a gradient from pentane to cyclohexane to cyclohexane/ethyl acetate 9:1. To yield the title compound as white crystalline solid (179 mg, 596 µmol, 83%).

$R_f$ silicagel 60; chloroform/methanol 95:5=0.5.

mp. 116.5-117.3° C.

$^1$H NMR (300 MHz; CDCl$_3$): see Table 8.

$^{13}$C NMR (75 MHz; CDCl$_3$): see Table 9.

IR (ATR): ṽ (T$_{rel}$)=3072 (w), 2957 (w), 2899 (w), 1739 (s), 1599 (m), 1329 (m), 1306 (m), 1241 (m), 1200 (m), 1138 (m), 1110 (m), 1029 (m), 997 (m), 847 (s), 759 (m), 703 (m) cm$^{-1}$.

EI-MS (EI+, 70 eV): m/z=300 (33) [M]$^{•+}$, 285 (100), 197 (14), 155 (5).

HRMS (ESI+) calc. for C$_{16}$H$_{17}$O$_4$Si [M+H]$^+$: 301.0891. found 301.0889 amu.

10-MOM-(1→2)-abeo-bromochartarin (61)

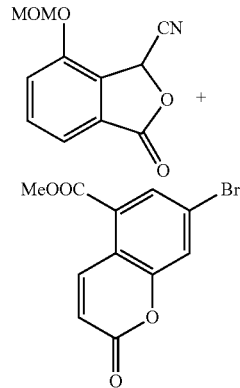

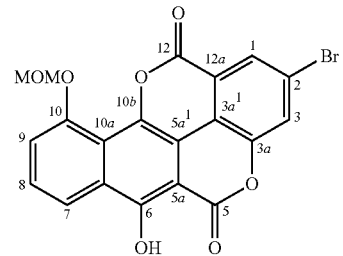

This compound was prepared as a yellow solid in 92% yield by the reaction between (22) and (56) according to the general procedure for annulation as described.

R$_f$ silicagel 60; chloroform/methanol 95:5=0.95.
mp. 228° C.→brown.
$^1$H NMR (600 MHz; CD$_2$Cl$_2$): see Table 10.
$^{13}$C NMR (150 MHz; CD$_2$Cl$_2$): see Table 11.
IR (ATR) ṽ (% T)=3182 (w), 3081 (w), 2923 (w), 2851 (w), 1739 (s), 1709 (s), 1604 (m), 1582 (m), 1500 (m), 1455 (m), 1374 (m), 1317 (s), 1284 (s), 1210 (s), 1100 (s), 1071 (s), 1008 (s), 919 (s), 876 (m), 771 (s), 714 (s), 659 (m) cm$^{-1}$.

EI-MS (EI+, 70 eV): m/z=444/442 (39) [M]$^{•+}$, 414/412 (100), 398/400 (37), 397/399 (43), 369/371 (47), 348 (48), 334 (41).

HRMS (ESI−) calc. for C$_{20}$H$_{10}^{79}$BrO$_7$ [M−H]$^-$: 440.9615. found 440.9613 amu.

10-MOM-(1→2)-abeo-chartarin (62)

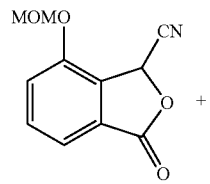

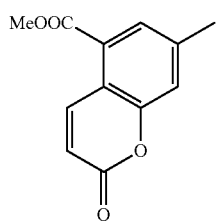

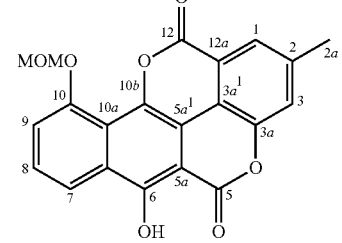

This compound was prepared as a yellow solid in 84% yield by the reaction between (22) and (57) according to the general procedure for annulation as described.

R$_f$ silicagel 60; chloroform/methanol 95:5=0.95.
mp. 246.2° C.
$^1$H NMR (600 MHz; CD$_2$Cl$_2$): see Table 10.
$^{13}$C NMR (150 MHz; CD$_2$Cl$_2$): see Table 11.
IR (ATR): ṽ (% T)=3229 (w), 2979 (w), 2843 (w), 1723 (s), 1621 (m), 1502 (s), 1449 (m), 1399 (s), 1371 (s), 1334 (m), 1279 (m), 1210 (s), 1153 (s), 1092 (s), 1078 (s), 1011 (s), 922 (s), 869 (m), 767 (s), 737 (m) cm$^{-1}$.

EI-MS (EI+, 70 eV): m/z=378 (6) [M]$^{•+}$, 348 (11), 334 (21), 320 (100), 292 (25), 236 (27).

HRMS (ESI−) calc. for C$_{21}$H$_{13}$O$_7$ [M−H]$^-$: 377.0667. found 377.0664 amu.

10-MOM-(1→2)-abeo-homochartarin (63)

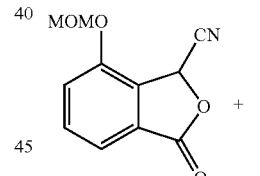

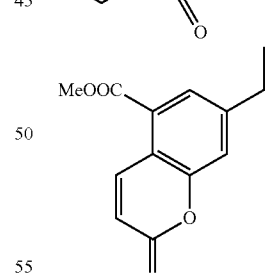

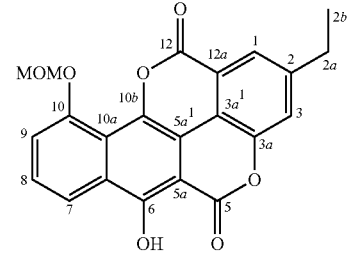

This compound was prepared as a yellow solid in 60% yield by the reaction between (22) and (58) according to the general procedure for annulation as described.

$R_f$ silicagel 60; chloroform/methanol 95:5=0.95.

mp. 213.6-214.5° C.

$^1$H NMR (600 MHz; CD$_2$Cl$_2$): see Table 10.

$^{13}$C NMR (150 MHz; CD$_2$Cl$_2$): see Table 11.

IR (ATR): ṽ (% T)=3229 (w), 3056 (w), 2969 (w), 2837 (w), 1706 (s), 1610 (m), 1507 (s), 1436 (s), 1372 (m), 1277 (m), 1209 (s), 1151 (s), 1090 (s), 1013 (s), 919 (s), 876 (m), 766 (s), 737 (m) cm$^{-1}$.

EI-MS (EI+, 70 eV): m/z=392 (8) [M]$^{·+}$, 362 (14), 334 (100), 320 (89), 306 (27).

HRMS (ESI−) calc. for C$_{22}$H$_{15}$O$_7$ [M−H]$^−$: 391.0823. found 391.0827 amu.

10-MOM-(1→2)-abeo-((trimethylsilyl)ethynyl)-chartarin (65)

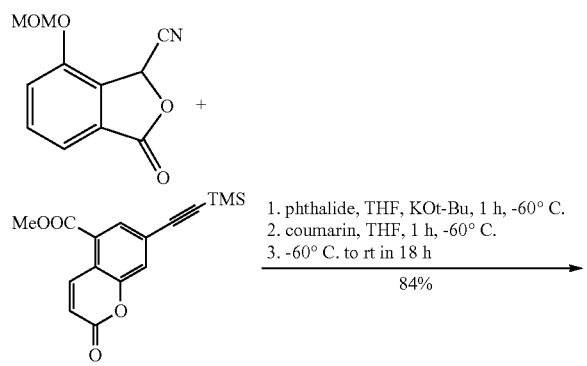

This compound was prepared as a yellow solid in 84% yield by the reaction between (22) and (60) according to the general procedure for annulation as described.

$R_f$ silicagel 60; chloroform/methanol 95:5=0.95.

mp. 212-214° C.

$^1$H NMR (600 MHz; CD$_2$Cl$_2$): see Table 10.

$^{13}$C NMR (150 MHz; CD$_2$Cl$_2$): see Table 11.

IR (ATR): ṽ (% T)=3241 (w), 2953 (w), 2839 (w), 2160 (w), 1709 (s), 1608 (m), 1507 (s), 1427 (s), 1372 (m), 1317 (m), 1241 (m), 1209 (m), 1145 (m), 1095 (s), 1011 (s), 889 (m), 847 (s), 765 (s) cm$^{-1}$.

EI-MS (EI+, 70 eV): m/z=460 (10) [M]$^{·+}$, 430 (14), 348 (72), 334 (31), 333 (31), 305 (24), 305 (23), 176 (100).

HRMS (ESI−) calc. for C$_{25}$H$_{19}$O$_7$Si [M−H]$^−$: 459.0906. found 459.0910 amu.

(1→2)-Abeo-bromochartarin (66)

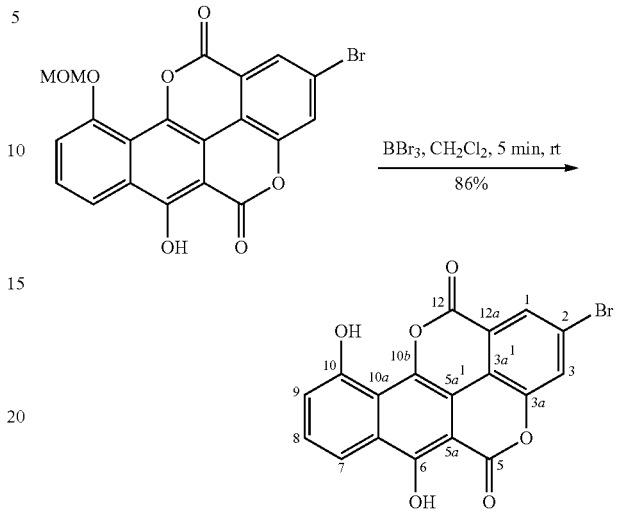

This compound was prepared as a yellow solid in 86% yield by the reaction of (61) according to the general procedure for MOM-deprotection as described.

$R_f$ silicagel 60; chloroform/methanol 95:5=0.89.

mp. 350° C.→dark brown.

$^1$H NMR (600 MHz; CD$_2$Cl$_2$): see Table 12.

$^{13}$C NMR (150 MHz; CD$_2$Cl$_2$): see Table 13.

IR (ATR): ṽ (% T)=3264 (m), 3080 (w), 1703 (s), 1606 (m), 1580 (m), 1507 (m), 1427 (m), 1413 (m), 1368 (s), 1322 (m), 1271 (m), 1220 (s), 1134 (m), 1094 (m), 976 (m), 914 (m), 881 (m), 846 (w), 765 (s), 712 (s) cm$^{-1}$.

EI-MS (EI+, 70 eV): m/z=398/400 (100) [M]$^{·+}$, 370/372 (20), 314/316 (19), 207 (17), 179 (18), 150/152 (18).

HRMS (ESI−) calc. for C$_{18}$H$_6$$^{79}$BrO$_6$ [M−H]$^−$: 396.9353. found 396.9365 amu.

(1→2)-Abeo-chartarin (67)

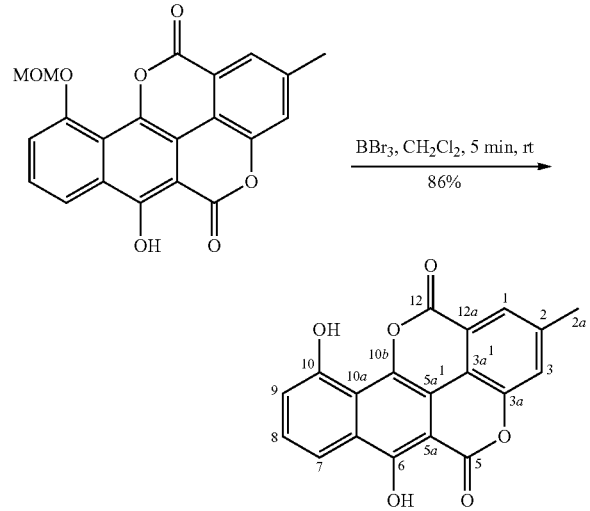

This compound was prepared as a yellow solid in 86% yield by the reaction of (62) according to the general procedure for MOM-deprotection as described.

$R_f$ silicagel 60; chloroform/methanol 95:5=0.95.

mp. 330° C.→brown; 339° C.→dark brown; 346-367° C.→melting.

$^1$H NMR (600 MHz; CD$_2$Cl$_2$): see Table 12.

$^{13}$C NMR (150 MHz; CD$_2$Cl$_2$): see Table 13.

IR (ATR): ṽ (% T)=3246 (w), 3066 (w), 2915 (w), 1691 (s), 1626 (m), 1519 (m), 1453 (m), 1413 (m), 1371 (s), 1335 (s), 1276 (s), 1227 (s), 1121 (m), 1056 (m), 1029 (m), 980 (m), 945 (m), 884 (m), 768 (s), 714 (s) cm$^{-1}$.

EI-MS (EI+, 70 eV): m/z=334 (100) [M]$^{•+}$, 306 (20), 278 (9), 250 (16), 165 (13).

HRMS (ESI−) calc. for C$_{19}$H$_9$O$_6$ [M−H]$^−$: 333.0412. found 333.0405 amu.

(1→2)-Abeo-homochartarin (68)

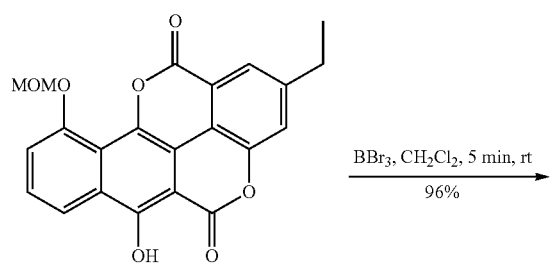

This compound was prepared as a yellow solid in 96% yield by the reaction of (63) according to the general procedure for MOM-deprotection as described.

$R_f$ silicagel 60; chloroform/methanol 95:5=0.95.

mp. 306° C.

$^1$H NMR (600 MHz; CD$_2$Cl$_2$): see Table 12.

$^{13}$C NMR (150 MHz; CD$_2$Cl$_2$): see Table 13.

IR (ATR): ṽ (% T)=3238 (m), 2968 (w), 2933 (w), 2879 (w), 1692 (s), 1618 (m), 1522 (m), 1453 (m), 1415 (m), 1373 (s), 1330 (s), 1283 (s), 1225 (s), 1135 (m), 1063 (m), 979 (m), 925 (m), 885 (m), 766 (s), 719 (s) cm$^{-1}$.

EI-MS (EI+, 70 eV): m/z=348 (100) [M]$^{•+}$, 333 (38), 320 (8), 305 (17), 249 (11), 221 (6), 165 (7).

HRMS (ESI−) calc. for C$_{20}$H$_{11}$O$_7$ [M−H]$^−$: 347.0561. found 347.0571 amu.

(1→2)-Abeo-ethynylchartarin (69)

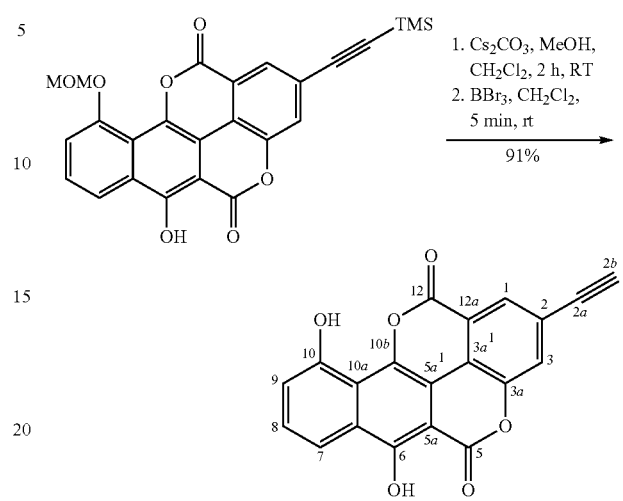

To a solution of (65) (131 mg, 283 μmol, 1 eq.) in dichloromethane (150 mL) a solution of caesium carbonate in methanol (30 mL, 10 mg/mL, 851 μmol, 3 eq.) was added. After 2 hours hydrochloric acid (100 mL, 1 N) was added. The organic phase was separated and the aqueous phase was further extracted twice with dichloro methane (100 mL) each. The combined organic phases were dried over sodium sulfate. TLC with chloroform indicates a spot at $R_f$=0.42 whereas the educt shows a $R_f$ value of 0.58. Also LC-MS analysis indicates the absence of the TMS-group ([M−H]$^−$ =387.0501 calc. for C$_{22}$H$_{11}$O$_7$ [M−H]$^−$: 387.0501 amu). The compound was used without further purification for cleavage of the MOM-group according to the general procedure for MOM-deprotection as described. The title compound was prepared as a yellow solid in 91% yield over both steps.

$R_f$ silicagel 60; chloroform/methanol 95:5=0.91.

mp. 240° C.→orange; 277° C.→brown; 0.397° C.→black.

$^1$H NMR (600 MHz; CD$_2$Cl$_2$): see Table 12.

$^{13}$C NMR (150 MHz; CD$_2$Cl$_2$): see Table 13.

IR (ATR): ṽ (% T)=3513 (w), 3270 (m), 3089 (w), 2962 (w), 1749 (s), 1698 (s), 1617 (m), 1579 (m), 1514 (s), 1453 (m), 1411 (m), 1353 (s), 1317 (s), 1251 (s), 1200 (s), 1133 (s), 1095 (s), 1048 (s), 975 (m), 931 (m), 896 (m), 815 (m), 770 (s), 716 (s) cm$^{-1}$.

EI-MS (EI+, 70 eV): m/z=344 (100) [M]$^{•+}$, 316 (17), 288 (7), 260 (19), 232 (9), 204 (5), 176 (11).

HRMS (ESI−) for C$_{20}$H$_7$O$_6$ [M−H]$^−$: 343.0248. found 343.0240 amu.

(1→2)-Abeo-chartreusin (70)

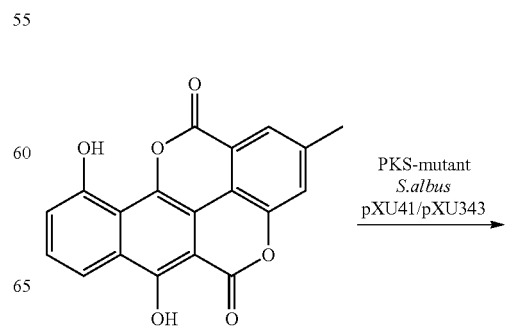

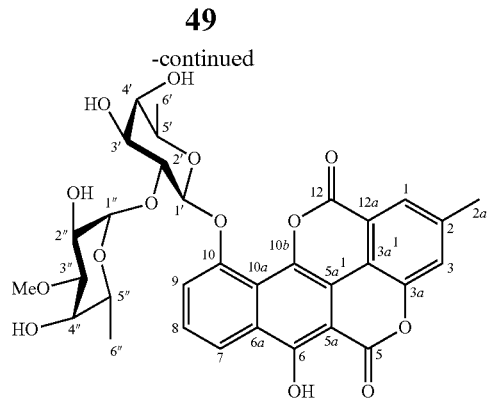

This compound was isolated as a yellow solid by fermentation of (67) according to the general procedure for fermentation and isolation as described.

$R_f$ silicagel 60; chloroform/methanol 95:5=0.74.
$^1$H NMR (600 MHz; pyridine-$D_5$): see Table 14a.
$^{13}$C NMR (150 MHz; pyridine-$D_5$): see Table 15a.
ESI-MS (ESI–): see Table 16.
ESI-MS$^2$ (ESI–): see Table 16.
HRMS (ESI–) calc. for $C_{32}H_{31}O_{14}$ [M–H]$^-$: 639.1719. found 639.1737 amu.

(1→2)-Abeo-homochartreusin (71)

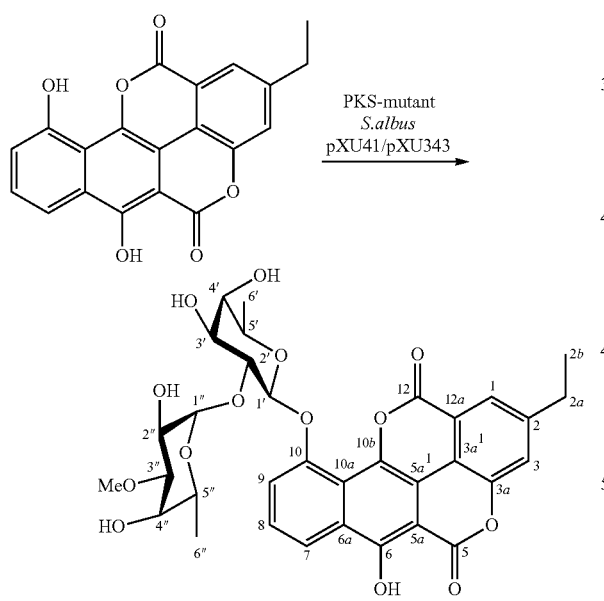

This compound was isolated as a yellow solid by fermentation of (68) according to the general procedure for fermentation and isolation as described.

$R_f$ silicagel 60; chloroform/methanol 95:5=0.75.
$^1$H NMR (600 MHz; pyridine-$D_5$): see Table 14a.
$^{13}$C NMR (150 MHz; pyridine-$D_5$): see Table 15a.
ESI-MS (ESI–): see Table 16.
ESI-MS$^2$ (ESI–): see Table 16.
HRMS (ESI–) calc. for $C_{33}H_{33}O_{14}$ [M–H]$^-$: 653.1876 found 653.1890 amu.

(1→2)-Abeo-bromochartreusin (72)

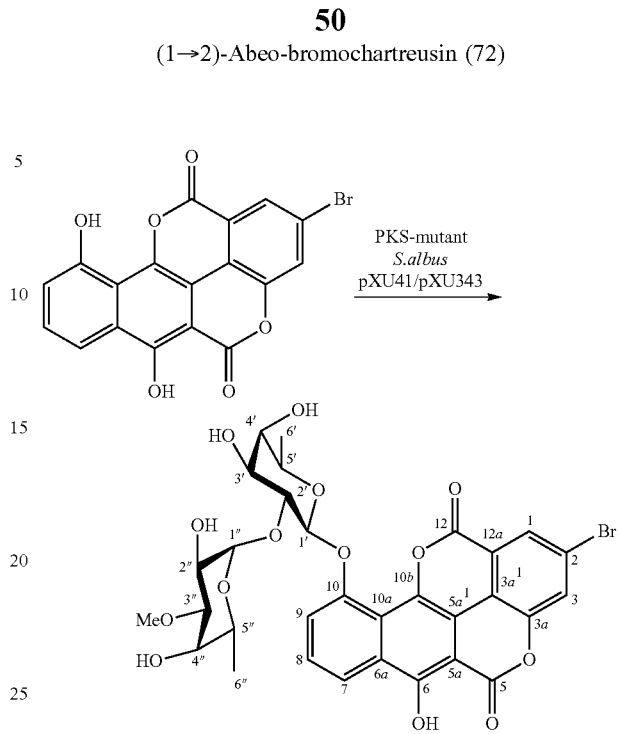

This compound was isolated as a yellow solid by fermentation of (66) according to the general procedure for fermentation and isolation as described.

$R_f$ silicagel 60; chloroform/methanol 95:5=0.70.
$^1$H NMR (600 MHz; pyridine-$D_5$): see Table 14b.
$^{13}$C NMR (150 MHz; pyridine-$D_5$): see Table 15b.
ESI-MS (ESI–): see Table 16.
ESI-MS$^2$ (ESI–): see Table 16.
HRMS (ESI–) calc. for $C_{31}H_{28}^{79}BrO_{14}$ [M–H]$^-$: 703.0668. found 703.0691 amu.

(1→2)-Abeo-ethynylchartreusin (73)

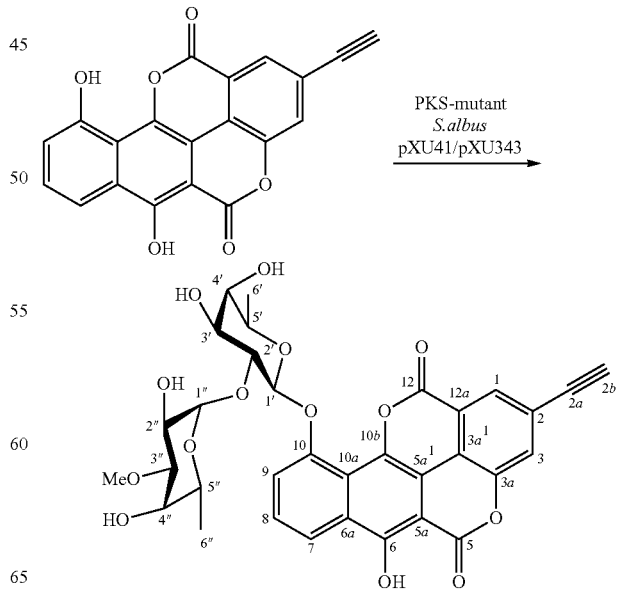

This compound was isolated as a yellow solid by fermentation of (69) according to the general procedure for fermentation and isolation as described.

$R_f$ silicagel 60; chloroform/methanol 95:5=0.66.

$^1$H NMR (600 MHz; pyridine-$D_5$): see Table 14b.

$^{13}$C NMR (150 MHz; pyridine-$D_5$): see Table 15b.

ESI-MS (ESI−): see Table 16.

ESI-MS$^2$ (ESI−): see Table 16.

HRMS (ESI−) calc. for $C_{33}H_{29}O_{14}$ [M−H]$^−$:649.1963. found 649.1561 amu.

(1→2)-Abeo-vinylchartreusin (74)

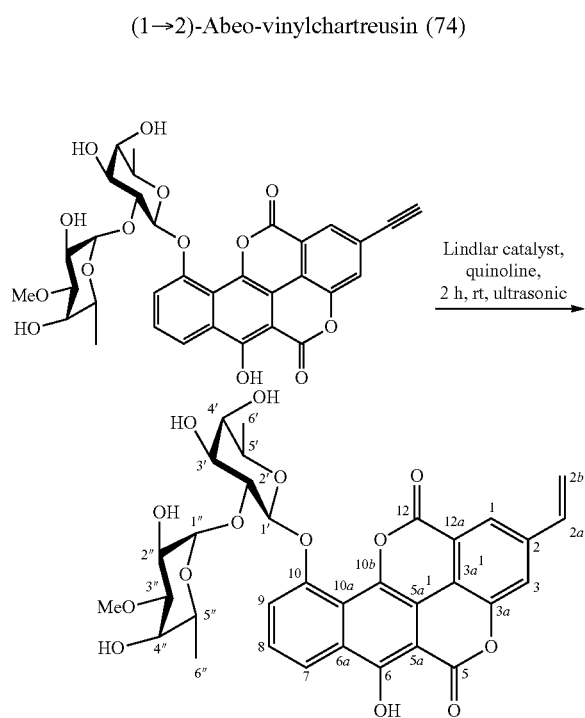

(1→2)-abeo-alkynylchartreusin (73) (4 mg, 6.15 μmol) was dissolved in 25 mL methanol. The solution was degassed in a temperature controlled ultrasonic bath at 20° C. while argon was bubbled through the solution. After 10 min of degassing a suspension of Lindlar catalyst (2 mg, Aldrich) and quinolone (17.2 μL) in methanol (600 μL) was added. Then hydrogen was passed through the suspension while temperature controlled sonication. After 2 h the suspension was passed through a 0.2 μm PTFE filter membrane. HPLC-MS analysis showed total alkinine conversion. Beside to the vinyl product the corresponding ethyl derivative (71) could be detected. The ratio was determined as 8.2:1 (HPLC, $\lambda_{max}$=410 nm, vinyl/ethyl). The final purification was carried out using preparative HPLC yielding 2.3 mg (57%) of the desired vinyl derivative.

$R_f$ silica gel 60; chloroform/methanol 95:5=0.64.

$^1$H NMR (600 MHz; pyridine-$D_5$): see Table 14b.

$^{13}$C NMR (150 MHz; pyridine-$D_5$): see Table 15b.

ESI-MS (ESI−): see Table 16.

ESI-MS$^2$ (ESI−): see Table 16.

HRMS (ESI−) calc. for $C_{33}H_{31}O_{14}$ [M−H]$^−$: 651.1719. found. 651.1722 amu.

Methyl 2-formyl-3,6-dihydroxybenzoate (31)

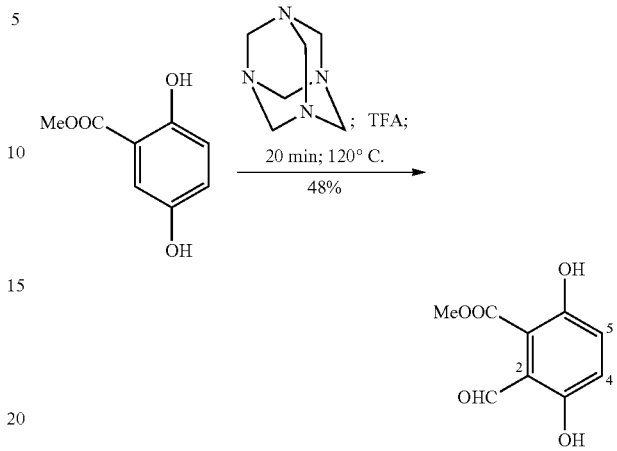

Methyl 2-bromo-5-hydroxybenzoate (29) (500 mg, 3.29 mM, 1 eq.) and hexamethylenetetraamine (9.21 mg, 65.7 mM, 2 eq.) were placed in a 6 mL Biotage® microwave vial and treated with trifluoroacetic acid (5 mL) and sealed. The slurry was heated for 15 min in an aluminum block at 110° C. After cooling the resulting yellow liquid was poured into water and neutralized with sodium bicarbonate. The aqueous phase was extracted trice with ethyl acetate. The crude extract was dried over sodium sulfate, concentrated and subjected to column chromatography with a gradient from cyclohexane to cyclohexane/ethyl acetate 7:1. The fractions containing the product yield pure methyl 2-formyl-3,6-dihydroxybenzoate (72) (286 mg, 1.59 mmol, 48%).

$R_f$ Silica gel 60; chloroform/methanol 95:5=0.63.

mp. 102.9-103.6° C.

$^1$H NMR (300 MHz; CDCl$_3$): δ=12.09 (s, 1H, OH-6), 10.56 (s, 1H, OH-3), 10.43 (s, 1H, CHO), 7.15 (d, 1H, $^3J_{H-H}$=9.3 Hz, CH-5), 7.08 (d, 1H, $^3J_{H-H}$=9.3 Hz, CH-4), 3.97 (s, 3H, OCH$_3$) ppm.

$^{13}$C NMR (75 MHz; CDCl$_3$): δ=196.8 (CHO), 169.9 (COOMe), 157.7 (C-3-OH), 156.0 (C-6-OH), 128.2 (CH-5), 126.6 (CH-4), 116.2 (C-2), 109.8 (C-1), 53.1 (OCH$_3$) ppm.

IR (ATR): ṽ ($T_{rel}$)=3083 (w), 3029 (w), 2958 (w), 2923 (w), 2852 (w), 1666 (m), 1637 (s), 1587 (m), 1443 (s), 1400 (m), 1329 (s), 1280 (s), 1194 (s), 1163 (s), 1132 (s), 1025 (m), 931 (s), 844 (s), 802 (s), 748 (s), 709 (s) cm$^{-1}$.

EI-MS (EI+, 70 eV): m/z=196 (78), 181 (17), 164 (73), 150 (17), 136 (100), 119 (16), 108 (97), 79 (11).

HRMS (ESI+) calc. for $C_9H_7O_5$ [M+H]$^+$=195.0299. found: 195.0295.

Methyl 6-hydroxy-coumarin-5-carboxylate (33)

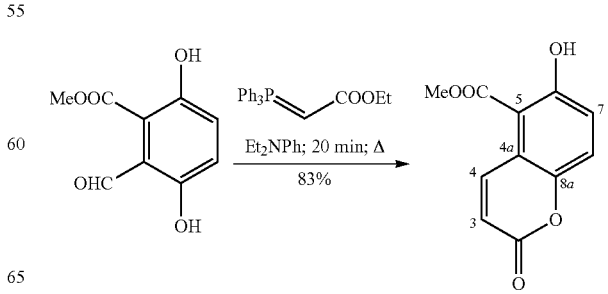

Methyl 2-formyl-3,6-dihydroxybenzoate (29) (100 mg, 510 µmol, 1.0 eq.) and carboxymethylphosphorane (195 mg, 561 µmol, 1.1 eq.) were placed in a Schlenk tube, flushed with argon three times and dissolved in N,N-dimethylaniline (1.6 mL) The mixture was heated while refluxing at a cooling finger for 20 min, cooled to rt, dissolved in ethyl acetate and extracted twice with 2 N hydrochloric acid, sodium bicarbonate solution and dried over sodium sulfate. The resulting solid was subjected to column chromatography with a gradient from cyclohexane to cyclohexane/ethyl acetate 7:1 yielding the title compound as pale yellow solid (93 mg, 422 µmol, 83%).

$R_f$ Silica gel 60, chloroform/methanol 95:5=0.94
mp. 159.3-160.6° C.
$^1$H NMR (300 MHz; CDCl$_3$): δ=see Table 17a.
$^{13}$C NMR (75 MHz; CDCl$_3$): δ=see Table 18.
IR (ATR): ṽ ($T_{rel}$)=3117 (w), 3074 (m), 2950 (m), 2922 (m), 2852 (w), 1811 (w), 1715 (s), 1662 (s), 1563 (m), 1440 (s), 1330 (s), 1184 (s), 1123 (s), 1031 (s), 963 (m), 938 (m), 898 (s), 831 (s), 760 (s) cm$^{-1}$.
EI-MS (EI+, 70 eV): m/z=220 (43), 188 (100), 160 (55), 132 (33), 76 (15).
HRMS calc. for (ESI−) for C$_9$H$_7$O$_5$ [M−H]$^-$: 195.0299. found: 195.0295.

Methyl 6-(methoxymethoxy)-coumarin-5-carboxylate (34)

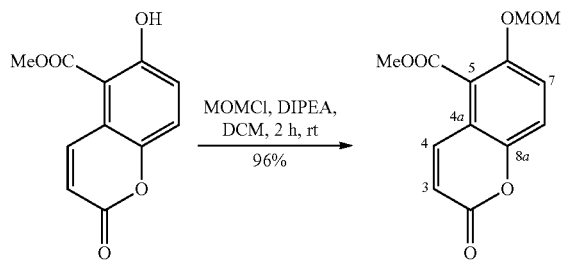

Methyl 6-hydroxy-coumarin-5-carboxylate (33) (200 mg, 0.91 mmol, 1 eq.) and Hünigs base (300 µL, 1.8 mmol, 2 eq.) were dissolved in 5 mL dichloromethane. The mixture was treated with methoxymethyl chloride (114 µL, 1.8 mmol, 2 eq.) and stirred for 2 h. The solution was treated with water (50 mL) and extracted with ethyl acetate (50 mL). The organic phase was extracted with a sodium hydroxide solution (1 mol·L$^{-1}$) dried with sodium sulfate and concentrated to yield the title product as pale yellow solid (230 mg, 0.87 mmol, 96%).

$R_f$ Silica gel 60; dichloromethane: 0.18.
mp. 126.8-127.2° C.
$^1$H NMR (300 MHz; CDCl$_3$): δ=see Table 17a.
$^{13}$C NMR (75 MHz; CDCl$_3$): δ=see Table 18.
IR (ATR): ṽ ($T_{rel}$)=3435 (w), 3096 (w), 3053 (w), 3000 (w), 2952 (w), 2916 (w), 2832 (w), 1718 (s), 1603 (m), 1567 (m), 1469 (m), 1422 (m), 1282 (m), 1251 (m), 1210 (s), 1154 (s), 1113 (m), 1091 (m), 1038 (s), 1002 (s), 921 (m), 891 (s), 839 (m), 820 (s), 765 (m), 694 (m), 650 (m), 604 (m) cm$^{-1}$.
EI-MS (EI+, 70 eV): m/z=264 (57), 234 (96), 203 (32), 188 (100), 175 (34), 160 (75), 132 (66), 76 (55).
HRMS calc. for (ESI+) for C$_{11}$H$_9$O$_5$ [M+H]$^+$: 221.0444. found: 221.0446.

Methyl 6-(methoxy)-coumarin-5-carboxylate (35)

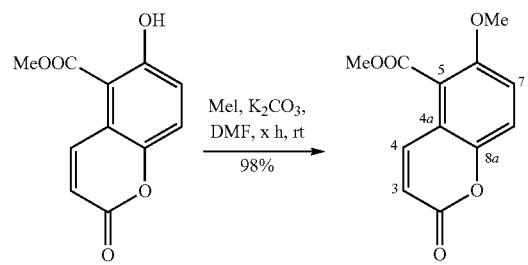 [SMILES: COC(=O)c1c(O)ccc2oc(=O)ccc12 ; COC(=O)c1c(OC)ccc2oc(=O)ccc12]

Methyl 6-hydroxy-coumarin-5-carboxylate (33) (264 mg, 1.20 mmol, 1 eq.) and potassium carbonate (330 mg, 2.4 mmol, 2 eq.) were suspended in 6 mL DMF and cooled to 0° C. in an ice bath. The mixture was treated with methyl iodide and stirred for 2 h while warming up to rt. The solution was treated with water (50 mL) and extracted tree times with ethyl acetate (50 mL each). The organic phase was dried over sodium sulfate and concentrated to yield the title product as pale yellow solid. (274 mg, 1.17 mmol, 98%).

$R_f$ Silica gel 60, dichloromethane: 0.15.
mp. 161.3-161.6° C.
$^1$H NMR (300 MHz; CDCl$_3$): δ=see Table 17a.
$^{13}$C NMR (75 MHz; CDCl$_3$): δ=see Table 18.
IR (ATR): ṽ ($T_{rel}$)=3097 (w), 3013 (w), 2952 (w), 2917 (w), 2844 (w), 1703 (s), 1569 (m), 1464 (m), 1380 (m), 1283 (s), 1244 (s), 1188 (s), 1118 (s), 1073 (s), 1020 (s), 948 (m), 915 (m), 884 (m), 820 (s), 689 (m), 623 (m) cm$^{-1}$.
EI-MS (EI+, 70 eV): m/z=234 (100), 203 (74), 175 (71), 160 (22), 147 (14), 132 (15), 119 (14), 117 (13), 103 (7), 91 (14), 89 (15), 77 (17), 76 (17), 63 (15).
HRMS (ESI+) calc. for C$_{12}$H$_{11}$O$_5$ [M+H]$^+$: 235.0601. found 235.0597.

Methyl 6-(trifluoromethylsulfonyloxy)-coumarin-5-carboxylate (36)

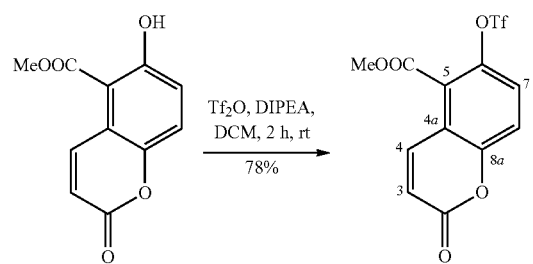 [SMILES: COC(=O)c1c(O)ccc2oc(=O)ccc12 ; COC(=O)c1c(OS(=O)(=O)C(F)(F)F)ccc2oc(=O)ccc12]

Methyl 6-hydroxy-coumarin-5-carboxylate (33) (1 g, 4.54 mmol, 1 eq.) was placed in a Schlenk tube and flushed with argon three times. Then dichloromethane (60 mL), Hünigs base (2.7 mL, 16.3 mmol, 3.6 eq.) and trifluoromethanesulfonic anhydride (0.92 mL, 5.4 mmol, 1.2 eq.) were added. The solution was stirred for 2 h at rt. Then additional trifluoromethanesulfonic anhydride (0.2 mL, 1.5 mmol, 0.3 eq.) was added. The solution was stirred for further 1 h. The solution was extracted with saturated ammonium chloride solution and dried over sodium sulfate. The crude product was filtered through a silica gel pad and recrystallized from methanol/water, yielding the title compound as pale yellow crystals (1.24 g, 3.5 mmol, 78%).

$R_f$ Silica gel 60; dichloromethane: 0.41.

mp. 93.7-94.4° C.

$^1$H NMR (300 MHz; CDCl$_3$): δ=see Table 17a.

$^{13}$C NMR (75 MHz; CDCl$_3$): δ=see Table 18.

IR (ATR): $\tilde{v}$ ($T_{rel}$)=3435 (w), 3096 (w), 3000 (w), 2916 (w), 2832 (w), 2073 (w), 1718 (s), 1630 (w), 1567 (m), 1469 (m), 1454 (m), 1376 (w), 1326 (m), 1282 (m), 1210 (s), 1091 (m), 1038 (s), 938 (m), 839 (m), 820 (s), 784 (m), 765 (m), 743 (m), 694 (m), 650 (m), 626 (m), 604 (m) cm$^{-1}$.

EI-MS (EI+, 70 eV): m/z=352 (42), 321 (18), 219 (100), 191 (23), 188 (26), 175 (39), 160 (51), 132 (27), 119 (18), 91 (24).

HRMS calc. for (ESI+) for C$_{12}$H$_8$O$_7$F$_3$S [M+H]$^+$: 352.9937. found: 352.9940.

Methyl 6-((trimethylsilyl)ethynyl)-coumarin-5-carboxylate (37)

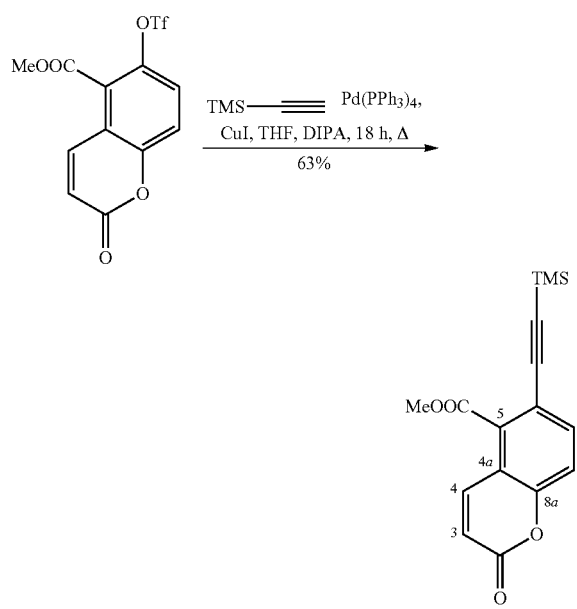

Methyl 6-(trifluoromethylsulfonyloxy)-coumarin-5-carboxylate (29) (500 mg, 1.42 mmol, 1 eq.), copper(I)iodide (27 mg, 142 μmol 0.1 eq.) and tetrakis(triphenylphosphine)-palladium(0) (164 mg, 142 μmol, 0.1 eq.) were placed into a Schlenk tube and flushed with argon 3 times. Then 40 mL of a degassed mixture of diethylamine and THF (1:1, v/v) was added followed by trimethylsilylacetylene (401 μL, 2.84 mmol, 2 eq.). The mixture was stirred overnight while refluxing. Two and four hours after starting the reaction further trimethylsilylacetylene (2 eq.) was added. After cooling the mixture was quenched with 1 mol·L$^{-1}$ hydrochloric acid. The solution was extracted trice with diethyl ether. The combined organic phases were dried over sodium sulfate concentrated and subjected to column chromatography with a gradient from pentane to cyclohexane/ethyl acetate 9:1. The title compound was isolated as a pale yellow solid. (269.7 mg 89.8 μmol, 63%)

$R_f$ Silica gel 60; dichloromethane: 0.25.

mp. 122.4-123.7° C.

$^1$H NMR (300 MHz; CDCl$_3$): δ=see Table 17a.

$^{13}$C NMR (75 MHz; CDCl$_3$): δ=see Table 18.

IR (ATR): $\tilde{v}$ ($T_{rel}$)=2953 (m), 2921 (m), 2851 (w), 2154 (w), 1714 (s), 1568 (m), 1463 (m), 1445 (m), 1325 (m), 1287 (m), 1248 (s), 1183 (m), 1108 (m), 1030 (m), 978 (m), 927 (m), 843 (s), 759 (s), 710 (m), 648 (m) cm$^{-1}$.

EI-MS (EI+, 70 eV): m/z=300 (23), 285 (26), 255 (100), 227 (22).

HRMS (ESI+) calc. for C$_{16}$H$_{17}$O$_4$Si [M+H]$^+$: 301.0902. found: 301.0892 amu.

10-MOM-Methoxymethylchartarin (39)

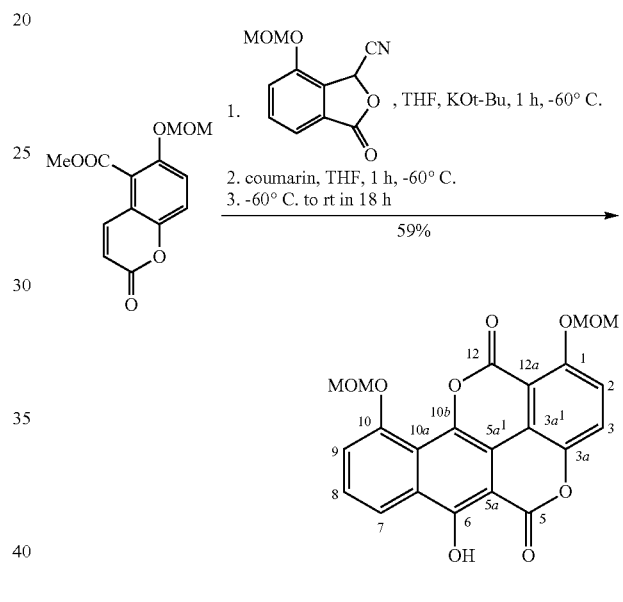

This compound was prepared in analogy to general protocol using 22 and 34. (yellow solid, 59% yield) This compound was used without further purification or analysis.

EI-MS (EI+, 70 eV): m/z=424 (71), 394 (52), 380 (30), 364 (20), 350 (100), 348 (74), 335 (53), 321 (27), 307 (47).

HRMS (ESI-) calc. for C$_{22}$H$_{15}$O$_9$ [M-H]$^-$: 423.0722. found: 423.0732.

10-MOM-Methoxychartarin (40)

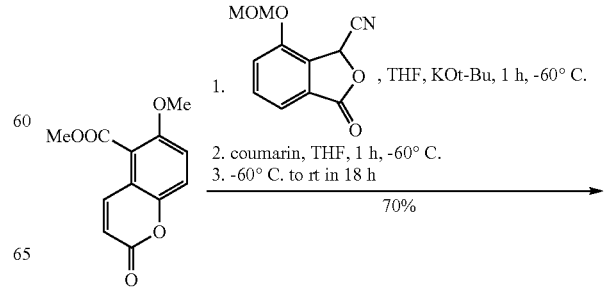

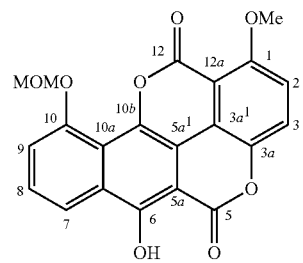

This compound was prepared in analogy to general protocol using 22 and 35. (yellow solid, 70% yield) This compound was used without further purification or analysis.

HRMS (ESI−) calc. for $C_{21}H_{13}O_8$ [M−H]$^−$: 393.0616. found: 393.0627.

10-MOM-TMS-Ethynylchartarin (41)

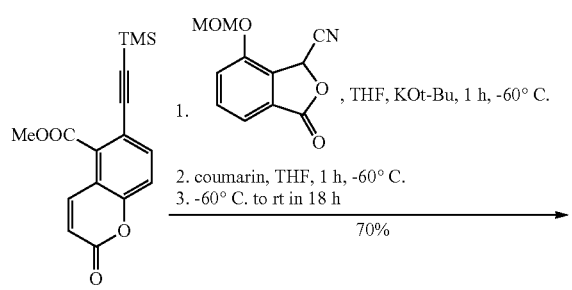

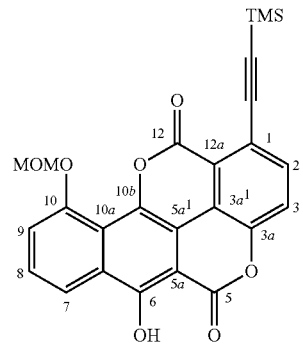

This compound was prepared in analogy to general protocol using 22 and 37. (yellow solid, 70% yield)

mp. 223.7-224.9° C.

$^1$H NMR (300 MHz; CDCl$_3$): δ=see Table 20.

$^{13}$C NMR (75 MHz; CDCl$_3$): δ=see Table 4.

IR (ATR): ṽ ($T_{rel}$)=2957 (w), 1742 (m), 1695 (m), 1594 (w), 1497 (m), 1369 (m), 1234 (s), 1146 (s), 1067 (m), 1004 (s), 924 (m), 841 (s), 766 (s), 674 (m) cm$^{−1}$.

EI-MS (EI+, 70 eV): m/z=460 (50), 445 (42), 430 (47), 415 (43), 400 (37), 372 (30), 356 (100).

HRMS (ESI−) calc. for $C_{25}H_{19}O_7Si$ [M−H]$^−$: 459.0895. found: 495.0915 amu.

1-Hydroxychartarin (43)

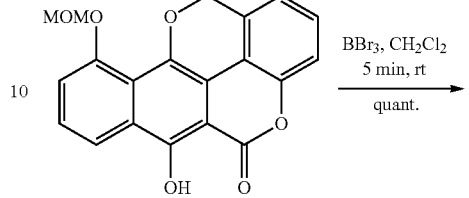

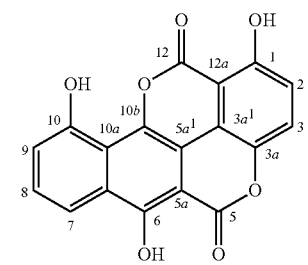

This compound was prepared in analogy to general protocol using 39. (yellow solid, quant. yield) This compound was used without further purification or analysis.

ESI-MS (ESI+): m/z=336 (100), 308 (12), 280 (15), 252 (15), 224 (8), 196 (6), 168 (9), 139 (9).

HRMS (ESI−) calc. for $C_{18}H_7O_7$ [M−H]$^−$: 335.0186. found 335.0200.

1-Methoxychartarin (44)

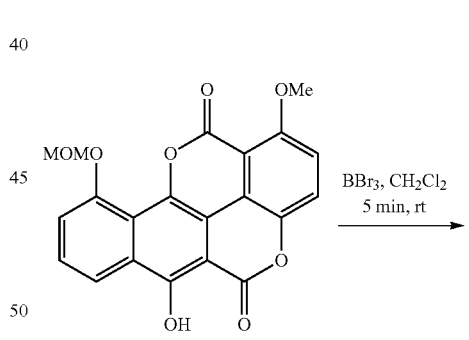

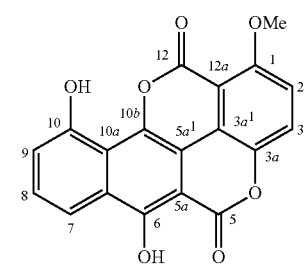

This compound was prepared in analogy to general protocol using 40. (yellow solid) This compound was used without further purification or analysis.

HRMS (ESI−) calc. for $C_{19}H_9O_7$ [M−H]$^−$: 349.0354. found: 349.0360.

Ethynylchartarin (45)

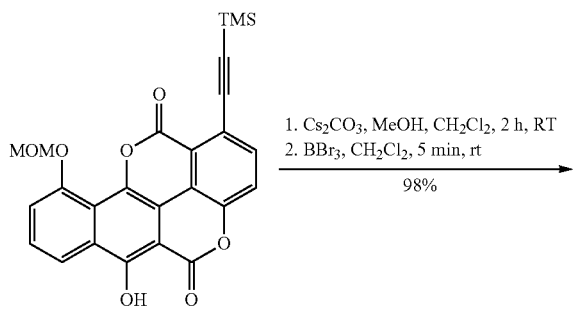

This compound was prepared in analogy to 69 using 41. (yellow solid, 98% yield)

mp. >410° C.

$^1$H NMR (300 MHz; CDCl$_3$): δ=see Table 19.

$^{13}$C NMR (75 MHz; CDCl$_3$): δ=see Table 2.

IR (ATR): ṽ (T$_{rel}$)=3460 (w), 3249 (m), 1755 (m), 1698 (s), 1584 (m), 1496 (m), 1366 (s), 1293 (m), 1232 (s), 1096 (s), 1051 (s), 946 (m), 840 (m), 771 (s), 731 (m), 672 (s) cm$^{-1}$.

EI-MS (EI+, 70 eV): m/z=344 (100), 316 (26), 288 (10), 260 (20), 232 (13), 204 (8), 176 (16), 150 (9).

HRMS (ESI−) calc. for C$_{20}$H$_7$O$_6$ [M−H]$^-$: 343.0248. found: 343.0251 amu.

Hydroxychartreusin (47)

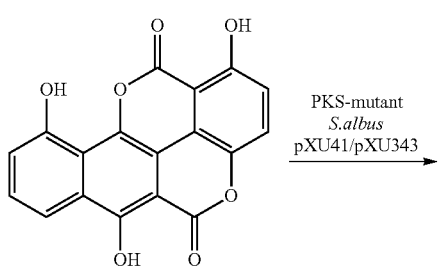

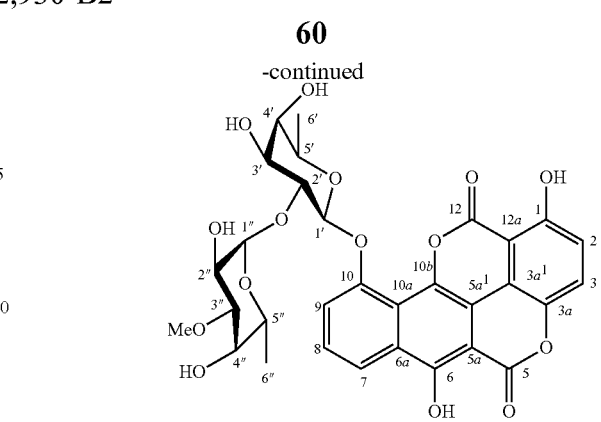

This compound was isolated as a yellow solid by fermentation of 43 according to the general procedure for fermentation and isolation as described.

R$_f$ Silica gel 60; chloroform/methanol 95:5=0.2.

$^1$H NMR (600 MHz; pyridine-D$_5$): see Table 21.

$^{13}$C NMR (150 MHz; pyridine-D$_5$): see Table 22.

ESI-MS (ESI−): see Table 7.

ESI-MS$^2$ (ESI−): see Table 7.

HRMS (ESI−) for C$_{31}$H$_{29}$O$_{15}$ [M−H]$^-$ 641.1512. found: 641.1542.

Methoxychartreusin (48)

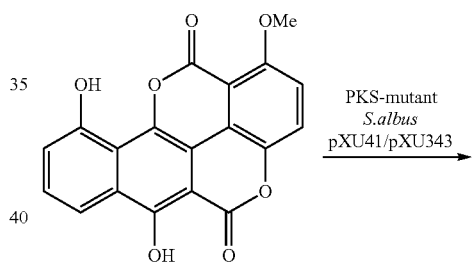

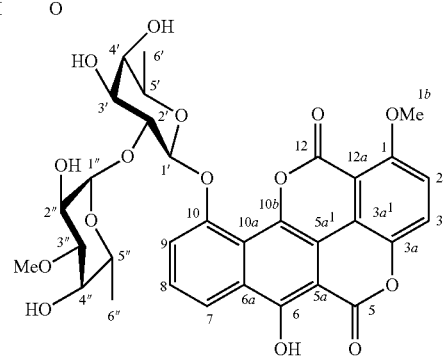

This compound was isolated as a yellow solid by fermentation of 44 according to the general procedure for fermentation and isolation as described.

R$_f$ Silica gel 60; chloroform/methanol 95:5=0.2.

$^1$H NMR (600 MHz; pyridine-D$_5$): see Table 21.

$^{13}$C NMR (150 MHz; pyridine-D$_5$): see Table 22.

ESI-MS (ESI−): see Table 7.

ESI-MS$^2$ (ESI−): see Table 7.

HRMS (ESI−) for C$_{32}$H$_{31}$O$_{15}$ [M−H]$^-$ 655.1668. found: 655.1691.

Ethynylchartreusin (49)

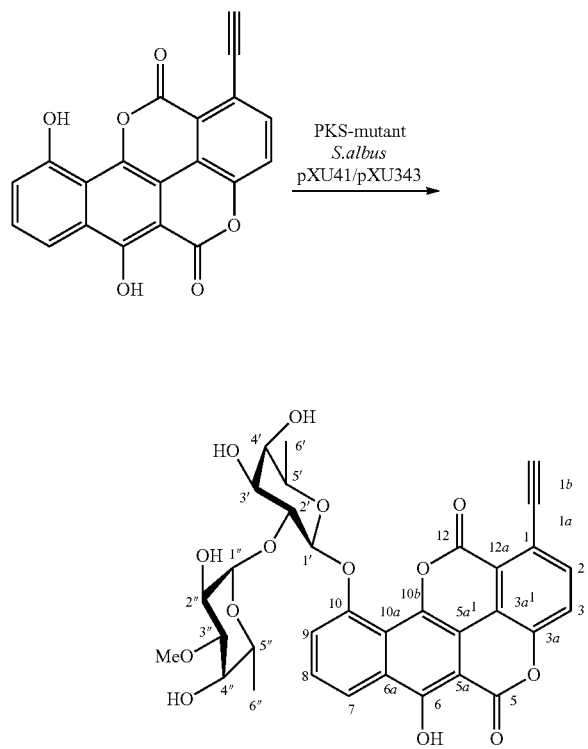

This compound was isolated as a yellow solid by fermentation of 45 according to the general procedure for fermentation and isolation as described.

$R_f$ Silica gel 60; chloroform/methanol 95:5=0.07.

$^1$H NMR (600 MHz; pyridine-$D_5$): see Table 21.

$^{13}$C NMR (150 MHz; pyridine-$D_5$): see Table 22.

ESI-MS (ESI−): see Table 7.

ESI-MS$^2$ (ESI−): see Table 7.

HRMS (ESI−) for $C_{33}H_{29}O_{14}$ [M−H]$^-$ 649.1552. found: 649.1574.

Chartarin-1,10 bis-1,4'-bipiperidine-1'-carboxylate

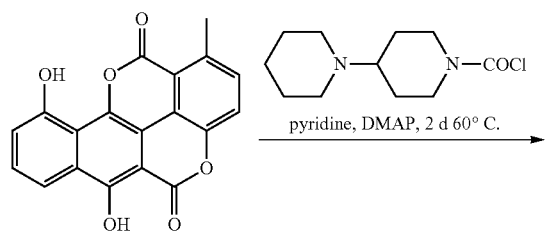

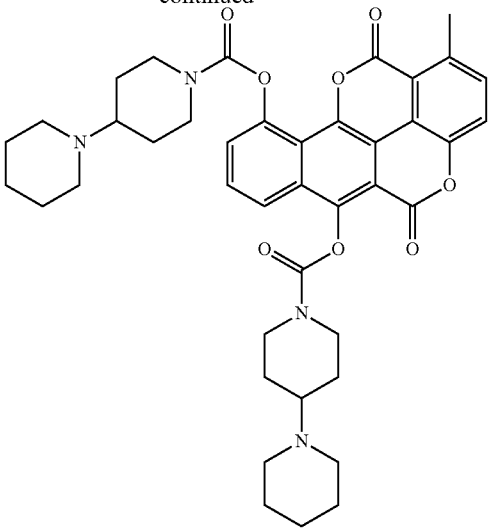

Chartarin (1.0 eq.) 1,4'-bipiperidine-1'-carbonyl chloride (4.0 eq.), N,N-dimethylpyridin-4-amine was placed in a Schlenk tube and flushed with argon 3 times. Then pyridin was added and the solution was stirred for 2 days at 60° C. After cooling the solvent was removed and the resulting brownish solid was dissolved in Methanol/THF. The solution was suspected to preparative HPLC using a Phenomenex Kinetix XB-C18 column with a gradient from 10 to 83% acetonitrile in water with 0.1% formic acid.

HRMS (ESI+) calc. for $C_{43}H_{47}O_8N_4$ [M+H]$^+$: 723.3402. found. 723.3395 amu.

Bromchartarin-1,10 bis-1,4'-bipiperidine-1'-carboxylate

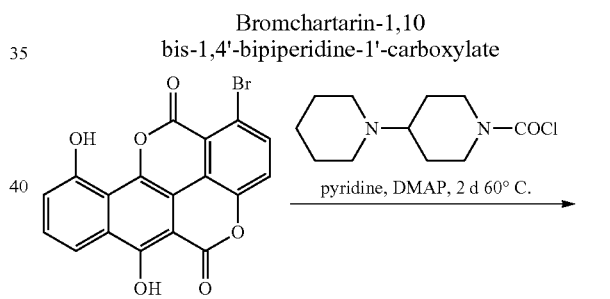

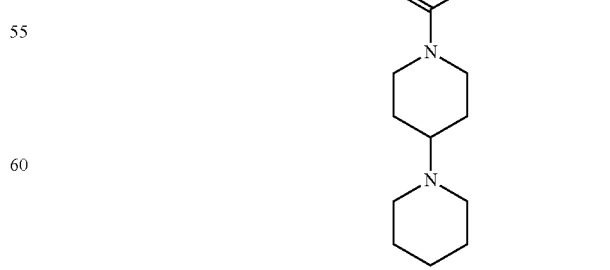

Preparation see Chartarin-1,10 bis-1,4'-bipiperidine-1'-carboxylate

HRMS (ESI+) ber. für $C_{40}H_{44}{}^{79}BrO_8N_4$ [M+H]$^+$: 787, 2337, gef. 787, 2333.

Norchartarin-1,10 bis-1,4'-bipiperidine-1'-carboxylate and vinylchartarin-1,10 bis-1,4'-bipiperidine-1'-carboxylate

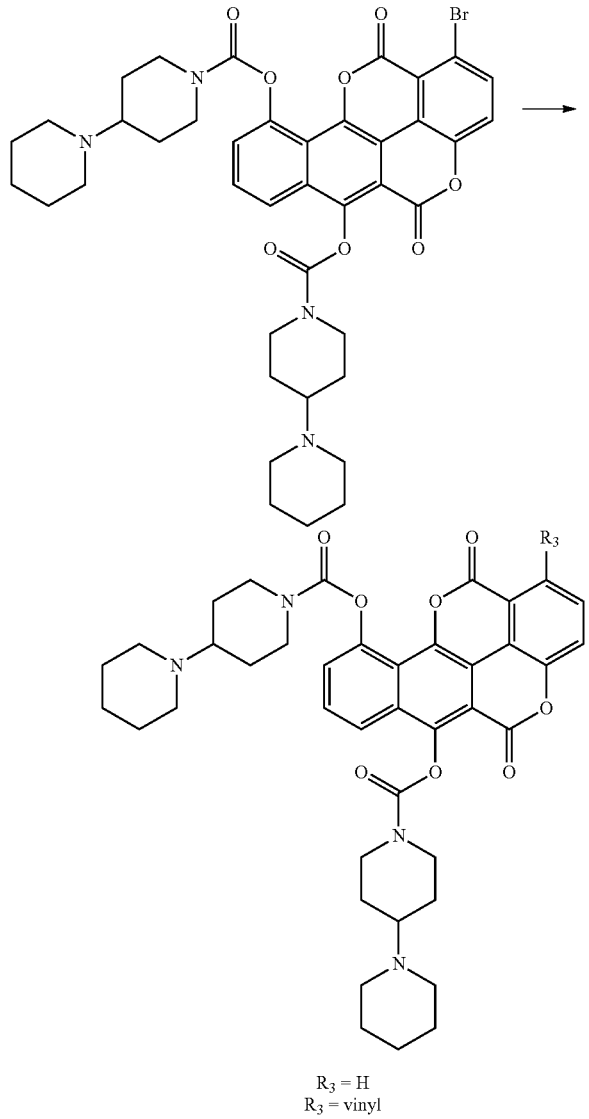

R$_3$ = H
R$_3$ = vinyl

1-Bromochartarin (1.0 eq.), lithium chloride (5 eq.) and dichloro(1,3-bis(diphenylphosphino) propane) palladium (0.1 eq.) were placed in a Schlenk tube, evacuated and flushed with argon for three times. Under argon counter flow dried DMF and tri-n-butyl(vinyl)tin (5 eq.) were added. The Schlenk tube was equipped with a cooling finger and stirred at 90° C. for 3 h. After cooling the solvent was removed and the resulting brownish solid was dissolved in Methanol/THF. The solution was suspected to preparative HPLC using a Phenomenex Kinetix XB-C18 column with a gradient from 10 to 83% acetonitrile in water with 0.1% formic acid. Both compounds were isolated in a ratio 1:4 as H:vinyl.

HRMS (ESI+) calc. for $C_{40}H_{45}O_8N_4$ [M+H]$^+$: 709.3232. found. 709.3228 amu.

HRMS (ESI+) calc. for $C_{42}H_{47}O_8N_4$ [M+H]$^+$: 735.3388. found. 735.3385 amu.

Determination of Growth Inhibition and Cytotoxicity of HUVEC, K-562 and HeLa

Compounds were assayed against human umbilical vein endothelial cells HUVEC (ATCC CRL-1730) and human chronic myeloid leukemia cells K-562 (DSM ACC 10) for their antiproliferative effects (GI$_{50}$) and against human cervix carcinoma cells HeLa (DSM ACC 57) for their cytotoxic effects (CC$_{50}$) as previously described (Scherlach, K., Partida-Martinez, L. P., Dahse, H. M. & Hertweck, C. Antimitotic rhizoxin derivatives from a cultured bacterial endosymbiont of the rice pathogenic fungus Rhizopus microsporus. Journal of the American Chemical Society 128, 11529-11536 (2006)).

Determination of Growth Inhibition of Hs27 in the Presence or Absence of Light

The Hs27 foreskin fibroblast cells (ATCC, CRL-1634) were grown in RPMI 1640 (CAMBREX 12-167F) supplemented with 500 µl/l gentamicin sulfate (Cambrex 17-518Z), 10% heat inactivated fetal bovine serum (PAA A15-104), at 37° C. in plastic flasks (NUNC) in a humidified atmosphere containing 5% $CO_2$.

The adherent cells of Hs27 were harvested at the logarithmic growth phase after soft trypsinization using 0.25% trypsin in PBS containing 0.02% EDTA (Biochrom KG L2163).

Hs27 cells were seeded with 1×10$^4$ cells per 0.1 mL per well of the 96-well microplates (NUNC 167008). Then, the plates were prepared with dilutions of the compounds.

The influence of the different dilutions of compounds in the absence or presence of light (distance to the cells: 4 cm) were assayed for 72 hours at 37° C. in a humidified atmosphere containing 5% $CO_2$. After incubation time, the effect of compounds in the absence or presence of light were analyzed in compare to negative control.

For this, the adherent Hs27 cells were fixed by glutaraldehyde (MERCK 1.04239.0250) and stained with a 0.05% solution of methylene blue (SERVA 29198) for 15 min. After gentle washing, the stain was eluted by 0.2 mL of 0.33 N HCl in the wells. The optical densities were measured at 660 nm in a microplate reader (Tecan "Sunrise", Austria). Under the experimental conditions, the signals from the methylene blue are proportional to the number of viable cells.

Determination of Growth Inhibition of HT-29 and MEL-HO in the Presence or Absence of Light The human HT-29 colon adenocarcinoma cells (ACC 299) and the human MEL-HO (ACC 62) melanoma cells were grown as previously described (Ueberschaar, N.; Dahse, H.-M.; Bretschneider, T.; Hertweck, C. Angew. Chem. Int. Ed. 2013, 52, 6185-6189).

Whereas the antiproliferative effect of chartreusin, (1→2) abeo vinylchartreusin, (1→2)abeo-ethynylchartreusin, and vinylchartreusin against colon adenocarcinoma cell line HT-29 is rather low in the absence of light (7.0-9.4 µM), incubation in the presence of the blue LED substantially increased the activity of (1→2) abeo vinylchartreusin (GI$_{50}$ 3.1 µM vs. 9.4 µM) and vinylchartreusin (GI$_{50}$ 0.6 µM vs. 7.1 µM). Similarly, the activity of (1→2)abeo ethynylchartreusin was 5-fold higher in the presence of light (GI$_{50}$ 1.7 µM vs. GI$_{50}$ 8.6 µM):

| Compound | without light GI$_{50}$ [µM] | with light GI$_{50}$ [µM] |
|---|---|---|
| chartreusin | 7.96 | 7.65 |
| vinylchartreusin | 7.05 | 0.61 |

-continued

| Compound | without light GI$_{50}$ [μM] | with light GI$_{50}$ [μM] |
|---|---|---|
| (1→2) abeo-vinylchartreusin | 9.35 | 3.06 |
| (1→2) abeo-etynylchartreusin | 8.61 | 1.69 |

DNA Adduct Formation

500 μL of herring sperm DNA (5 mg/mL in PBS-buffer, pH 7.5) were threaded with 20 μL (1 mg/mL in DMSO) substrate. The solution was stirred for 1 h at RT and then irradiated for 3 min with a laser (λ=405 nm, P=20 mW). Then 500 μL 6N hydrochloric acid were added and the solution was heated in a closed HPLC vial for 4 min at 100° C. The solution was freeze dried. The residue was dissolved in methanol and suspected to LC-HRMS.

UV-VIS Titration of Chartreusin and its Analogues

A 1 mg/mL solution of chartreusin or its analogs in DMSO was diluted to 1 mL with PBS-buffer (pH 7.5) to a final concentration of 50 μmol/L in a fused quartz cuvette. Then a 10 mg/mL herring sperm DNA solution (GC content≈43%, M$_{middle}$=649.66 g/mol) in PBS buffer was added to give the ratios substrate: DNA as 1:0, 1:0.5, 1:1, 1:2, 1:5, 1:10, 1:20, 1:30, 1:50 and 1:100. After each dilution step a UV-VIS spectrum between 300 and 500 nm was recorded.

The invention claimed is:

1. A compound of formula (I)

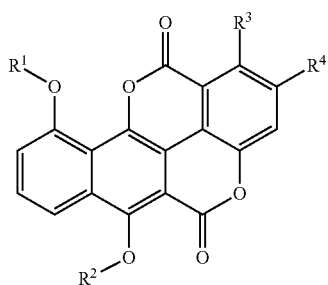

(I)

wherein
R¹ is fucose-digitalose or a 1,4'-bipiperidine-1'carboxylate group;
R² is a hydrogen atom, or a 1,4'-bipiperidine-1'carboxylate group, or a group of formula —X—(CH₂—CH₂—O)ₙ—R⁵ wherein X is a bond, a —C(=O)—, —C(=O)—O— or a —C(=O)—Y—O— group wherein Y is an alkylene group, n is an integer of from 2 to 100, and R⁵ is hydrogen or an alkyl group;
R³ is a hydrogen atom, a halogen atom, a hydroxy group, a (C₁-C₈) alkoxy group, a (C₂-C₈) alkyl group, a (C₂-C₈) haloalkyl group, a (C₂-C₈) alkenyl group, or a (C₂-C₈) alkynyl group and R⁴ is hydrogen; or
R³ is hydrogen and R⁴ is a hydrogen atom, a halogen atom, a hydroxy group, a (C₁-C₈) alkoxy group, a (C₂-C₈) alkyl group, a (C₂-C₈) haloalkyl group, a (C₂-C₈) alkenyl group, or a (C₂-C₈) alkynyl group;
or a pharmaceutically acceptable salt, solvate or hydrate or a pharmaceutically acceptable formulation thereof.

2. A compound according to claim 1, wherein R² is a hydrogen atom or a 1,4'-bipiperidine-1'carboxylate group.

3. A compound according to claim 1, wherein R² is a group of formula —X—(CH₂—CH₂—O)ₙ—R⁵ wherein X is a bond, a —C(=O)—, —C(=O)—O— or a —C(=O)—Y—O-group, wherein Y is a group of formula (CH₂)ₘ, wherein m is an integer from 1 to 20, n is an integer of from 2 to 100, and R⁵ is hydrogen or an alkyl group.

4. A compound according to claim 1, wherein R³ is an ethyl or a vinyl group and R⁴ is a hydrogen atom or wherein R⁴ is an ethyl or a vinyl group and R³ is a hydrogen atom.

5. A compound selected from the group consisting of:

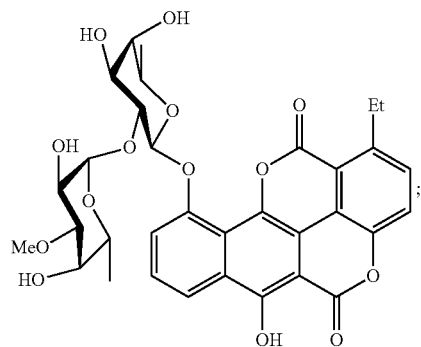

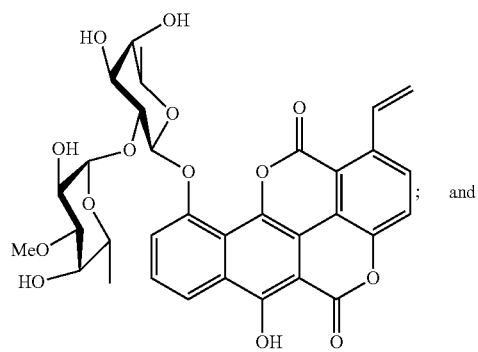

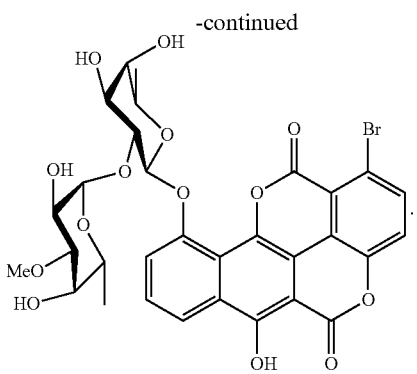

6. A compound of formula (II):

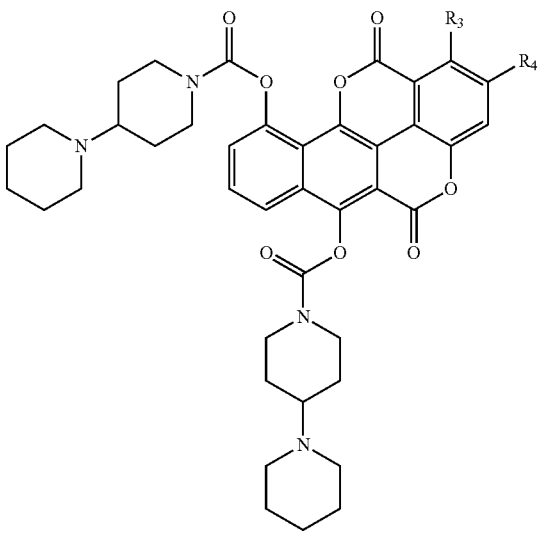

wherein

R³ is selected from a hydrogen atom, a halogen atom, a hydroxy group, a $(C_1-C_8)$ alkoxy group, a $(C_1-C_8)$ alkyl group, a $(C_1-C_8)$ haloalkyl group, a $(C_2-C_8)$ alkenyl group, or a $(C_2-C_8)$ alkynyl group and R⁴ is hydrogen; or R³ is hydrogen and R⁴ is selected from a hydrogen atom, a halogen atom, a hydroxy group, a $(C_1-C_8)$ alkoxy group, a $(C_1-C_8)$ alkyl group, a $(C_1-C_8)$ haloalkyl group, a $(C_2-C_8)$ alkenyl group, or a $(C_2-C_8)$ alkynyl group;

or a pharmaceutically acceptable salt, solvate or hydrate or a pharmaceutically acceptable formulation thereof.

7. A compound according to claim 6, wherein R³ is a hydrogen atom, a halogen atom, a hydroxy group, a $(C_1-C_8)$ alkoxy group, a $(C_2-C_8)$ alkyl group, a $(C_2-C_8)$ haloalkyl group, a $(C_2-C_8)$ alkenyl group, or a $(C_2-C_8)$ alkynyl group and R⁴ is hydrogen; or wherein R³ is hydrogen and R⁴ is a hydrogen atom, a halogen atom, a hydroxy group, a $(C_1-C_8)$ alkoxy group, a $(C_2-C_8)$ alkyl group, a $(C_2-C_8)$ haloalkyl group, a $(C_2-C_8)$ alkenyl group, or a $(C_2-C_8)$ alkynyl group.

8. A compound according to claim 6, wherein R³ is an ethyl or a vinyl group and R⁴ is a hydrogen atom or wherein R⁴ is an ethyl or a vinyl group and R³ is a hydrogen atom.

9. A pharmaceutical composition comprising a compound according to claim 1, claim 5, or claim 6 or a pharmaceutically acceptable salt, solvate or hydrate thereof, optionally in combination with a pharmaceutically acceptable carrier.

10. A compound according to claim 1, claim 5, or claim 6 for use in the treatment of cancer, psoriasis or bacterial infections.

11. A pharmaceutical composition according to claim 9 for use in the treatment of cancer, psoriasis or bacterial infections.

* * * * *

SEQUENCE LISTING

<160> NUMBER OF SEQ ID NOS: 3

<210> SEQ ID NO 1
<211> LENGTH: 59
<212> TYPE: DNA
<213> ORGANISM: Artificial Sequence
<220> FEATURE:
<223> OTHER INFORMATION: Primer chaABC-PTL to amplify the spectinomycin
      resistance gene (aadA) flanked by FRT sites

<400> SEQUENCE: 1
tcaatgggcc gcacttgtcg gctcgagagg atttccatga ttccggggat ccgtcgacc         59

<210> SEQ ID NO 2
<211> LENGTH: 58
<212> TYPE: DNA
<213> ORGANISM: Artificial Sequence
<220> FEATURE:
<223> OTHER INFORMATION: Primer chaABC-PTR to amplify the spectinomycin
      resistance gene (aadA) flanked by FRT sites

<400> SEQUENCE: 2
ggccccggcc cggctgccgg gcccggtccc gcttcgtcat gtaggctgga gctgcttc          58

<210> SEQ ID NO 3
<211> LENGTH: 1520
<212> TYPE: DNA
<213> ORGANISM: Arthroderma benhamiae

<400> SEQUENCE: 3
ccaaggatcc accttggctc acacaaaata ttaccaacga cttgctacca tcggccttca        60
ctatggaccg gctttccagt gccttagcgg gaatgtggag tgtggtaaag gcttcgcaac       120
tggagaaatc acctgggagc ctaagagggt ttccactggt gatgactcca gcgccagtgt       180
gcttcatcct accttcttgg attcctccct ccacccaatc ttcgctgcag tggaaggtct       240
catgggccac agtattacgg agtcctttat ccctactttc atgcgctctt tgaaaatttc       300
tggtcttctt aaccgtaagg agtacaaatg cgatggattc aaggccaacg ttgctgtcga       360
cagctggatg cacggacccc gtgttgccat tagcaatatt ggtattgagt ccaaggaggg       420
ccagcttctt gcggatattg aaggtctaga actcaccagc cttggaagcg atgctgatga       480
ccagcagaag agaactcttt tcttcggcat ccagtggaag ccggctttcg agttcctgac       540
tcctgctcaa gcccagaacc tcagcgtccc tgagattgtt gacctctacg tccaccagaa       600
ccctaatttg cacttccttc actactctga ctcccatacc tctaccttgg acatcctgaa       660
ccatcttggt ggctctaatg gagagaggcg caaattcggc aaaatgactg tggtgccagt       720
tggttcagcg gaggaggcaa gcttctctcc ccttgttgaa cgctggaatg gccttgtttc       780

```
gctcgaggtc actcttgatg agaagtttga tgtgataata atctcctctt cagctgaagc    840
tgcttccatt gagaatctcc atgagaacgg ccttgttata tcccatcctg caaaggctcc    900
cactgccgac aaccttagac aattatgggc cacttcggat gtggccgtct tgaagggcgg    960
tgatgaatca gtgttcactc ctgagactct taccattctc atgccatcta atccatctac   1020
agagactgaa gctctcgcca aaagaattga atcgaccacc tcagcaaagg ttactagaaa   1080
agacttcctg tctctcagaa atggcacacg aatggacgac aatgttatt  ctctctacgc   1140
cctcgatgta aacatcttct acgatgagcc atccaaggct ttgaacgaat tcaaggcagt   1200
ccagtccctc acaagcgatg caaaccgcaa cattgtttgg cttagccagg gtaccttcat   1260
ggattgcccc tgcccagagc aagctatgtt cccaggcctt gctcgctctg ttcgtcatga   1320
aactgaagac ttgagaattg caattcttga tataactaag tctgctaaag ctgatctctc   1380
tgccgatctc attctccgca tcctcaaccc aaccctccat gaagaagaaa ttgcgcttcg   1440
aaatggccaa atccatgtct cccgattgca cgcaaatgat gagttgaact ctaagattgc   1500
cggaggctac ggatccttgg                                              1520
```